(12) United States Patent
Dickey et al.

(10) Patent No.: US 9,186,400 B2
(45) Date of Patent: Nov. 17, 2015

(54) COMPOSITIONS FOR STIMULATION OF MAMMALIAN INNATE IMMUNE RESISTANCE TO PATHOGENS

(71) Applicant: The Board of Regents, The University of Texas System, Austin, TX (US)

(72) Inventors: Burton Dickey, Houston, TX (US); Michael Tuvim, Houston, TX (US); Scott Evans, Houston, TX (US)

(73) Assignee: The Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 14/519,834

(22) Filed: Oct. 21, 2014

(65) Prior Publication Data

US 2015/0125492 A1 May 7, 2015

Related U.S. Application Data

(62) Division of application No. 13/259,761, filed as application No. PCT/US2010/028658 on Mar. 25, 2010, now Pat. No. 8,883,174.

(60) Provisional application No. 61/179,246, filed on May 18, 2009, provisional application No. 61/163,137, filed on Mar. 25, 2009.

(51) Int. Cl.
| | |
|---|---|
| A61K 39/39 | (2006.01) |
| A61K 9/00 | (2006.01) |
| A61K 45/06 | (2006.01) |
| A61K 38/08 | (2006.01) |
| A61K 31/7125 | (2006.01) |
| A61K 39/00 | (2006.01) |

(52) U.S. Cl.
CPC .............. *A61K 39/39* (2013.01); *A61K 9/0078* (2013.01); *A61K 31/7125* (2013.01); *A61K 38/08* (2013.01); *A61K 45/06* (2013.01); *A61K 2039/54* (2013.01); *A61K 2039/55561* (2013.01)

(58) Field of Classification Search
None
See application file for complete search history.

(56) References Cited

U.S. PATENT DOCUMENTS

| | | |
|---|---|---|
| 3,608,066 A | 9/1971 | Illartein |
| 4,406,889 A | 9/1983 | Hartmann et al. |
| 4,406,890 A | 9/1983 | Tarcsay et al. |
| 4,423,038 A | 12/1983 | Baschang et al. |
| 4,439,425 A | 3/1984 | Tarcsay et al. ................ 424/177 |
| 4,666,886 A | 5/1987 | Baschang et al. ............... 514/17 |
| 4,668,218 A | 5/1987 | Virtanen |
| 4,689,338 A | 8/1987 | Gerster |
| 4,929,624 A | 5/1990 | Gerster et al. |
| 5,238,944 A | 8/1993 | Wick et al. |
| 5,266,575 A | 11/1993 | Gerster et al. |
| 5,268,376 A | 12/1993 | Gester |
| 5,346,905 A | 9/1994 | Gerster |
| 5,352,784 A | 10/1994 | Nikolaides et al. |
| 5,389,640 A | 2/1995 | Gerster et al. |
| 5,395,937 A | 3/1995 | Nikolaides et al. |
| 5,432,157 A | 7/1995 | Metzger et al. |
| 5,458,135 A | 10/1995 | Patton et al. |
| 5,494,916 A | 2/1996 | Lindstrom et al. |
| 5,525,612 A | 6/1996 | Gerster |
| 5,700,910 A | 12/1997 | Metzger et al. |
| 6,024,964 A | 2/2000 | Jung et al. |
| 6,039,969 A | 3/2000 | Tomai et al. |
| 6,066,447 A | 5/2000 | De Mesmaeker et al. |
| 6,110,929 A | 8/2000 | Gerster et al. |
| 6,214,806 B1 | 4/2001 | Krieg et al. ................ 514/44 |
| 6,218,371 B1 | 4/2001 | Krieg et al. |
| 6,239,116 B1 | 5/2001 | Krieg et al. |
| 6,288,042 B1 | 9/2001 | Rando et al. |
| 6,294,177 B1 | 9/2001 | Fattom |
| 6,331,539 B1 | 12/2001 | Crooks et al. |
| 6,339,068 B1 | 1/2002 | Krieg et al. |
| 6,406,705 B1 | 6/2002 | Davis et al. |
| 6,429,199 B1 | 8/2002 | Krieg et al. ................ 514/44 |
| 6,451,810 B1 | 9/2002 | Coleman et al. |
| 6,488,953 B2 | 12/2002 | Halliday et al. |
| 6,517,839 B1 | 2/2003 | Modlin et al. |
| 6,534,062 B2 | 3/2003 | Raz et al. |
| 6,552,006 B2 | 4/2003 | Raz et al. |
| 6,727,230 B1 | 4/2004 | Hutcherson et al. |
| 6,737,045 B2 | 5/2004 | Patton et al. |
| 6,794,357 B1 | 9/2004 | Backstrom et al. |
| 6,797,258 B2 | 9/2004 | Platz et al. |
| 6,815,429 B2 | 11/2004 | Agrawal et al. |
| 6,929,798 B2 | 8/2005 | Pillich et al. |
| 6,949,520 B1 | 9/2005 | Hartmann et al. |
| 6,977,245 B2 | 12/2005 | Klinman et al. |

(Continued)

FOREIGN PATENT DOCUMENTS

| | | |
|---|---|---|
| EP | 1 550 458 | 7/2005 |
| EP | 1 707 232 | 8/2010 |

(Continued)

OTHER PUBLICATIONS

Merkus et al. Rhinology, 44, 102-107, 2006.*
Abuchowski et al., "Effect of covalent attachment of polyethylene glycol on immunogenicity and circulating life of bovine liver catalase," *J. Biol. Chem.*, 252:3582-6, 1977.
Adachi et al., "Targeted disruption of the MyD88 gene results in loss of IL-1- and IL-18- mediated function," *Immunity*, 9:143-150, 1998.

(Continued)

*Primary Examiner* — Oluwatosin Ogunbiyi
(74) *Attorney, Agent, or Firm* — Norton Rose Fulbright US LLP

(57) ABSTRACT

Embodiments of the invention are directed to methods of treating, inhibiting or attenuating a microbial infection in an individual who has or is at risk for developing such an infection, comprising the step of administering an effective amount of a StIR composition to the individual.

20 Claims, 20 Drawing Sheets

(56) References Cited

U.S. PATENT DOCUMENTS

| | | |
|---|---|---|
| 7,001,890 B1 | 2/2006 | Wagner et al. |
| 7,038,029 B2 | 5/2006 | Lopez et al. |
| 7,105,495 B2 | 9/2006 | Agrawal et al. |
| 7,115,579 B2 | 10/2006 | Agrawal et al. |
| 7,157,437 B2 | 1/2007 | Nest .................................. 514/44 |
| 7,176,296 B2 | 2/2007 | Agrawal et al. |
| 7,271,156 B2 | 9/2007 | Krieg et al. |
| 7,276,489 B2 | 10/2007 | Agrawal et al. |
| 7,276,515 B2 | 10/2007 | Dellaria et al. |
| 7,329,409 B2 | 2/2008 | Pillich et al. |
| 7,358,068 B2 | 4/2008 | Vaillant et al. |
| 7,371,734 B2 | 5/2008 | Phillips et al. |
| 7,381,807 B2 | 6/2008 | Lopez et al. |
| 7,393,859 B2 | 7/2008 | Coleman et al. |
| 7,402,572 B2 | 7/2008 | Krieg et al. |
| 7,405,204 B2 | 7/2008 | Roberts et al. |
| 7,405,285 B2 | 7/2008 | Agrawal et al. |
| 7,408,050 B2 | 8/2008 | Kim et al. |
| 7,410,975 B2 | 8/2008 | Lipford et al. |
| 7,425,548 B2 | 9/2008 | Nair et al. |
| 7,427,405 B2 | 9/2008 | Agrawal et al. |
| 7,427,629 B2 | 9/2008 | Kedl et al. |
| 7,488,490 B2 | 2/2009 | Davis et al. |
| 7,491,706 B2 | 2/2009 | Yu et al. |
| 7,498,425 B2 | 3/2009 | Agrawal et al. |
| 7,498,426 B2 | 3/2009 | Agrawal et al. |
| 7,507,802 B2 | 3/2009 | Ahn et al. |
| 7,517,861 B2 | 4/2009 | Krieg et al. |
| 7,521,063 B2 | 4/2009 | Klinman et al. |
| 7,534,772 B2 | 5/2009 | Weiner et al. |
| 7,544,697 B2 | 6/2009 | Hays et al. |
| 7,550,501 B2 | 6/2009 | Chow et al. |
| 7,566,702 B2 | 7/2009 | Agrawal et al. |
| 7,566,703 B2 | 7/2009 | Krieg et al. |
| 7,569,553 B2 | 8/2009 | Krieg et al. |
| 7,576,066 B2 | 8/2009 | Krieg et al. |
| 7,585,847 B2 | 9/2009 | Bratzler et al. |
| 7,598,382 B2 | 10/2009 | Hays et al. |
| 7,605,138 B2 | 10/2009 | Krieg et al. |
| 7,612,083 B2 | 11/2009 | Griesgraber et al. |
| 7,615,539 B2 | 11/2009 | Uhlmann et al. |
| 7,713,529 B2 | 5/2010 | Krieg et al. ................ 424/184.1 |
| 7,723,022 B2 | 5/2010 | Krieg et al. ........................ 435/5 |
| 7,884,083 B2 | 2/2011 | Van Nest et al. ................ 514/44 |
| 8,158,592 B2 | 4/2012 | Krieg et al. ........................ 514/44 |
| 8,158,768 B2 | 4/2012 | Dina et al. .................... 536/23.1 |
| 8,226,957 B2 | 7/2012 | Van Nest ................... 424/211.1 |
| 8,283,328 B2 | 10/2012 | Krieg et al. ........................ 514/44 |
| 8,309,527 B2 | 11/2012 | Krieg et al. ........................ 514/44 |
| 8,518,905 B2 | 8/2013 | Hackam et al. ................ 514/44 |
| 8,871,732 B2 | 10/2014 | Dina et al. ........................ 514/44 |
| 2002/0045737 A1 | 4/2002 | Choi et al. |
| 2002/0142977 A1 | 10/2002 | Raz et al. |
| 2003/0091599 A1 | 5/2003 | Davis et al. |
| 2003/0148976 A1 | 8/2003 | Krieg et al. |
| 2003/0181406 A1 | 9/2003 | Schetter et al. |
| 2003/0212028 A1 | 11/2003 | Raz et al. |
| 2003/0224010 A1 | 12/2003 | Davis et al. |
| 2003/0225016 A1 | 12/2003 | Fearon et al. |
| 2003/0232074 A1 | 12/2003 | Lipford et al. |
| 2004/0006032 A1 | 1/2004 | Lopez et al. |
| 2004/0009949 A1 | 1/2004 | Krieg et al. |
| 2004/0053880 A1 | 3/2004 | Krieg et al. |
| 2004/0058883 A1 | 3/2004 | Phillips et al. |
| 2004/0067905 A1 | 4/2004 | Krieg et al. |
| 2004/0087534 A1 | 5/2004 | Krieg et al. |
| 2004/0091491 A1 | 5/2004 | Kedl et al. |
| 2004/0092472 A1 | 5/2004 | Krieg et al. |
| 2004/0106568 A1 | 6/2004 | Krieg et al. |
| 2004/0141950 A1 | 7/2004 | Noelle et al. |
| 2004/0152649 A1 | 8/2004 | Krieg et al. |
| 2004/0152657 A1 | 8/2004 | Krieg et al. |
| 2004/0162309 A1 | 8/2004 | Gorden et al. |
| 2004/0171086 A1 | 9/2004 | Fink et al. |
| 2004/0171150 A1 | 9/2004 | Krieg et al. |
| 2004/0171571 A1 | 9/2004 | Krieg et al. |
| 2004/0181045 A1 | 9/2004 | Krieg et al. |
| 2004/0198680 A1 | 10/2004 | Krieg et al. |
| 2004/0198688 A1 | 10/2004 | Krieg et al. |
| 2004/0229835 A1 | 11/2004 | Krieg et al. |
| 2004/0234512 A1 | 11/2004 | Wagner et al. |
| 2004/0235770 A1 | 11/2004 | Davis et al. |
| 2004/0235777 A1 | 11/2004 | Wagner et al. |
| 2004/0235778 A1 | 11/2004 | Wagner et al. |
| 2004/0248834 A1 | 12/2004 | Klinman et al. |
| 2004/0248837 A1 | 12/2004 | Raz et al. |
| 2005/0004061 A1 | 1/2005 | Krieg et al. |
| 2005/0004062 A1 | 1/2005 | Krieg et al. |
| 2005/0009774 A1 | 1/2005 | Krieg et al. |
| 2005/0013812 A1 | 1/2005 | Dow et al. |
| 2005/0026861 A1 | 2/2005 | Kandimalla et al. |
| 2005/0032734 A1 | 2/2005 | Krieg et al. |
| 2005/0037403 A1 | 2/2005 | Krieg et al. |
| 2005/0043529 A1 | 2/2005 | Krieg et al. |
| 2005/0049215 A1 | 3/2005 | Krieg et al. |
| 2005/0049216 A1 | 3/2005 | Krieg et al. |
| 2005/0054601 A1 | 3/2005 | Wagner et al. |
| 2005/0054602 A1 | 3/2005 | Krieg et al. |
| 2005/0059619 A1 | 3/2005 | Krieg et al. |
| 2005/0059625 A1 | 3/2005 | Krieg et al. |
| 2005/0075302 A1 | 4/2005 | Hutcherson et al. |
| 2005/0100983 A1 | 5/2005 | Bauer et al. |
| 2005/0101554 A1 | 5/2005 | Krieg et al. |
| 2005/0107297 A1 | 5/2005 | Holmes et al. |
| 2005/0119273 A1 | 6/2005 | Lipford et al. |
| 2005/0123523 A1 | 6/2005 | Krieg et al. |
| 2005/0130911 A1 | 6/2005 | Uhlmann et al. |
| 2005/0130918 A1 | 6/2005 | Agrawal et al. |
| 2005/0163764 A1 | 7/2005 | Medzhitov et al. |
| 2005/0169888 A1 | 8/2005 | Hartmann et al. |
| 2005/0171047 A1 | 8/2005 | Krieg et al. |
| 2005/0181422 A1 | 8/2005 | Bauer et al. |
| 2005/0214359 A1 | 9/2005 | Stegmann |
| 2005/0215500 A1 | 9/2005 | Krieg et al. |
| 2005/0215501 A1 | 9/2005 | Lipford et al. |
| 2005/0222072 A1 | 10/2005 | Wang et al. |
| 2005/0233995 A1 | 10/2005 | Krieg et al. |
| 2005/0239733 A1 | 10/2005 | Jurk et al. |
| 2005/0239734 A1 | 10/2005 | Uhlmann et al. |
| 2005/0239735 A1 | 10/2005 | Miller et al. |
| 2005/0239736 A1 | 10/2005 | Krieg et al. |
| 2005/0244379 A1 | 11/2005 | Krieg et al. |
| 2005/0244380 A1 | 11/2005 | Krieg et al. |
| 2005/0244505 A1 | 11/2005 | Higbee et al. |
| 2005/0245477 A1 | 11/2005 | Krieg et al. |
| 2005/0256073 A1 | 11/2005 | Lipford et al. |
| 2005/0261215 A1 | 11/2005 | Garren et al. |
| 2005/0276789 A1 | 12/2005 | Lopez et al. |
| 2005/0277604 A1 | 12/2005 | Krieg et al. |
| 2005/0277609 A1 | 12/2005 | Krieg et al. |
| 2005/0287612 A1 | 12/2005 | Bertin et al. |
| 2006/0003955 A1 | 1/2006 | Krieg et al. |
| 2006/0003962 A1 | 1/2006 | Ahluwalia et al. |
| 2006/0009501 A1 | 1/2006 | Nair et al. |
| 2006/0014713 A1 | 1/2006 | Agrawal et al. |
| 2006/0019916 A1 | 1/2006 | Krieg et al. |
| 2006/0019919 A1 | 1/2006 | Agrawal et al. |
| 2006/0019923 A1 | 1/2006 | Davis et al. |
| 2006/0025365 A1 | 2/2006 | Agrawal et al. |
| 2006/0058251 A1 | 3/2006 | Krieg et al. |
| 2006/0089326 A1 | 4/2006 | Krieg et al. |
| 2006/0094680 A1 | 5/2006 | Agrawal et al. |
| 2006/0094681 A1 | 5/2006 | Agrawal et al. |
| 2006/0094683 A1 | 5/2006 | Krieg et al. |
| 2006/0140875 A1 | 6/2006 | Krieg et al. |
| 2006/0154890 A1 | 7/2006 | Bratzler et al. |
| 2006/0172966 A1 | 8/2006 | Lipford et al. |
| 2006/0188475 A1 | 8/2006 | Xu et al. |
| 2006/0188913 A1 | 8/2006 | Krieg et al. |
| 2006/0211644 A1 | 9/2006 | Krieg et al. |
| 2006/0217328 A1 | 9/2006 | Kandimalla et al. |
| 2006/0229271 A1 | 10/2006 | Krieg et al. |
| 2006/0241076 A1 | 10/2006 | Uhlmann et al. |
| 2006/0246035 A1 | 11/2006 | Ahluwalia et al. |

(56) References Cited

U.S. PATENT DOCUMENTS

| | | | |
|---|---|---|---|
| 2006/0286070 A1 | 12/2006 | Hartmann et al. | |
| 2006/0287263 A1 | 12/2006 | Davis et al. | |
| 2006/0292179 A1 | 12/2006 | Ducatelle et al. | |
| 2007/0004654 A1* | 1/2007 | Raz et al. | 514/43 |
| 2007/0009482 A9 | 1/2007 | Krieg et al. | |
| 2007/0010470 A9 | 1/2007 | Krieg et al. | |
| 2007/0026018 A1 | 2/2007 | Ellis et al. | |
| 2007/0037767 A1 | 2/2007 | Bratzler et al. | |
| 2007/0049550 A1 | 3/2007 | Fearon et al. | |
| 2007/0066553 A1 | 3/2007 | Krieg et al. | |
| 2007/0066554 A1 | 3/2007 | Krieg et al. | |
| 2007/0078104 A1 | 4/2007 | Krieg et al. | |
| 2007/0129320 A9 | 6/2007 | Davis et al. | |
| 2007/0142315 A1 | 6/2007 | Forsbach et al. | |
| 2007/0167409 A1 | 7/2007 | Chow et al. | |
| 2007/0179103 A1 | 8/2007 | Agrawal et al. | |
| 2007/0184465 A1 | 8/2007 | Wagner et al. | |
| 2007/0202128 A1 | 8/2007 | Krieg et al. | |
| 2007/0219153 A1 | 9/2007 | Kandimalla et al. | |
| 2007/0224210 A1 | 9/2007 | Krieg et al. | |
| 2007/0232622 A1 | 10/2007 | Lipford et al. | |
| 2008/0009455 A9 | 1/2008 | Krieg et al. | |
| 2008/0031936 A1 | 2/2008 | Krieg et al. | |
| 2008/0045473 A1 | 2/2008 | Uhlmann et al. | |
| 2008/0070907 A1 | 3/2008 | Griesgraber et al. | |
| 2008/0089883 A1 | 4/2008 | Kandimalla et al. | |
| 2008/0113929 A1 | 5/2008 | Lipford et al. | |
| 2008/0114019 A1 | 5/2008 | Kshirsagar et al. | |
| 2008/0124366 A1 | 5/2008 | Ohlfest et al. | |
| 2008/0170996 A1 | 7/2008 | Dickey et al. | |
| 2008/0171712 A1 | 7/2008 | Kandimalla et al. | |
| 2008/0193437 A1 | 8/2008 | Agrawal et al. | |
| 2008/0193468 A1 | 8/2008 | Levy et al. | |
| 2008/0207674 A1 | 8/2008 | Stoesz et al. | |
| 2008/0226649 A1 | 9/2008 | Schetter et al. | |
| 2008/0241139 A1 | 10/2008 | Delucia et al. | |
| 2008/0249056 A1 | 10/2008 | Klinman et al. | |
| 2008/0269192 A1 | 10/2008 | Griesgraber et al. | |
| 2008/0279785 A1 | 11/2008 | Kandimalla et al. | |
| 2008/0292648 A1 | 11/2008 | Kandimalla et al. | |
| 2008/0306252 A1 | 12/2008 | Crooks et al. | |
| 2008/0312434 A1 | 12/2008 | Lindstrom et al. | |
| 2008/0318998 A1 | 12/2008 | Prince et al. | |
| 2009/0017021 A1 | 1/2009 | Davis et al. | |
| 2009/0017075 A1 | 1/2009 | Van Nest et al. | |
| 2009/0017076 A1 | 1/2009 | Miller et al. | |
| 2009/0029988 A1 | 1/2009 | Kshirsagar et al. | |
| 2009/0030031 A1 | 1/2009 | Kshirsagar et al. | |
| 2009/0042925 A1 | 2/2009 | Kshirsagar et al. | |
| 2009/0053148 A1 | 2/2009 | Kandimalla et al. | |
| 2009/0053206 A1 | 2/2009 | Kandimalla et al. | |
| 2009/0060898 A1 | 3/2009 | Kandimalla et al. | |
| 2009/0060927 A1 | 3/2009 | Wagner et al. | |
| 2009/0060937 A1 | 3/2009 | Lopez et al. | |
| 2009/0062328 A1 | 3/2009 | Kshirsagar et al. | |
| 2009/0069299 A1 | 3/2009 | Merrill et al. | |
| 2009/0069314 A1 | 3/2009 | Kshirsagar et al. | |
| 2009/0075980 A1 | 3/2009 | Hays et al. | |
| 2009/0087388 A1 | 4/2009 | Kandimalla et al. | |
| 2009/0087446 A1 | 4/2009 | Vollmer et al. | |
| 2009/0098063 A1 | 4/2009 | Kandimalla et al. | |
| 2009/0099122 A1 | 4/2009 | Klinman et al. | |
| 2009/0105295 A1 | 4/2009 | Kshirsagar et al. | |
| 2009/0117132 A1 | 5/2009 | Readett et al. | |
| 2009/0123460 A1 | 5/2009 | Noelle et al. | |
| 2009/0124611 A1 | 5/2009 | Hays et al. | |
| 2009/0137519 A1 | 5/2009 | Krieg et al. | |
| 2009/0142362 A1 | 6/2009 | Krieg et al. | |
| 2009/0155307 A1 | 6/2009 | Davis et al. | |
| 2009/0163532 A1 | 6/2009 | Perman et al. | |
| 2009/0163533 A1 | 6/2009 | Hays et al. | |
| 2009/0169529 A1 | 7/2009 | Hartmann et al. | |
| 2009/0176696 A1 | 7/2009 | Mills et al. | |
| 2009/0176821 A1 | 7/2009 | Kshirsagar et al. | |
| 2009/0191188 A1 | 7/2009 | Krieg et al. | |
| 2009/0208468 A1 | 8/2009 | Klinman et al. | |
| 2009/0214578 A1 | 8/2009 | Bauer et al. | |
| 2009/0220528 A1 | 9/2009 | Turka et al. | |
| 2009/0253695 A1 | 10/2009 | Kshirsagar et al. | |
| 2009/0263405 A1 | 10/2009 | Verthelyi et al. | |
| 2009/0306017 A1 | 12/2009 | Kuritz | |
| 2009/0306177 A1 | 12/2009 | Uhlmann et al. | |
| 2009/0311277 A1 | 12/2009 | Krieg et al. | |
| 2009/0318337 A1 | 12/2009 | Lowell et al. | |
| 2009/0324639 A1 | 12/2009 | Lowell et al. | |

FOREIGN PATENT DOCUMENTS

| | | |
|---|---|---|
| WO | WO 94/06498 | 3/1994 |
| WO | WO 94/08552 | 4/1994 |
| WO | WO 94/16970 | 8/1994 |
| WO | WO 97/25086 | 7/1997 |
| WO | WO 98/16427 | 4/1998 |
| WO | WO 98/35888 | 8/1998 |
| WO | WO 98/55495 | 12/1998 |
| WO | WO 02/46189 | 6/2002 |
| WO | WO 02/46192 | 6/2002 |
| WO | WO 03/035695 | 5/2003 |
| WO | WO 03/067991 | 8/2003 |
| WO | WO 2008/085549 | 7/2008 |

OTHER PUBLICATIONS

Akinbi et al., "Bacterial killing is enhanced by expression of lysozyme in the lungs of transgenic mice," *J. Immunol.*, 165(10):5760-6, 2000.

Akira et al., "Role of adapters in Toll-like receptor signaling," *Biochem. Soc. Trans.*, 31(Pt 3):637-42, 2003.

Aliprantis et al., "Cell activation and apoptosis by bacterial lipoproteins through toll-like receptor-2," *Science*, 285:736-739, 1999.

Apidianakis et al., "Profiling early infection responses: *Pseudomonas aeruginosa* eludes host defenses by suppressing antimicrobial peptide gene expression," *Proc. Natl. Acad. Sci. U.S.A.*, 102:2573-2578, 2005.

Bafika et al., "Cutting edge: TLR9 and TLR2 signaling together account for MyD88-dependent control of parasitemia in *Trypanosoma cruzi* infection,"*J Immunol,*. 177:3515-3519, 2006.

Bals and Hiemstra, "Antimicrobial peptides in COPD—basic biology and therapeutic applications," *Curr. Drug Targets*, 7(6):743-50, 2006.

Bals and Hiemstra, "Innate immunity in the lung: how epithelial cells fight against respiratory pathogens," *Eur. Respir. J.*, 23(2):327-333. 20, 2004.

Bals et al., "Augmentation of innate host defense by expression of a cathelicidin antimicrobial peptide," *Infect. Immun.*, 67:6084-6089, 1999.

Bals et al., "Mouse beta-defensin 3 is an inducible antimicrobial peptide expressed in the epithelia of multiple organs,"*Infect. Immun.*, 67:3542-3547, 1999.

Beauchamp et al., "A new procedure for the synthesis of polyethylene glycol-protein adducts; effects on function, receptor recognition, and clearance of superoxide dismutase, lactoferrin, and alpha 2-macroglobulin," *Anal Biochem.*, 131:25-33, 1983.

Becker et al., "CD14-dependent lipopolysaccharide-induced beta-defensin-2 expression in human tracheobronchial epithelium," *J.Biol. Chem.*, 275:29731-29736, 2000.

Bernard, "Acute respiratory distress syndrome: a historical perspective," *Am. J. Respir. Crit Care Med.*, 172:798-806, 2005.

Beutler, "TLRs and innate immunity," *Blood*, 113:1399-1407, 2009.

Brown et al., "Complexities of targeting innate immunity to treat infection," *Trends in Immunology*, 28:260-6, 2007.

Buwitt-Beckmann et al., "Lipopeptide structure determines TLR2 dependent cell activation level," *FEBS J.*, 272:6354-6364, 2005.

Chen et al., "Properties of two urate oxidases modified by the covalent attachment of poly(ethylene glycol)," *Biochim. Biophy. Acta*, 660:293-298, 1981.

Clement et al., "Allergic lung inflammation alters neither susceptibility to *Streptococcus pneumoniae* infection nor inducibility of innate resistance in mice," *Respir. Res.*, 10:70, 2009.

(56) References Cited

OTHER PUBLICATIONS

Clement et al., "Stimulation of innate immune defense protects against *S. pneumoniae* infection," *Proc. Am. Thorac. Soc.*, 2, A452 (abstract), 2005.
Clement et al., "Stimulation of lung innate immunity protects against lethal pneumococcal pneumonia in mice," Am. J. Respir. Grit Care Med., 177:1322-1330, 2008.
Cluff et al., "Synthetic toll-like receptor 4 agonists stimulate innate resistance to infectious challenge," *Infect. Immun.*, 73:3044-3052, 2005.
Cole et al., "Cationic polypeptides are required for antibacterial activity of human airway fluid," *J. Immunol.*, 169:6985-6991, 2002.
Cole el al., "Decreased clearance of *Pseudomonas aeruginosa* from airways of mice deficient in lysozyme M," *J. Leukoc. Biol.*, 78:1081-1085, 2005.
Dearman et al., "Toll-like receptor ligand activation of murine bone marrow-derived dendritic cells," *Immunology*, 126:475-484, 2009.
Deng et al., "CpG oligodeoxynucleotides stimulate protective innate immunity against pulmonary *Klebsiella* infection," *J. Immunol.*, 173:5148-5155, 2004.
Dennis et al., "Tularemia as a biological weapon: medical and public health management," *JAMA*, 285:2763-2773, 2001.
Diamond et al., "Inducible expression of an antibiotic peptide gene in lipopolysaccharide-challenged tracheal epithelial cells," *Proc. Natl. Acad. Sci. U.S.A.*, 93:5156-5160, 1996.
Diamond et al., "The innate immune response of the respiratory epithelium," *Immunol. Rev.*, 173:27-38, 2000.
Edwards et al., "Phosphatidylinositol 3-kinase/Akt signaling in the response of vascular endothelium to ionizing radiation," *Cancer Res.*, 62:4671-4677, 2002.
Evans et al., "Inducible innate resistance of lung epithelium to infection," *Annu. Rev. Physiol.*, (72)413-35, 2010.
Evans et al., "Mucin is produced by clara cells in the proximal airways of antigen-challenged mice," *Am. J. Respir. Cell Mol. Biol.*, 31(4):382-94, 2004.
Evans et al., "Pneumocystis cell wall beta-glucans stimulate alveolar epithelial cell chemokine generation through nuclear factor-kappaB-dependent mechanisms," *Am. J. Respir. Cell Mol. Biol.*, 32(6): 490-497, 2005.
Evans et al., "Stimulated innate resistance of lung epithelium protects mice broadly against bacteria and fungi," *Am. J. Respir. Cell Molec. Biol.*, 42:40-50, 2010.
Fiegel et al., "Airborne infectious disease and the suppression of pulmonary bioaerosols," *Drug Discov. Today*, 11:51-57, 2006.
File, "Community-acquired pneumonia," *Lancet*, 362:1991-2001, 2003.
Finlay & McFadden, "Anti-immunology: evasion of the host immune system by bacterial and viral pathogens," *Cell*, 124:767-782, 2006.
Fischer & Voynow, "Neutrophil elastase induces MUC5AC gene expression in airway epithelium via a pathway involving reactive oxygen species," *Am. J Respir. Cell Mol. Biol.*, 26:447-452, 2002.
Forteza et al., "Regulated hydrogen peroxide production by Duox in human airway epithelial cells," *Am. J. Respir. Cell Mol. Biol.*, 32(5):462-9, 2005.
Foxwell et al., "Mucosal immunization against respiratory bacterial pathogens," *Expert. Rev. Vaccines*, 2:551-60, 2003.
Ghosh et al., "Toll-like receptor (TLR) 2-9 agonists-induced cytokines and chemokines: I. Comparison with T cell receptor-induced responses," *Cell Immunol*, 243:48-57, 2006.
Gorden et al., "Synthetic TLR agonists reveal functional differences between human TLR7 and TLR8," *J. Immunol.*, 174:1259-1268, 2005.
Hackett, "Innate immune activation as a broad-spectrum biodefense strategy: prospects and research challenges," *J. Allergy Clin. Immunol.*, 112:686-694, 2003.
Hajjar et al., "An essential role for non-bone marrow-derived cells in control of *Pseudomonas aeruginosa* pneumonia," *Am. J. Respir. Cell Mol. Biol.*, 33:470-475, 2005.
Hashimoto et al., "The Toll gene of *Drosophila*, required for dorsal-ventral embryonic polarity, appears to encode a transmembrane protein," *Cell*, 52(2):269-279, 1988.
Hayashi et al., "The innate immune response to bacterial flagellin is mediated by Toll-like receptor 5," *Nature*, 410:1099-1103, 2001.
Hertz et al., "Activation of Toll-like receptor 2 on human tracheobronchial epithelial cells induces the antimicrobial peptide human beta defensin-2," *J. Immuno.*, 171:6820-6826, 2003.
Hilleman, "Overview: cause and prevention in biowarfare and bioterrorism," *Vaccine*, 20:3055-3067, 2002.
Hoffman et al., "TLR-targeted therapeutics," *Nature Reviews*, 4:879-80, 2005.
Holtzman et al., "Immunity, inflammation, and remodeling in the airway epithelial barrier: epithelial-viral-allergic paradigm," *Physiol. Rev.*, 82:19-46, 2002.
Homer et al., "Differential expression of chitinases identify subsets of murine airway epithelial cells in allergic inflammation," *Am. J. Physiol Lung Cell Mol. Physiol.*, 291:L502-L511, 2006.
International Search Report and Written Opinion issued in PCT/US2010/028658, dated Jul. 14, 2010.
International Search Report and Written Opinion, issued in Application No. PCT/US2009/056525, mailed Mar. 26, 2010.
Ishii et al., "Host innate immune receptors and beyond: making sense of microbial infections," *Cell Host and Microbe*, 3:352-363, 2008.
Iwasaki, "Mucosal dendritic cells," *Annu. Rev. Immunol.*, 25:381-418, 2007.
Janeway, Jr. & Medzhitov, "Innate immune recognition," *Annu. Rev. Immunol.*, 20:197-216, 2002.
Jean et al., "Protective effect of endotoxin instillation on subsequent bacteria-induced acute lung injury in rats," *Am. J. Respir. Crit. Care Med.*, 158:1702-1708, 1998.
Joos & Tamm, "Breakdown of pulmonary host defense in the immunocompromised host: cancer chemotherapy," *Proc.Am.Thorac. Soc.*, 2:445-448, 2005.
Kaisho et al., "Toll-like receptors as adjuvant receptors," *Biochim. Biophys. Acta*, 1589(1):1-13, 2002.
Kearney et al., "Visualization of peptide-specific T cell immunity and peripheral tolerance induction in vivo," *Immunity*, 1:327, 1994.
Kingma & Whitsett, "In defense of the lung: surfactant protein A and surfactant protein D," *Curr. Opin. Pharmacol.*, 6:277-283, 2006.
Kita et al., "Characterization of a polyethylene glycol conjugate of recombinant human interferon-gamma," *Drug Des. Delivery*, 6:157-167, 1990.
Klempt et al., "Identification of epithelial and myeloid-specific DNA elements regulating MRP14 gene transcription," *J. Cell Biochem.*, 73:49-55, 1999.
Knauf et al., "Relationship of effective molecular size to systemic clearance in rats of recombinant interleukin-2 chemically modified with water-soluble polymers," *J. Biol. Chem.*, 263:15064-15070, 1988.
Knowles & Boucher, "Mucus clearance as a primary innate defense mechanism for mammalian airways," *J. Clin. Invest.*, 109:571-577, 2002.
Krug et al., "Identification of CpG oligonucleotide sequences with high induction of IFN-alpha/beta in plasmacytoid dendritic cells," *Eur. J. Immunol.*, 31:2154-2163, 2001.
Lee et al., "Differential modulation of Toll-like receptors by fatty acids: preferential inhibition by n-3 polyunsaturated fatty acids," *J. Lipid Res.*, 44:479-486, 2003.
Lee et al., "Molecular basis for the immunostimulatory activity of guanine nucleoside analogs: activation of Toll-like receptor 7," *Proc. Natl. Acad. Sci. USA*, 100:6646-6651, 2003.
Lee et al.,"TLR-4 pathway mediates the inflammatory response but not bacterial elimination in *E. coli* pneumonia," *Am. J. Physiol. Lung Cell Mol. Physiol.*, 289:L731-L738, 2005.
Legarda et al., "Suppression of NF-kappaB-mediated beta-defensin gene expression in the mammalian airway by the Bordetella type III secretion system," *Cell Microbiol.*, 7:489-497, 2005.
Lemaitre et al., "The dorsoventral regulatory gene cassette spätzle/Toll/cactus controls the potent antifungal response in *Drosophila* adults," *Cell*, 86(6): 973-983, 1996.

(56) References Cited

OTHER PUBLICATIONS

Lin et al., "The murine L-plastin gene promoter: identification and comparison with the human L-plastin gene promoter," *DNA Cell Biol.*, 16(1): 9-16, 1997.
Liu et al., "Toll-like receptor triggering of a vitamin D-mediated human antimicrobial response," *Science*, 311:1770-1773, 2006.
Martin & Frevert, "Innate immunity in the lungs," *Proc. Am. Thorac. Soc.*, 2:403-411, 2005.
Martin et al, "Role of innate immune factors in the adjuvant activity of monophosphoryl lipid A," *Infect. Immun.*, 71:2498-2507, 2003.
Medzhitov & Janeway, "Innate immunity: impact on the adaptive immune response," *Curr. Opin. Immunol.*, 9:4-9, 1997.
Medzhitov & Janeway, Jr., "The Toll receptor family and microbial recognition," *Trends Microbiol.*, 8(10):452-456, 2000.
Medzhitov et al., "MyD88 is an adaptor protein in the hToll/IL-1 receptor family signaling pathways," *Mol. Cell*, 2(2):253-258, 1998.
Moghaddam et al., "Haemophilus influenzae lysate induces aspects of the chronic obstructive pulmonary disease phenotype," *Am. J. Respir. Cell Mol. Biol.*, 38:629-638, 2008.
Moghaddam et al., "Repetitive exposure to an aerosolized lysate of non-typeable Haemophilus influenzae recapitulates some aspects of the COPD phenotype," *Am. J. Respir. Cell Mol. Biol.*, 2007.
Mondino et al., "The anatomy of T-cell activation and tolerance," *Proc. Natl. Acad. Sci. USA*, 93(6):2245-2252, 1996.
Moser et al., "beta-Defensin 1 contributes to pulmonary innate immunity in mice," *Infect. Immun.*, 70:3068-3072, 2002.
Nagase et al., "Expression and function of Toll-like receptors in eosinophils: activation by Toll-like receptor 7 ligand," *J Immunol.*, 171(8)3977-3982, 2003.
Palma-Carlos & Palma Carlos, "Non specific immunomodulation in respiratory infections," *Allergic et Immunologie*, 22:179-185, 1990.
Pastva et al., "Immunomodulatory roles of surfactant proteins A and D: implications in lung disease," *Proc. Am. Thorac. Soc.*, 4:252-257, 2007.
Poltorak et al., "Defective LPS signaling in C3H/HeJ and C57BL/10ScCr mice: mutations in Tlr4 gene," *Science*, 282(5396):2085-2088, 1998.
Pulendran & Ahmed, "Translating innate immunity into immunological memory: implications for vaccine development," *Cell*, 124:849-863, 2006.
Pulendran et al., "Prevention of peripheral tolerance by a dendritic cell growth factor: flt3 ligand as an adjuvant," *J. Exp. Med.*, 188(11):2075-2082, 1998.
Rogan et al., "Antimicrobial proteins and polypeptides in pulmonary innate defense," *Respir. Res.*, 7:29, 2006.
Roman et al., "Immunostimulatory DNA sequences function as T helper-1-promoting adjuvants," *Nat. Med.*, 3(8):849-854, 1997.
Sadikot et al. "Targeted immunomodulation of the NF-kappaB pathway in airway epithelium impacts host defense against *Pseudomonas aeruginosa*," *J. Immunol.*, 176:4923-4930, 2006.
Sato et al., "Dual recognition of herpes simplex viruses by TLR2 and TLR9 in dendritic cells," *Proc. Natl. Acad. Sci.*, 103:17343-17348, 2006.
Scott et al., "Stimulation of lung innate immunity protects against a broad range of infectious microbes," *Mol. Biol. Cell.*, 18 (supp):A1336 (abstract), 2007.
Singh et al., "Production of beta-defensins by human airway epithelia," *Proc. Natl. Acad. Sci. U.S.A.*, 95:14961-14966, 1998.
Song et al., "TLR4 initiated and cAMP mediated abrogation of bacterial invasion of the bladder," *Cell Host. Microbe.*, 1:287-298, 2007.
Takeda & Akira, "Microbial recognition by Toll-like receptors," *J. Dermatol. Sci.*, 34(2):73-82, 2004.
Takeda & Akira, "TLR signaling pathways," *Semin. Immunol.*, 16:3-9, 2004.
Travis et al., "Antimicrobial peptides and proteins in the innate defense of the airway surface," *Curr. Opin. Immunol.*, 13:89-95, 2001.
Trinchieri & Sher, "Cooperation of Toll-like receptor signals in innate immune defense," *Nat. Rev. Immunol.*, 7:179-190, 2007.
Tsutsumi et al., "Polyethylene glycol modification of interleukin-6 enhances its thrombopoietic activity," *J. Controlled Rel.*, 33:447-451, 1995.
Tuvim et al., "Augmented lung inflammation protects against influenza A pneumonia," *PLoS One*, 4:e4176, 2009.
Ulevitch, "Therapeutics targeting the innate immune system," *Nature Reviews*, 4:512-20, 2004.
Vroegop et al., "Pharmacokinetic properties, induction of interferon, and efficacy of selected 5-halo-6-phenyl pyrimidinones, bropirimine analogues, in a model of severe experimental autoimmune encephalomyelitis," *Intl. J. Immunopharmacol.*, 21:647-662, 1999.
Wang et al., "Airway epithelia regulate expression of human beta-defensin 2 through Toll-like receptor 2," *FASEB J.*, 17:1727-1729, 2003.
Wang et al., "Novel cytoplasmic proteins of nontypeable Haemophilus influenzae up-regulate human MUC5AC mucin transcription via a positive p38 mitogen-activated protein kinase pathway and a negative phosphoinositide 3-kinase-Akt pathway," *J. Biol. Chem.*, 277:949-957, 2002.
Weiser & Pan, "Adaption of Haemophilus influenzae to acquired and innate humoral immunity based on phase variation of lipopolysaccharide," *Mol. Microbiol.*, 30:767-775, 1998.
Williams et al., "Airway mucus: From production to secretion," *Am. J. Respir. Cell Mol. Biol.*, 34(5):527-36. 10, 2006.
Yamamoto et al., "Role of adaptor TRIF in the MyD88-independent toll-like receptor signaling pathway," *Science*, 301:640-643, 2003.
Young et al., "A3 adenosine receptor signaling contributes to airway mucin secretion after allergen challenge," *Am. J. Respir. Cell Mol. Biol.*, 35:549-558, 2006.
Young et al., "Central Role of Muc5ac Expression in Mucous Metaplasia and Its Regulation by Conserved 5' Elements," *Am. J. Respir. Cell Mol. Biol.*, 37:273-290, 2007.
Zhen et al., "IL-13 and epidermal growth factor receptor have critical but distinct roles in epithelial cell mucin production," *Am. J. Respir. Cell Mol. Biol.*, 36:244-253, 2007.
Agrawal & Kandimalla, "Synthetic agonists of Toll-like receptors 7, 8 and 9", Biochemical Society Transactions, 2007, vol. 35, No. 6, pp. 1461-1467.
Hartmann et al., "Delineation of a CpG Phosphorothioate Oligodeoxynucleotide for Activating Primate Immune Responses In Vitro and In Vivo", The Journal of Immunology, 2000, vol. 164, pp. 1617-1624.
Hartmann et al., "Rational design of new CpG oligonucleotides that combine B cell activation with high IFN-alpha induction in plasmacytoid dendritic cells", Eur. J. Immunol. 2003, vol. 33, pp. 1633-1641.
Jurk et al., "C-Class CpG ODN: sequence requirements and characterization of immunostimulatory activities on mRNA level", Immunobiology, 2004, vol. 209, pp. 141-154.
Krieg et al., "CpG motifs in bacterial DNA trigger direct B-cell activation", Letters to Nature, vol. 374, pp. 546-549, Apr. 6, 1995.
Krieg, "Antiinfective Applications of Toll-like Receptor 9 Agonists", Proceedings of the American Thoracic Society, vol. 4, pp. 289-297, 2007.
Krieg, "Therapeutic potential of Toll-like receptor 9 activation", Nature Reviews, vol. 5, pp. 471-484, Jun. 2006.
McHutchison et al., "Phase 1B, Randomized, Double-Blind, Dose-Escalation Trial of CPG 10101 in Patients with Chronic Hepatitis C Virus", Hepatology 2007, vol. 46, No. 5, pp. 1341-1349.
Office Action issued in Chinese Patent Application No. 201080022634.7, dated Aug. 20, 2012.
Platz et al., "Microbial DNA Induces a Host Defense Reaction of Human Respiratory Epithelial Cells", The Journal of Immunology, 2004, vol. 173, pp. 1219-1223.
Vollmer et al., "Characterization of three CpG oligodeoxynucleotide classes with distinct immunostimulatory activities", Eur. J. Immunol., 2004, vol. 34, pp. 251-262.
Vollmer & Krieg, "Immunotherapeutic applications of CpG oligodeoxynucleotide TLR9 agonists" Advanced Drug Delivery Reviews, 2009, vol. 61, pp. 195-204.
Kimbrell, et al., "Comparison of the Immunostimulatory and Proinflammatory Activities of Candidate Gram-Positive Endotoxins,

(56) References Cited

OTHER PUBLICATIONS

Lipoteichoic Acid, Peptidoglycan, and Lipopeptides in Murine and Human Cells", Immunol. Lett., 2008; 118(2): 132-141.

Krishnan et al., "Toll-Like Receptor Signal Transduction," Experimental and Molecular Medicine, Aug. 2007, vol. 39, No. 4, pp. 421-438.

Xingkui, et al. "Immunostimulatory characteristics and applications of CpG oligodeoxynucleotides" *Progress in Veterinary Medicine*, 2008, 29(7): 71-75. (English Abstract).

Bergmann and Schwarting, "Application of a polyvalent bacterial lusat as aerosol in patients with recurrent airway infections without detectable side effects," *Allergologie, Jabrgang*, 10:455-458, 1987 (German with English abstract).

* cited by examiner

Swiss-Webster mice challenged with *P. aeruginosa* ($2 \times 10^{10}$ CFU/ml)

Expt. 3 Effect of One 30-min Aerosol Pretreatment (D-1) with ODN/Pam2/PolyIC on Survival of Mice Infected with Influenza A/HK Aerosol; Virus Dose: ~130 $TCID_{50}$/mouse

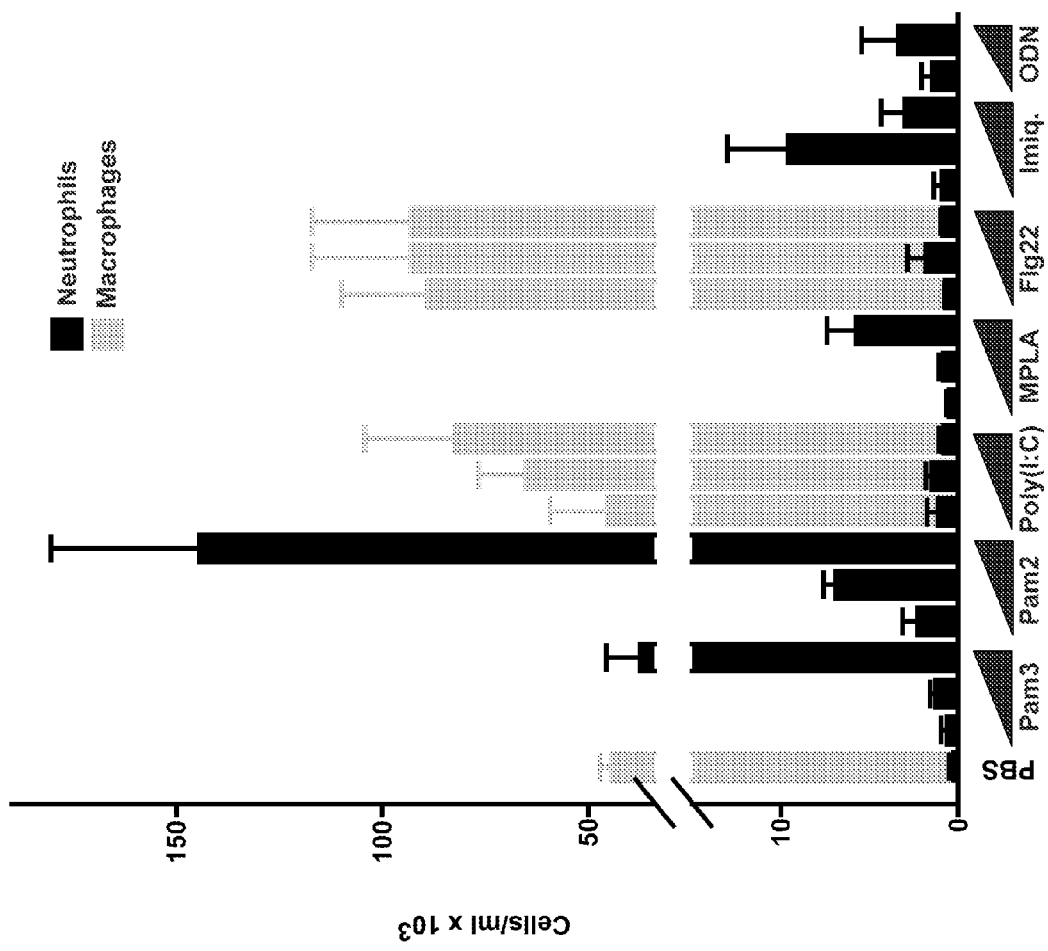

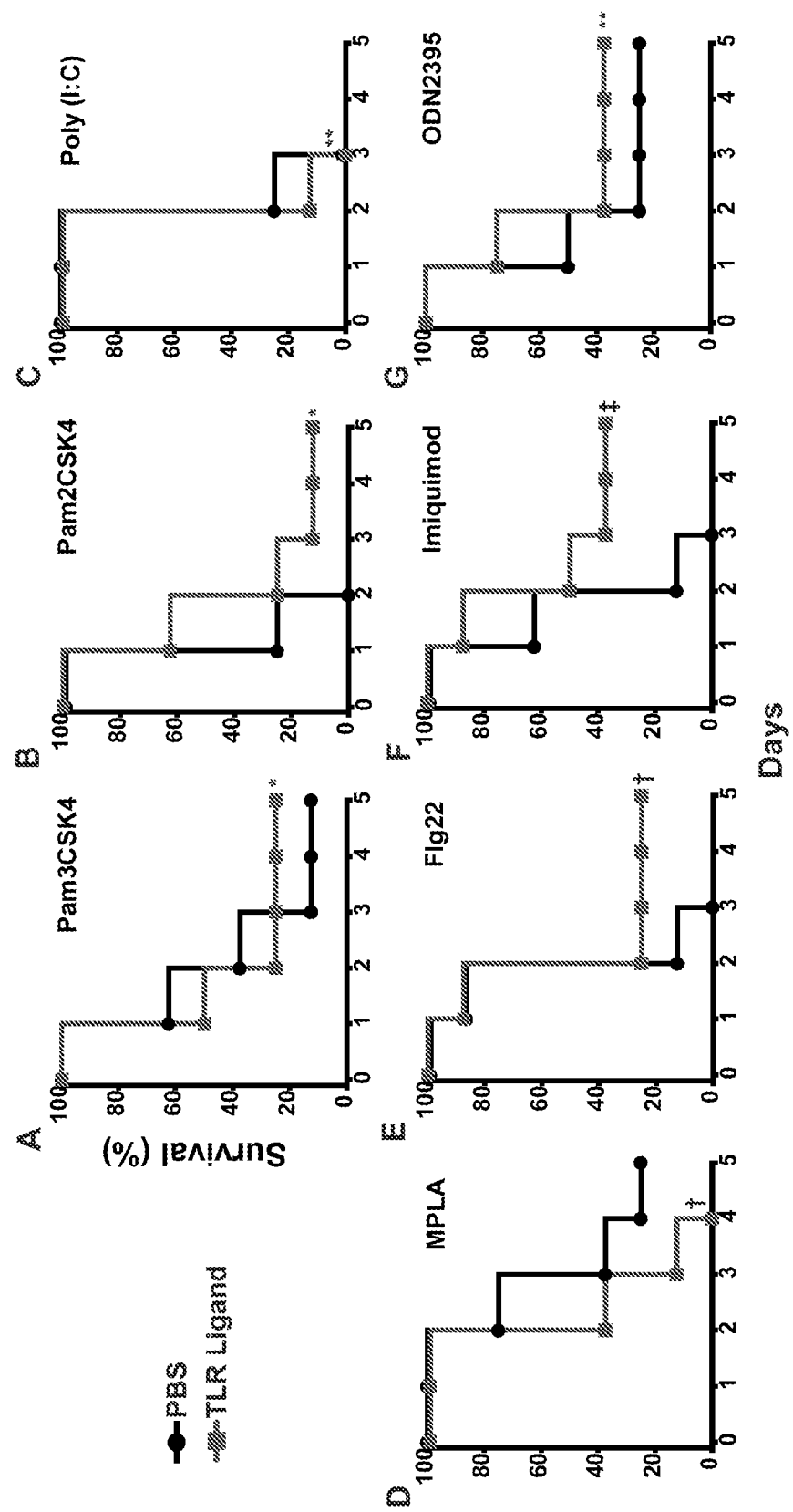
FIG. 15A-G

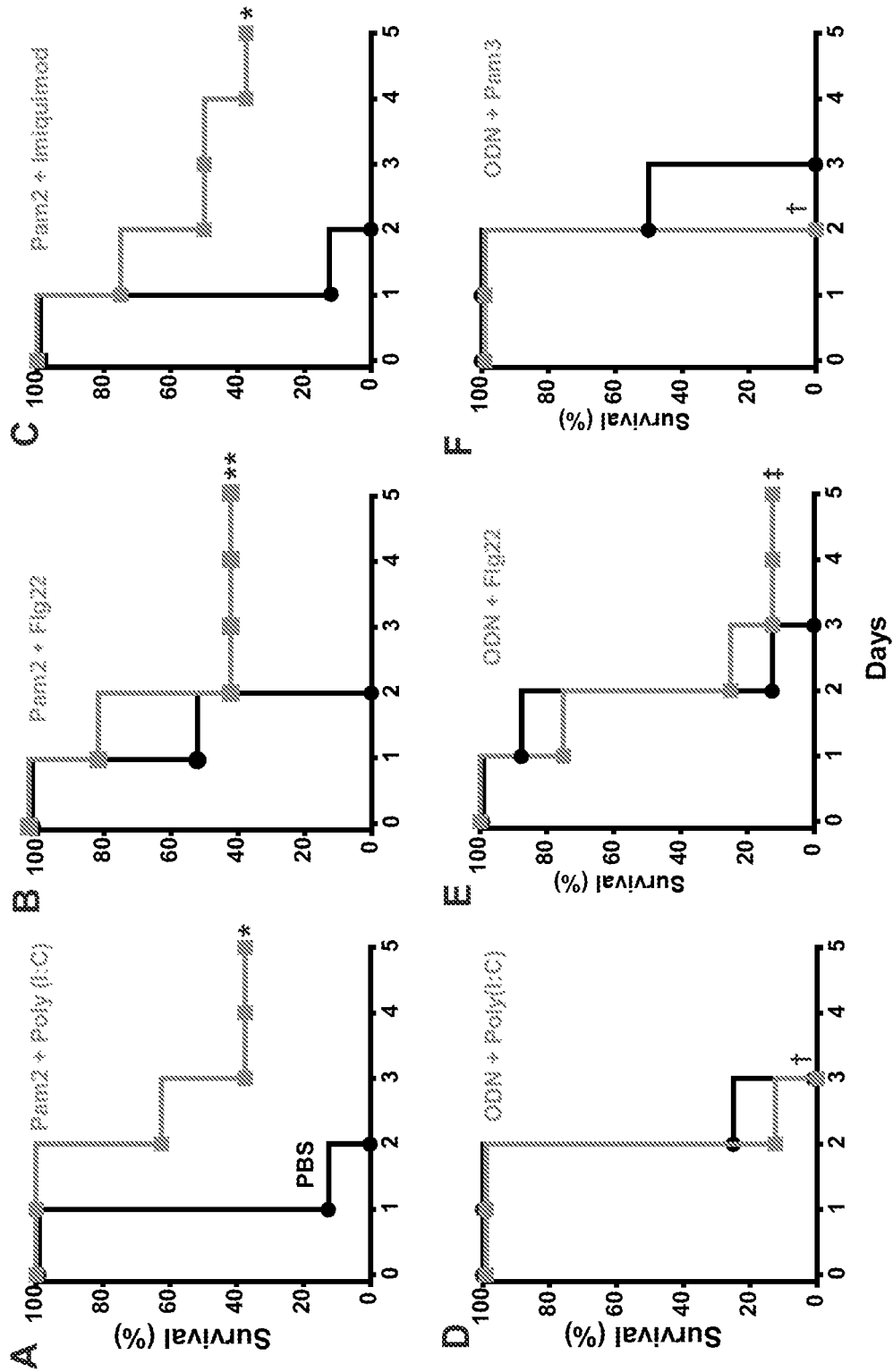
FIGS. 17A-F

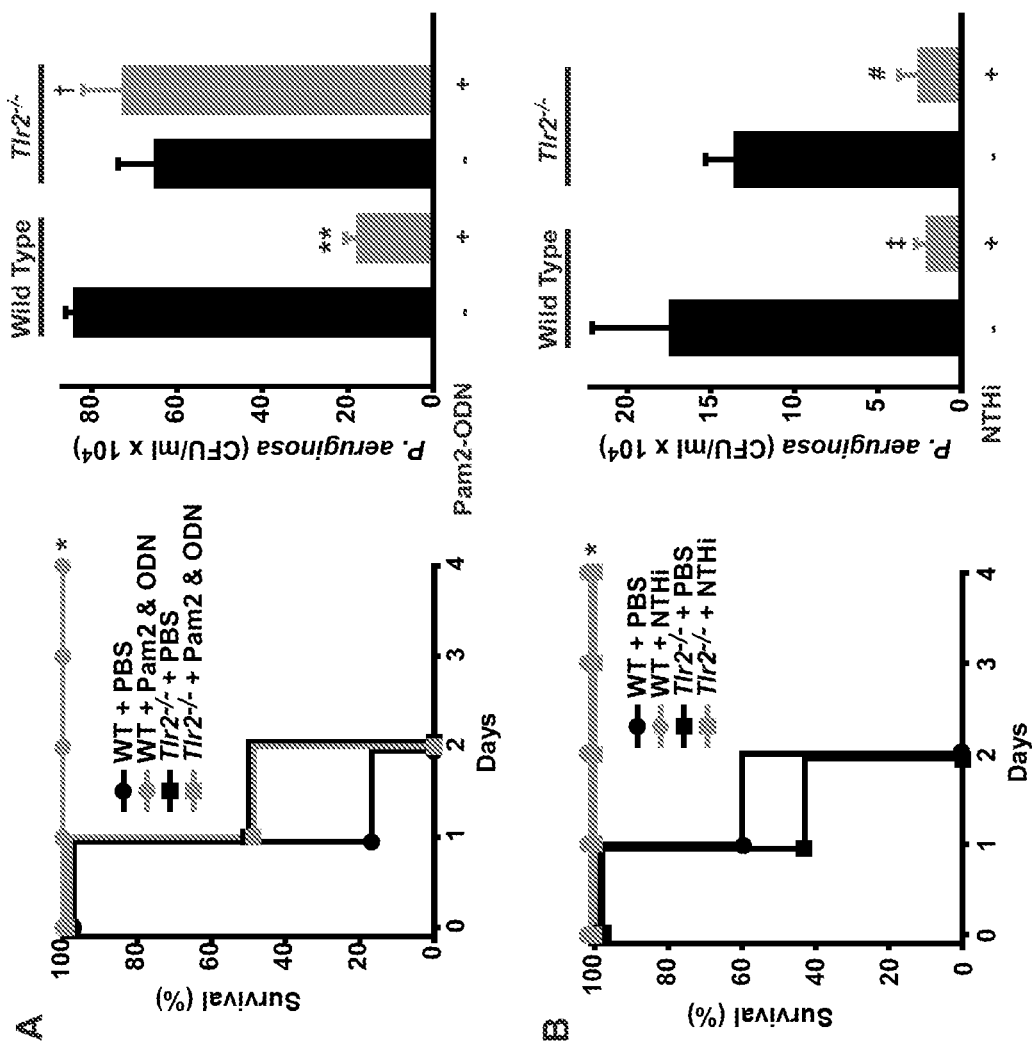
FIGS. 18A-B

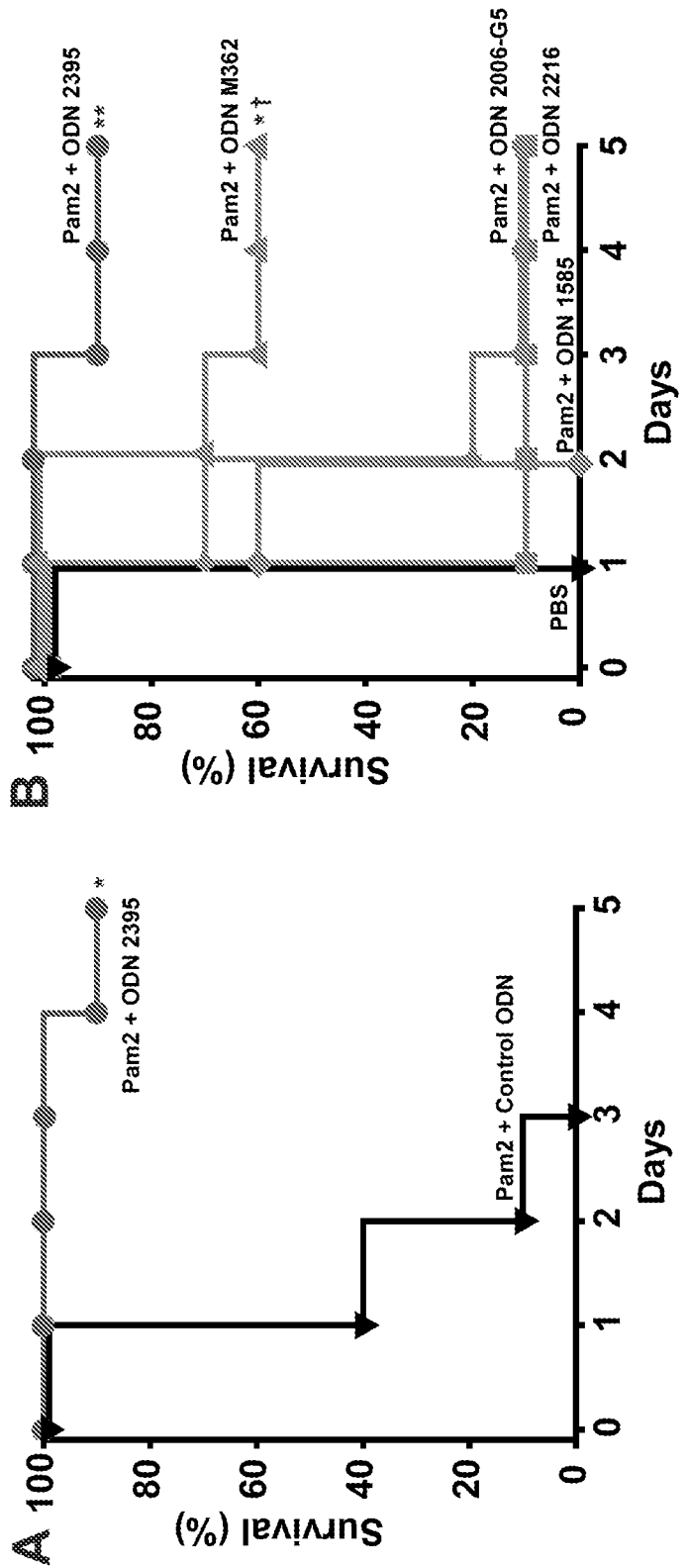
FIGS. 19A-B

FIGS. 20A-D
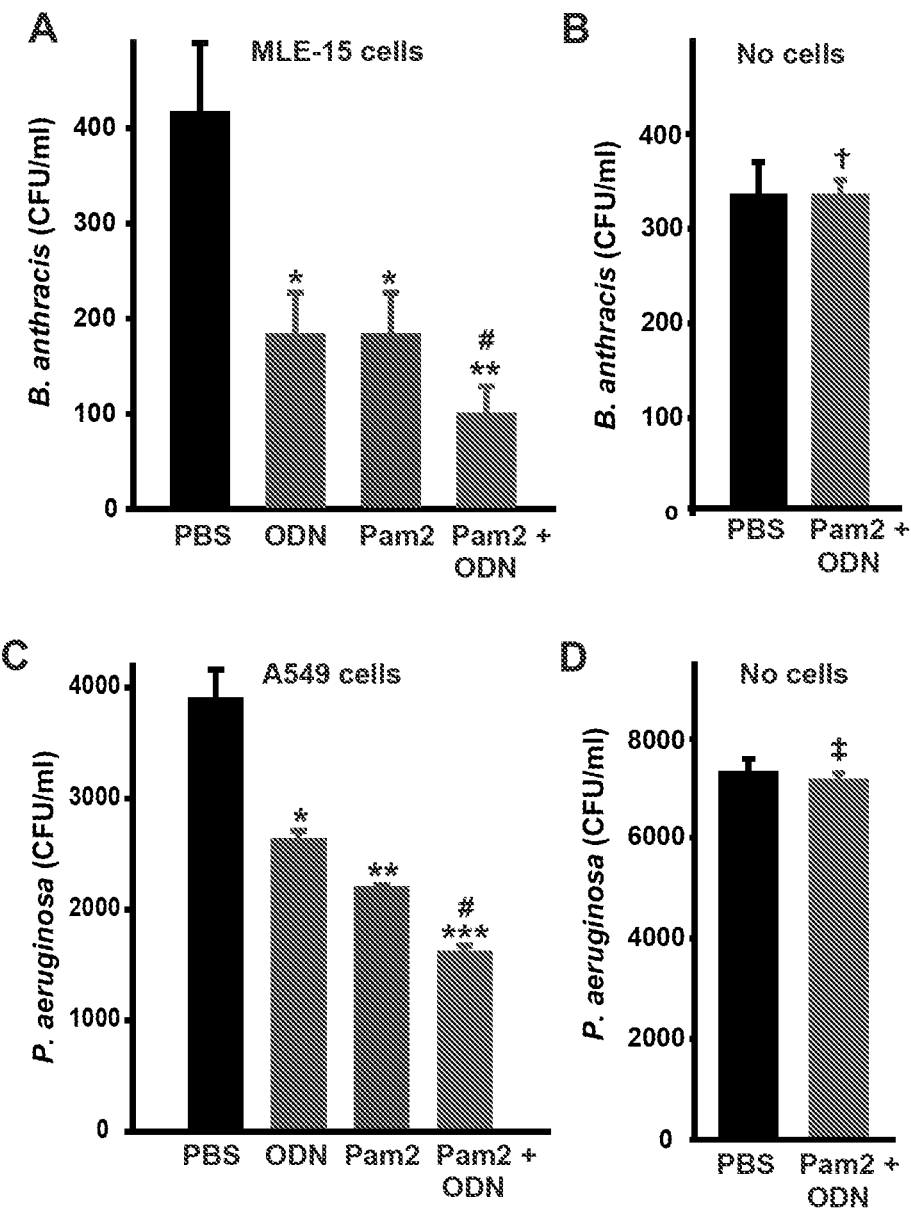

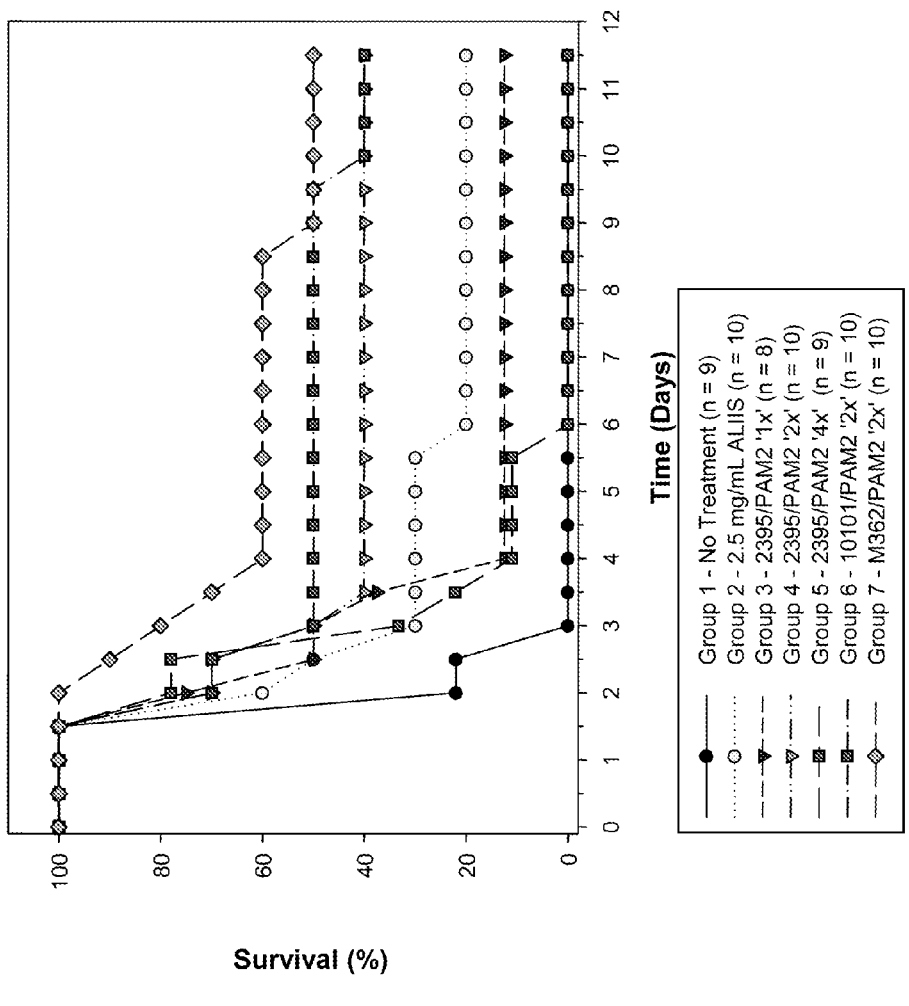

FIG. 22

Effect of Aerosol Pretreatment with ODNs/Pam2 or NTHi Lysate on Survival of Influenza A/HK-infected Mice

COMPOSITIONS FOR STIMULATION OF MAMMALIAN INNATE IMMUNE RESISTANCE TO PATHOGENS

This application is a divisional of U.S. patent application Ser. No. 13/259,761 filed Dec. 14, 2011, now U.S. Pat. No. 8,883,174 which is a national phase application under 35 U.S.C. §371 of International Application No. PCT/US2010/028658 filed Mar. 25, 2010, which claims priority to U.S. Provisional Patent Application Ser. No. 61/163,137 filed Mar. 25, 2009, and U.S. Provisional Patent Application Ser. No. 61/179,246 filed May 18, 2009, each of which is incorporated herein by reference in their entirely.

BACKGROUND OF THE INVENTION

I. Field of the Invention

The present invention relates generally to the fields of microbiology, immunology, and antimicrobial pharmacotherapy. More particularly the compositions and methods of the invention relate to modulation of innate immunity in the lungs of an individual for the treatment or attenuation of microbial infection or invasion using small molecule compositions.

II. Background

The susceptibility of the lungs to infection arises from the architectural requirements of gas exchange. To support ventilation, humans continuously expose 100 $m^2$ lung surface area to the external environment. Lungs are exposed not only to air, but also to the particles, droplets, and pathogens that are suspended within it. Unlike cutaneous surfaces that are wrapped in impermeable skin or the gastrointestinal tract with a thick adsorbent blanket of mucus, the lungs present a large environmental interface with a minimal barrier defense. A more substantial barrier is precluded by the demand for unimpeded gaseous diffusion.

Despite their structural vulnerability, the lungs generally defend themselves successfully against infection through a variety of mechanical, humoral, and cellular mechanisms (Knowles et al., 2002; Martin and Frevert, 2005; Rogan, et al., 2006; Travis, et al., 2001); (Mizgerd, 2008; Bals and Hiemstra, 2004; Bartlett et al., 2008; Hiemstra, 2007; Hippenstiel et al., 2006; Schutte and McCray, 2002). Most inhaled microbial pathogens fail to penetrate to the alveoli due to impaction against the airway walls, where they are entrapped by mucus and then expelled via the mucociliary escalator system (Knowles et al., 2002). For those pathogens that escape this fate, the constitutive presence of antimicrobial peptides in the airway lining fluid limits their growth (Rogan, et al., 2006; Travis, et al., 2001). Alveolar macrophages that reside in the most distal airspaces are able to ingest these organisms, thereby clearing the lungs from a potential infection.

Though often regarded as passive gas exchange barriers, the airway and alveolar epithelia supplement the baseline lung defenses by undergoing remarkable local structural and functional changes when pathogenic stimuli are encountered. In response to viral, fungal, or allergic inflammation, airway secretory cells rapidly increase their height and fill their apical cytoplasm with secretory granules, a process termed inflammatory metaplasia (Evans et al., 2004; Williams et al., 2006). In the presence of pathogens, the alveolar epithelia activate their plasmalemmal systems and secretory machinery, thereby engaging leukocytes in lung protection (Evans et al., 2005). Perhaps most importantly, microbial interactions with respiratory epithelial pattern recognition receptors causes numerous microbicidal products to be expressed into the airway lining fluid, including defensins, cathelicidins, lysozyme, and reactive oxygen species (Rogan et al., 2006; Forteza et al., 2005; Akinbi et al., 2000; Bals and Hiemstra, 2004; Bals and Hiemstra, 2006). It is of note that pneumonia (bacterial or viral) is the leading cause of death from infection worldwide.

There is a need for additional methods and compositions for inhibiting and/or treating microbial infections.

SUMMARY OF THE INVENTION

The present invention provides compositions that stimulate innate resistance, (Stimulated Innate Resistance (StIR)) and methods of using such compositions to stimulate StIR. In certain embodiments StIR is lung StIR. One aspect of the invention provides for a higher therapeutic/toxicity ratio or index. Embodiments of the invention include compositions, formulations, and methods for the enhancement of a mammalian, e.g., a human, subject's biological defenses against infection, for example, the subject's immunity against infection. In certain aspects compositions of the invention are deposited in an effective amount in the lungs of an individual. Aspects of the invention provide a rapid and temporal enhancement or augmentation of biological defenses against microbial infection. The enhancement of the immunity of a subject attenuates microbial infections. Attenuation can be by inhibiting, treating, or preventing infection or microbial growth or survival. Aspects of the invention enhance the defenses of the lung and respiratory tract of a subject.

In certain aspects, methods of treating, inhibiting or attenuating a microbial infection in an individual who has or is at risk for developing such an infection is contemplated, the methods comprising administering an effective amount of a StIR composition comprising one or more ligands for one or more innate receptors. A number of innate receptors have been identified as including, but not limited to, Toll-like receptor (TLR), C-type lectin receptors (CLRs), and nucleotide-binding oligomerization domain-like receptors (Nod-like receptors or NLRs). TLRs are a class of proteins that play a key role in the innate immune system. They are single membrane-spanning non-catalytic receptors that recognize structurally conserved molecules derived from microbes. Once these microbes are present on or in the skin or intestinal tract, lung, and genitorurinary mucosa, they are recognized by TLRs, which activates immune cell responses. Interestingly, many of these TLR agonists do not induce a signficant StIR when administered alone. Typically, an individual or subject being treated using the methods described herein has been exposed to a pathogenic microbe or is at risk for such exposure.

Certain embodiments are directed to compositions capable of being administered to the respiratory tract comprising 1, 2, 3, 4, or more TLR agonists, as well as methods using such compositions. The TLR agonists are selected from TLR2/1, TLR2/6, TLR3, TLR4, TLR5, TLR9, or TLR7 agonist. In certain aspects the TLR agonists are selected from TLR9 and TLR2/6 agonist. In a further aspect the TLR agonists are selected from TLR5 agonist. In still a further aspect a TLR5 agonist can be used in combination with a TLR2/6, TLR4, TLR9, or TLR7 agonist. In certain aspects a TLR9 agonist can be used in combination with a TLR2/6, TLR4, TLR5, or TLR7. In another aspect a TLR2/6 agonist can be used in combination with a TLR4, TLR5, TLR9, or TLR7 agonist. In certain aspects a TLR4 agonist can be used in combination with a TLR2/6, TLR5, TLR9, or TLR7 agonist. In a further aspect a TLR7 agonist can be used in combination with a TLR2/6, TLR4, TLR5, or TLR9 agonist. In still a further aspect any of these double combinations can include a third or a fourth or a fifth TLR agonist selected from a TLR2/6, TLR4, TLR5, TLR9, or TLR7 agonist.

Certain embodiments are directed to methods of treating, inhibiting, or attenuating a microbial infection comprising administering an effective amount of a TLR9 agonist and a TLR2/6 agonist to an individual that has or is at risk of developing or acquiring a microbial infection. In certain aspects the TLR2/6 agonist is PAM2CSK4. In a further aspect the TLR9 agonist is a type C oligodeoxynucleotide (ODN). The type C ODN can include, but is not limited to ODN2395 or ODNM362 or ODN10101 or another type C ODN or analog thereof. In certain aspects the subject has been exposed to or is at risk of exposure to a pathogenic microbe. The microbe can be a virus, a bacteria, or a fungus.

In other aspects the TLR9 agonist and the TLR2/6 agonist are administered in a nebulized formulation. The TLR9 agonist and/or the TLR2/6 agonist can be administered in an amount from about 0.1, 1, 5, 10, 50 μg or mg/kg to about 5, 10, 50, 100 μg or mg/kg of the individual's body weight, including all values and ranges there between.

Certain embodiments are directed to a pharmaceutically acceptable composition comprising a TLR9 agonist and a TLR2/6 agonist, an anti-inflammatory agent, and one or more pharmaceutical excipients, wherein said composition is sterile and essentially free of pathogenic microbes. In certain aspects the TLR2/6 agonist is PAM2CSK4. In a further aspect the TLR9 agonist is a type C oligodeoxynucleotide (ODN). The type C ODN can include, but is not limited to ODN2395 or ODNM362 or ODN10101.

In certain aspects the StIR composition comprises a flagellin polypeptide comprising 10, 11, 12, 13, 14, 15, 16, 17, 18, 19, 20, 21, or 22 consecutive amino acids of the peptide QRLSTGSRINSAKDDAAGLQIA (SEQ ID NO:2), which is known as a TLR5 agonist, or a segment or derivative thereof. A polypeptide of the invention can also comprise an amino acid sequence that is at least 70, 80, or 90%, including all values and ranges there between, identical to SEQ ID NO:2. In other aspects, flagellin is a synthesized and/or a purified or isolated flagellin polypeptide or peptide. The term "purified" or "isolated" means that component was previously isolated away or purified from other proteins or synthesis reagents or by-products, and that the component is at least about 95% pure prior to being formulated in the composition. In certain embodiments, the purified or isolated component is about or is at least about 80, 95, 96, 97, 98, 99, 99.1, 99.2, 99.3, 99.4, 99.5% or more pure, or any range derivable therein. Such a purified component may then be mixed with other components to form a composition as described herein.

A recombinant flagellin protein or fragment or segment thereof comprises 5, 10, 15, 20, 21, 22, 23, 24, 25, 30, 35, 40, 50, 55, 60, 65, 70, 75, 80, 85, 90, 95, 100, 150, 200, 250, 300, 350, or 400 consecutive amino acids, including all values and ranges there between, of SEQ ID NO:2 or other flagellin polypeptides. These fragments or segments are at least, at most, or about 70, 75, 80, 85, 90, 95, 96, 97, 98, 99 or 100% identical to SEQ ID NO:2 or other falgellin polypetides. In certain aspects, a flagellin polypeptide or segment is at least 75% identical to the sequence of SEQ ID NO:2. In another aspect, the flagellin polypeptide or segment is at least 80% identical to the sequence of SEQ ID NO:2. In another aspect, the flagellin polypeptide or segment is at least 85% identical to the sequence of SEQ ID NO:2. In another aspect, the flagellin polypeptide or segment is at least 90% identical to the sequence of SEQ ID NO:2. In another aspect, the flagellin polypeptide or segment is at least 95% identical to the sequence of SEQ ID NO:2. Derivatives or variants of flagellin or its segments includes insertion, deletion, and point mutations of SEQ ID NO:2. A particular insertional mutation is a fusion protein that comprises amino acid sequence exogenous to flagellin at the carboxy or amino terminus. A number of flagellin proteins are known in the art and include, but are not limited to a flagellin having accession number BAB58984 (gi|14278896); YP_001330159 (gi|150402865); YP_001323483 (gi|150399716); CAA28975 (gi|1333716); CAA02137 (gi|1567895); CAA67105 (gi|1580779); AAR10473 (gi|38049688); CAR58992 (gi|197093531); YP_001217666 (gi|147675484); CAL12564 (gi|122089712); BAD14977 (gi|46093563); or CAD05707 (gi|16503200), each of which is incorporated herein by reference in its entirety as of the priority date of this application.

Embodiments of the invention can be administered via the respiratory tract. Methods of the invention include the administration of a composition by inhalation or other methods of administration to the upper and/or lower respiratory tract. In certain aspects administration is by inhalation. In certain aspects, the StIR composition is administered in a nebulized or aerosolized formulation. In a further aspect the composition is aerosolized or nebulized or in a form that can be inhaled by or instilled in a subject. The composition can be administered by inhalation or inspiration. The StIR composition, including TLR agonist individually or in aggregate, can be administered in an amount of from about 0.01, 0.05. 0.1, 0.5, 1, 5, 10, 15, 20, 25, 30, 35, 40, 45, 50, 55, 60, 65, 70 μg or mg/kg to about 55, 60, 65, 70, 75, 80, 85, 90, 95, 100, 125, 150, 200 μg or mg/kg of the individual's body weight. In other aspects, a subject can be administered about 0.01, 0.05. 0.1, 0.5, 1, 5, 10, 15, 20, 25, 30, 35, 40, 45, 50, 55, 60, 65, 70, 75, 80, 85, 90, 95, 100, 125, 150, 200 μg or mg of StIR or TLR agonist individually or all TLR agonists total. The subject can be at risk of exposure to or exposed to an inhaled virus, bacteria, or fungus. Still further embodiments include methods where the composition is administered before; after; during; before and after; before and during; during and after; before, after and during exposure or suspected exposure or heightened risk of exposure to the organism. The subject can be exposed to a bioweapon or to an opportunistic pathogen. In particular aspects the subject is immunocompromised, such as a cancer patient or an AIDS patient.

In yet another embodiment, the present invention is directed to a pharmaceutically acceptable composition comprising one or more TLR agonists; an anti-inflammatory agent; an anti-microbial agent; and/or one or more pharmaceutical excipients. Typically such compositions are sterile and essentially free of pathogenic microbes.

In certain aspects the pathogenic or potentially pathogenic microbe being treated or protected against is a virus, a bacteria, and/or a fungus. In certain aspects, a microbe is a virus. The virus can be from the Adenoviridae, Coronaviridae, Filoviridae, Flaviviridae, Hepadnaviridae, Herpesviridae, Orthomyxoviridae, Paramyxovirinae, Pneumovirinae, Picornaviridae, Poxyiridae, Retroviridae, or Togaviridae family of viruses; and/or Parainfluenza, Influenza, H5N1, Marburg, Ebola, Severe acute respiratory syndrome coronavirus, Yellow fever virus, Human respiratory syncytial virus, Hantavirus, or Vaccinia virus.

In yet a further aspect, the pathogenic or potentially pathogenic microbe being treated or protected against is a bacteria. A bacteria can be an intracellular, a gram positive, or a gram negative bacteria. In a further aspect, the bacteria includes, but is not limited to a *Staphylococcus*, a *Bacillus*, a *Francisella*, or a *Yersinia* bacteria. In still a further aspect, the bacteria is *Bacillus anthracis, Yersinia pestis, Francisella tularensis, Pseudomonas aerugenosa*, or *Staphylococcus aureas*. In certain embodiments, a bacteria is *Bacillus anthra-* cis and/or *Staphylococcus aureas*. In still a further aspect, a bacteria is a drug resistant bacteria, such as a multiple drug resistant *Staphylococcus aureas* (MRSA). Representative medically relevant Gram-negative bacilli include *Hemophilus influenzae, Klebsiella pneumoniae, Legionella pneumophila, Pseudomonas aeruginosa, Escherichia coli, Proteus mirabilis, Enterobacter cloacae, Serratia marcescens, Helicobacter pylori, Salmonella enteritidis*, and *Salmonella typhi*. Representative gram positive bacteria include, but are not limited to *Bacillus, Listeria, Staphylococcus, Streptococcus, Enterococcus, Actinobacteria* and *Clostridium Mycoplasma* that lack cell walls and cannot be Gram stained, including those bacteria that are derived from such forms.

In still anther aspect, the pathogenic or potentially pathogenic microbe being treated or protected against is a fungus, such as members of the family *Aspergillus, Candida, Crytpococus, Histoplasma, Coccidioides, Blastomyces, Pneumocystis*, or *Zygomyces*. In still further embodiments a fungus includes, but is not limited to *Aspergillus fumigatus, Candida albicans, Cryptococcus neoformans, Histoplasma capsulatum, Coccidioides immitis*, or *Pneumocystis carinii*. The family zygomycetes includes Basidiobolales (Basidiobolaceae), Dimargaritales (Dimargaritaceae), Endogonales (Endogonaceae), Entomophthorales (Ancylistaceae, Completoriaceae, Entomophthoraceae, Meristacraceae, Neozygitaceae), Kickxellales (Kickxellaceae), Mortierellales (Mortierellaceae), Mucorales, and Zoopagales. The family *Aspergillus* includes, but is not limited to *Aspergillus caesiellus, A. candidus, A. carneus, A. clavatus, A. deflectus, A. flavus, A. fumigatus, A. glaucus, A. nidulans, A. niger, A. ochraceus, A. oryzae, A. parasiticus, A. penicilloides, A. restrictus, A. sojae, A. sydowii, A. tamari, A. terreus, A. ustus, A. versicolor*, and the like. The family *Candida* includes, but is not limited to *Candida albicans, C. dubliniensis, C. glabrata, C. guilliermondii, C. kefyr, C. krusei, C. lusitaniae, C. milleri, C. oleophila, C. parapsilosis, C. tropicalis, C. utilis*, and the like.

In certain aspects the pathogenic bacteria is an intracellular, a gram positive, or a gram negative bacterium. In certain embodiments the bacteria is a *Streptococcus, Staphylococcus, Bacillus, Francisella*, or *Yersinia*. In still further aspects the bacteria is *Bacillus anthracis, Yersinia pestis, Francisella tularensis, Streptococcus pnemoniae, Staphylococcus aureas, Pseudomonas aeruginosa*, and/or *Burkholderia cepacia*.

The terms "attenuating," "inhibiting," "reducing," or "prevention," or any variation of these terms, when used in the claims and/or the specification includes any measurable decrease or complete inhibition to achieve a desired result, e.g., reduction in post-exposure microbe load or growth.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed herein can be implemented with respect to any method or composition of the invention, and vice versa. Furthermore, compositions and kits of the invention can be used to achieve methods of the invention.

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or." In certain list including and/or, or, or and one or more of the listed members can be specifically excluded from the list.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 10. Illustrates the effect of one 30-min aerosol pre-treatment with ODN/PAM2/PolyIC on survival of mice infected with influenza A/HK aerosol; viral dose ~130 $TCID_{50}$/mouse.

FIG. 12A. $Myd88^{-/-}$ and wild type mice were inhalationally challenged with *P. aeruginosa* with or without pretreatment 24 h earlier with an aerosolized lysate of nontypeable *H. influenzae* (NTHi). Left, survival (N=10 mice/group, *p<0.0001). Right, bacterial lung burden immediately after infection (right, N=3 mice/group, **p<0.004, †p=0.39 vs. wild type control). FIG. 12B. *P. aeruginosa* challenge of $Trif^{-/-}$ mice with or without pretreatment with the bacterial lysate. Left, survival (N=10 mice/group, *p<0.0001). Right, bacterial lung burden immediately after infection (N=3 mice/group, *p<0.0001).

FIG. 14. Leukocyte counts in bronchoalveolar lavage fluid after treatment with single synthetic TLR ligands. Mice were submitted to BAL 24 h after treatment with PBS or one of the following TLR ligands: Pam3CSK4 (TLR2/1 agonist, 1 µg/ml, 3 µg/ml, 10 µg/ml), Pam2CSK4 (TLR2/6 agonist, 1 µg/ml, 3 µg/ml, 10 µg/ml), Poly(I:C) (TLR3 agonist, 1 µg/ml, 10 µg/ml, 100 µg/ml), synthetic lipid A (MPLA, TLR4 agonist, 1 µg/ml, 10 µg/ml, 100 µg/ml), Flg22 (synthetic 22-mer of flagellin, TLR5 agonist, 10 µg/ml, 100 µg/ml, 1000 µg/ml), imiquimod (TLR7 and TLR8, 100 µg/ml, 300 µg/ml, 1000 µg/ml), or ODN2395 (TLR9 agonist, 2 µg/ml, 20 µg/ml). Shown are neutrophil (black bars) and macrophage (gray bars) counts in BAL fluid.

FIGS. 15A-15G. Aerosolized treatment with individual synthetic TLR ligands does not induce a high level of resistance against pneumonia. Wild type mice were challenged with *P. aeruginosa* after treatment (8 ml nebulized over 20 min) with PBS or the following synthetic TLR ligands 24 h prior: FIG. 15A. TLR2/1 agonist Pam3CSK4 100 µg/ml, FIG. 15B. TLR2/6 agonist Pam2CSK4 10 µg/ml, FIG. 15C. TLR3 agonist poly (I:C) 100 µg/ml, FIG. 15D. TLR4 agonist MPLA 100 µg/ml, FIG. 15E. TLR5 agonist Flg22 100 µg/ml, FIG. 15F. TLR7 and TLR8 agonist imiquimod 1 mg/ml, or FIG. 15G. TLR9 agonist ODN 2395 20 µg/ml. Survival curves are representative examples of at least three distinct experiments for treated and untreated mice (N=8 mice/group, *p=0.5, **p=1.0, †p=0.47, ‡p=0.2).

FIG. 16A. Left, survival of mice challenged with *P. aeruginosa* 24 h after treatment with PBS, Pam2CSK4 10 µg/ml, ODN 2395 20 µg/ml, the combination, or the combination at double dose (N=6 mice/group, ‡p=0.008 vs. PBS). Right, Bacterial burden of lung homogenates immediately after infection with *P. aeruginosa* (N=3 mice/group, #p=0.045 vs. PBS, ##p=0.030 vs. PBS). FIG. 16B. Left, survival of mice challenged with *S. pneumoniae* 24 h after treatment with PBS, Pam2CSK4 10 µg/ml, ODN 2395 20 µg/ml, the combination, or the combination at double dose (N=10 mice/group, ‡p<0.0001 vs. PBS treated). Right, bacterial burden of lung homogenates immediately after *S. pneumoniae* infection $2\times10^{10}$ (N=3 mice/group, †p<0.001, ‡p<0.0001). FIG. 16C. BAL cell counts from mice 4 or 24 h after treatment with PBS, Pam2CSK4 10 µg/ml, ODN 2395 20 µg/ml, or the combination of Pam2CSK4 and ODN2395 (N=3 mice/group, *p=0.016 vs. PBS, **p<0.0001 vs. PBS, †p=0.041 vs. Pam2 alone).

FIGS. 17A-17F. Not all TLR agonist combinations provide signifcant protection against pneumonia. Wild type mice were challenged with *P. aeruginosa* following treatment with PBS or the following TLR agonist combinations 24 h prior: FIG. 17A. Pam2CSK4 and poly (I:C), FIG. 17B. Pam2CSK4 and Flg22, FIG. 17C. Pam2CSK4 and imiquimod, FIG. 17D. ODN2395 and poly (I:C), FIG. 17E. ODN2395 and Flg22, FIG. 17F. ODN2395 and Pam3CSK4. Survival curves are representative examples of at least three distinct experiments (N=8 mice/group, *p=0.20, **p=0.08, †p=1.0, ‡p=0.5).

FIGS. 18A-18B. TLR2 is sufficient to promote protective Pam2CSK4 and ODN2395 synergy, but is not required for induced resistance. FIG. 18A. Left, survival of $Tlr2^{-/-}$ and wild type mice challenged with *P. aeruginosa* with or without ODN2395 and Pam2CSK4 treatment 24 h prior (N=8 mice/group, *p<0.0002). Right, Bacterial burden of lung homogenates immediately after infection with *P. aeruginosa* (N=4 mice/group, **p<0.0001 vs. wild type+PBS, †p=0.59 vs. $Tlr2^{-/-}$ +PBS) FIG. 18B. Left, survival of $TLR2^{-/-}$ and wild type mice challenged with *P. aeruginosa* with or without treatment 24 h prior with an aerosolized lysate of nontypeable *H. influenzae* (NTHi) (N=10 mice/group, *p<0.0002). Right, Bacterial burden of lung homogenates immediately after infection with *P. aeruginosa* (N=3 mice/group, ‡p=0.03 vs. wild type+PBS, #p=0.002 vs. $Tlr2^{-/-}$ +PBS).

FIGS. 19A-19B. TLR9-binding Class C, but not Class A or B, CpG ODNs interact synergistically with Pam2CSK4 to induce resistance to bacterial pneumonia. FIG. 19A. Survival of wild type mice treated with Pam2CSK4 and ODN2395 or Pam2CSK4 and a scrambled control ODN 24 h prior to *P. aeruginosa* challenge (N=10 mice/group, *p<0.0001). FIG. 19B. Survival of wild type mice challenged with *P. aeruginosa* 24 h after treatment with PBS or Pam2CSK4 combined with a Class A CpG ODN (ODN1585 or ODN2216), a Class B CpG ODN (ODN 2006-G5) or a Class C CpG ODN (M362 or ODN2395) (N=10 mice/group, *p=0.01 vs. PBS, **p=0.0001 vs. PBS; †p=0.3 vs. Pam2+ODN2395).

FIGS. 20A-20D. TLR2/6 and TLR9 agonists cooperate to induce bacterial killing by murine and human respiratory epithelial cells in vitro. FIG. 20A. MLE-15 cells were treated with Pam2CSK4 (10 µg/ml) and/or ODN2395 (20 µg/ml) for 4 h prior to infection with *B. anthracis* (1000 spores). Shown are bacterial CFU 4 h after infection (*p=0.05 vs. PBS, **p=0.016 vs. PBS, #p>0.05 vs. either single agonist). FIG. 20B. MLE culture media (without cells) was treated with ODN2395 and Pam2CSK4, infected with *B. anthracis* (1000 spores), and cultured after 4 h (†p=1.0). FIG. 20C. A549 cells were treated with ODN2395 and Pam2CSK4 for 4 h prior to infection with *P. aeruginosa* (2700 CFU). Shown are bacterial CFU 4 h after infection (*p=0.01 vs. PBS, p=0.003 vs. PBS, *p=0.001 vs. PBS, #p=>0.05 vs. either single agonist). FIG. 20D. MLE culture media (without cells) was treated with ODN2395 and Pam2CSK4, infected with *P. aeruginosa* (4000 CFU), and cultured after 4 h (‡p=0.58).

FIG. 21. Survival of Swiss-Webster mice immunized with various synthetic TLR agonists and challenged intranasally with 5 LD50 of *Bacillus anthracis* Ames Spores (MD-10-013). Mice were pretreated with aerosolized TLR agonists as indicated 24 hours before challenge with anthrax. ALIIS=NTHi bacterial lysate, 2395=ODN2395, 10101=ODN10101, M362=ODN-M362. 1×=ODN at 40 µg/ml and Pam2 at 20 µg/ml.

FIG. 22. Effect of aerosol pretreatment with ODNs/Pam2 or NTHi lysate on survival of influenza A/HK-infected mice. One 30-min Aerosol Treatments; Influenza Virus Dose: ~100 $TCID_{50}$/mouse.

DETAILED DESCRIPTION OF THE INVENTION

Figure 1:
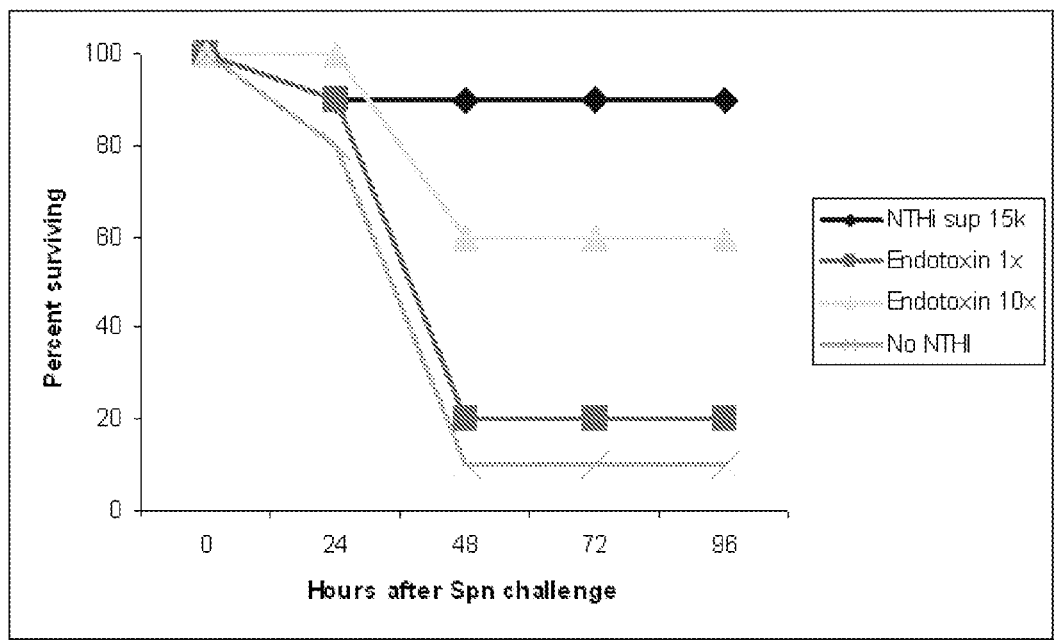
FIG. 1. Natural endotoxin (a TLR4 agonist) induces some StIR. Wildtype Swiss-Webster mice (10/group) were challenged with *S. pneumoniae* ($5 \times 10^{10}$ CFU/ml) 24 h after treatment with NTHI lysate ("NTHi sup"), the concentration of LPS estimated to be in the NTHi lysate ("Endotoxin 1×"), ten times the LPS believed to be in the lysate ("Endotoxin 10×") or no treatment.
Figure 2:
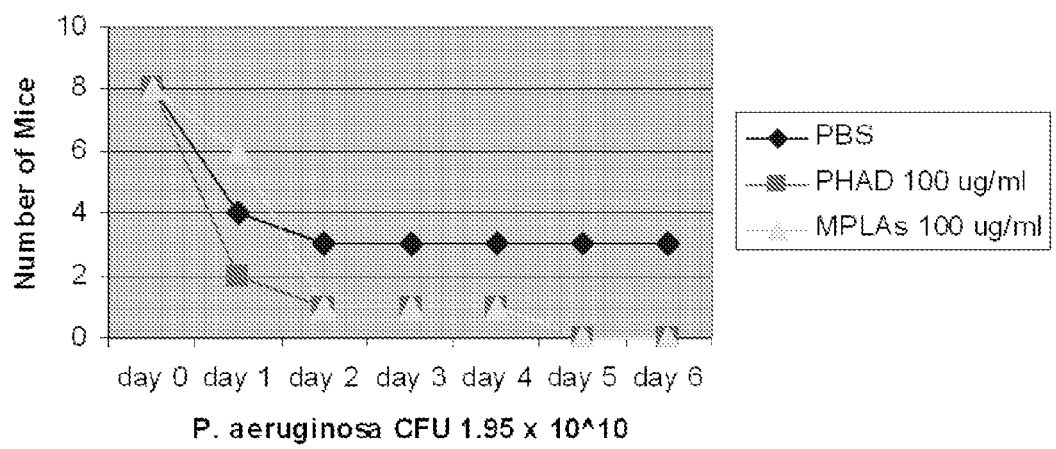
FIG. 2. Synthetic hexacylated lipid A (TLR4 agonist) does not induce StIR. Wildtype Swiss-Webster mice (8/group) were treated with synthetic lipid A suspensions or PBS 24 h prior to challenge with *P. aeruginosa*.
Figure 3:
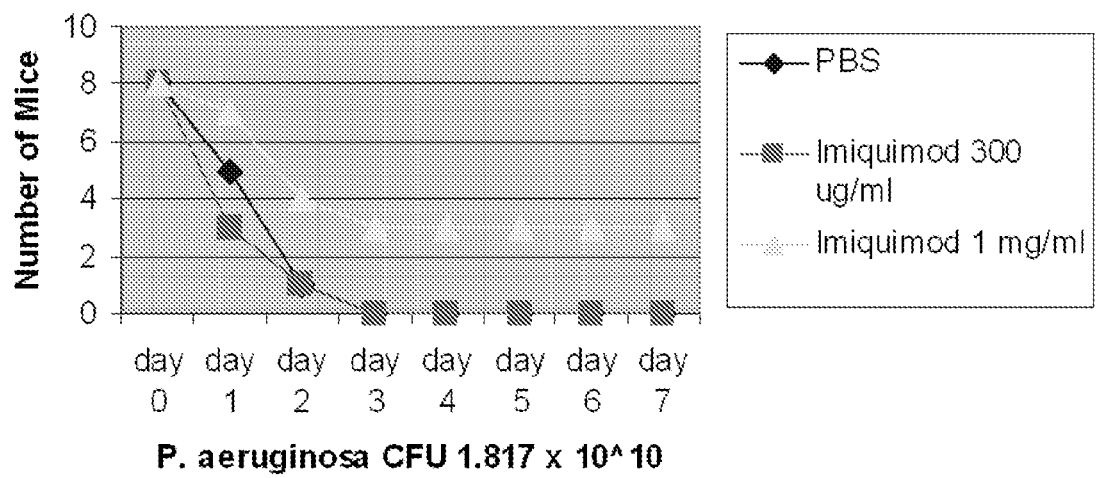
FIG. 3. A representative experiment is shown of Swiss-Webster mice (8/group) treated with high or low dose imiquimod (TLR7 agonist) or PBS 24 h before infectious challenge with *P. aeruginosa*.
Figure 4:
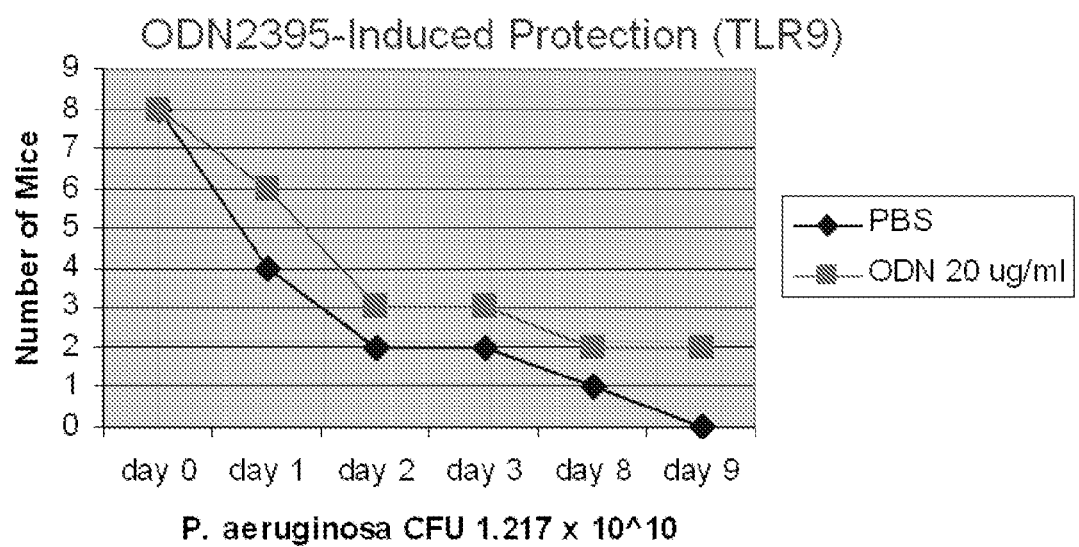
FIG. 4. TLR9 stimulation alone induces minimal protection. Wildtype Swiss-Webster mice (8/group) were treated with PBS or ODN2395 24 h prior to infection with inhaled *P. aeruginosa*.
Figure 5:
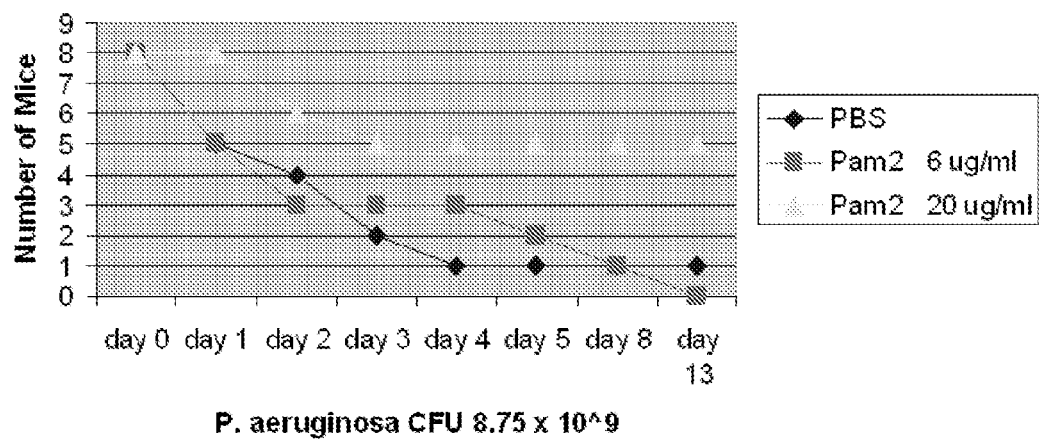
FIG. 5. High dose treatment with a TLR2/6 agonist induces StIR. Wildtype Swiss-Webster mice were treated with high or low dose Pam2CSK4 or PBS 24 h before infection with *P. aeruginosa*.
Figure 6:
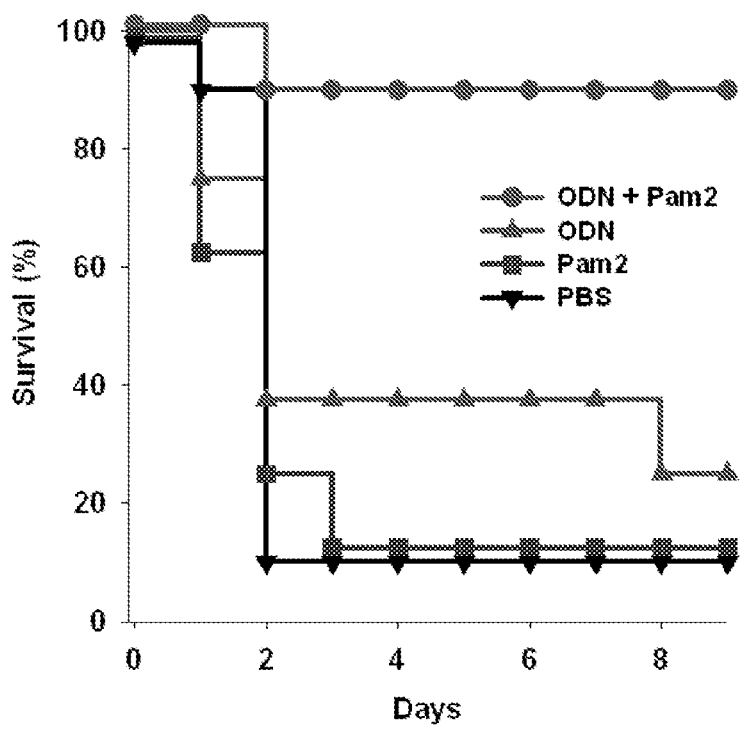
FIG. 6. A combination of TLR agonists induces greater StIR than either alone. Wildtype Swiss-Webster mice were treated with ODN2395 (20 µg/ml, 8 mice), Pam2CSK4 (20 µg/ml, 8 mice), both agonists (10 mice), or PBS (10 mice).
Figure 7:
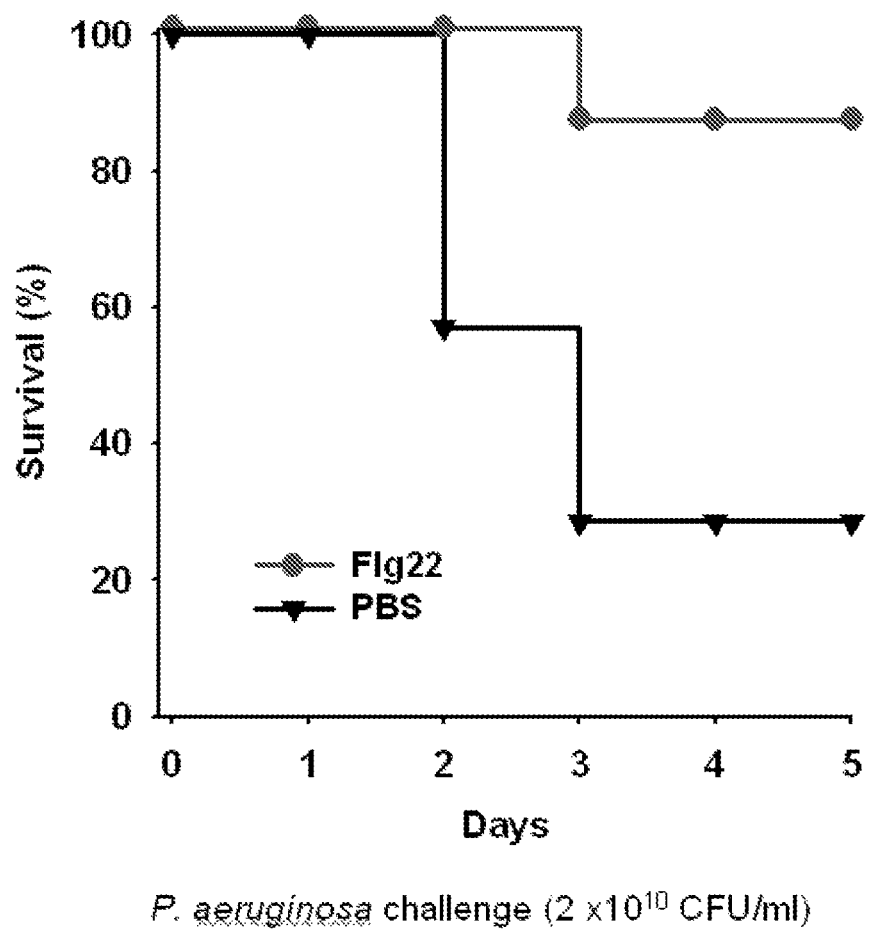
FIG. 7. A synthetic fragment of flagellin (TLR5 agonist) induces StIR. A 22 amino acid highly conserved segment of flagellin or PBS alone was aerosolized to wildtype Swiss-Webster 24 h prior to infection with *P. aeruginosa*.
Figure 8:
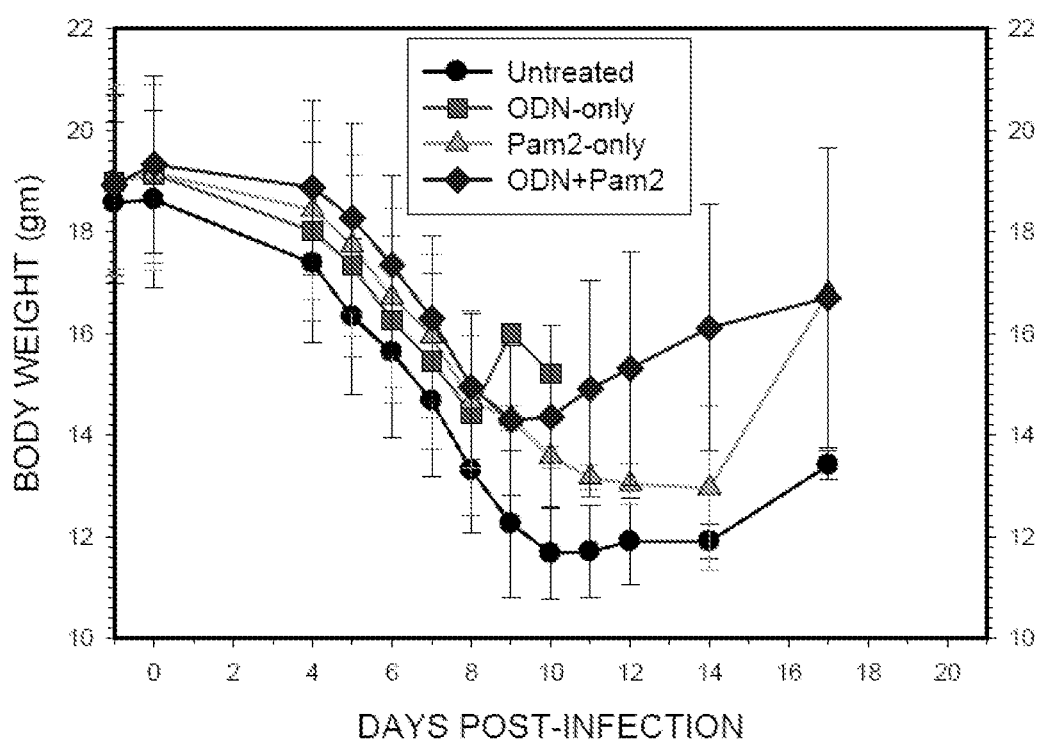
FIG. 8. Effect of influenza A/HK lung pool 11-29-05 aerosol infection on body weight: One 30-min Aerosol Treatment; Influenza Virus Dose: ~100 $TCID_{50}$/mouse. We FIG. 9. Effect of Influenza A/HK Lung Pool 11-29-05 Aerosol Infection on Survival: One 30-min Aerosol Treatments; Influenza Virus Dose: ~100 $TCID_{50}$/mouse.
Figure 9:
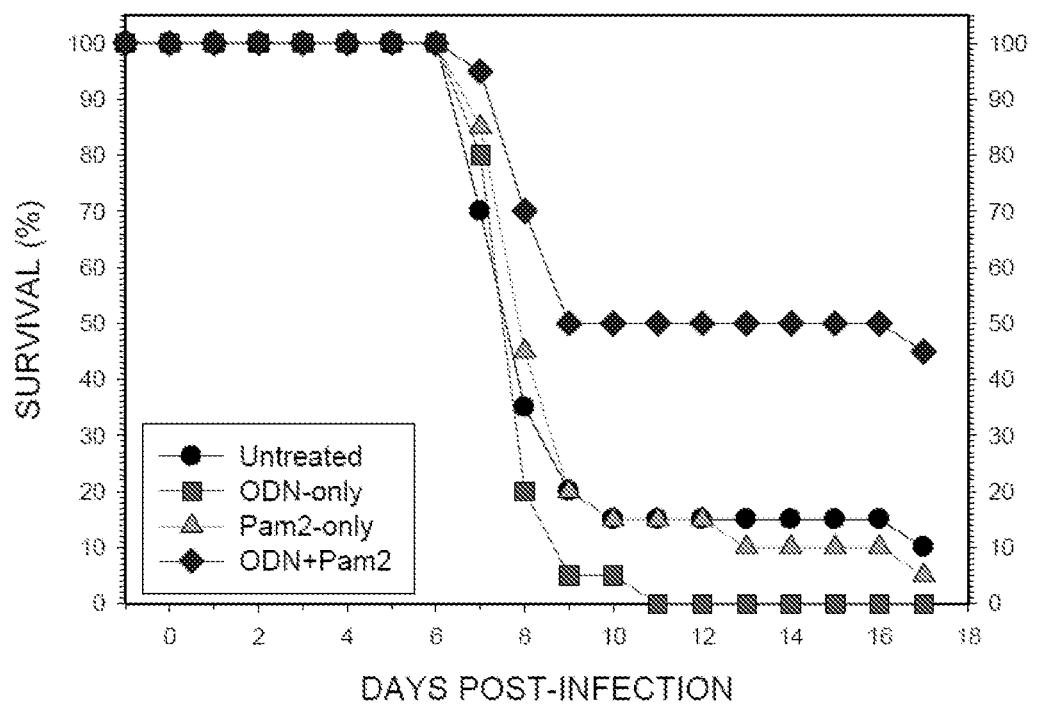
Figure 11:
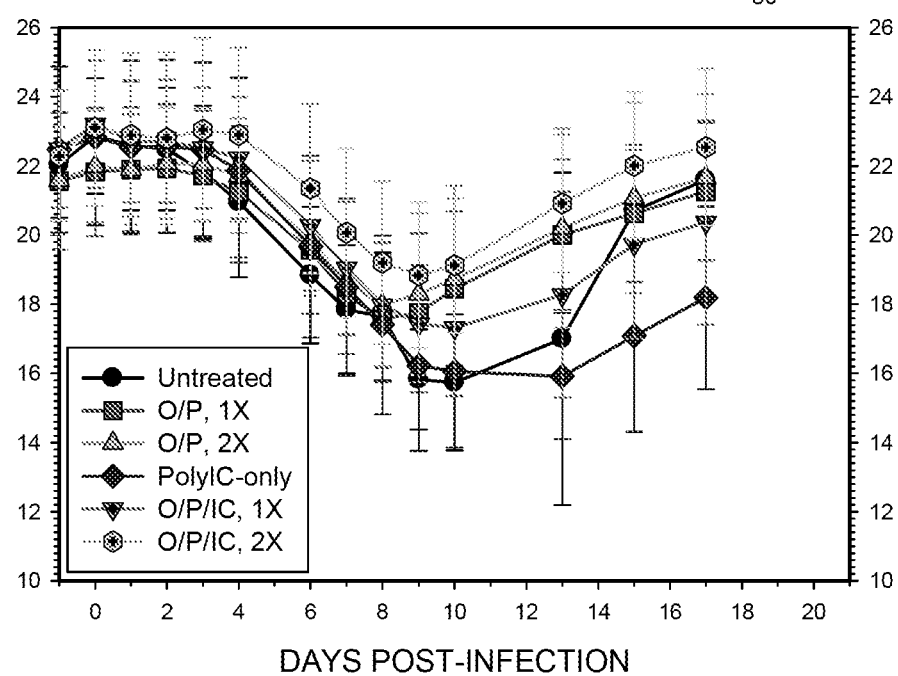
FIG. 11. Effect of influenza A/HK lung pool 11-29-05 aerosol infection on body weight: One 30-min Aerosol Treatment; Influenza Virus Dose: ~100 $TCID_{50}$/mouse. Weight declilnes initially as the infection progresses, reflecting the severity of illness, then rises during recovery.

The immune system is the system of specialized cells and organs that protect an organism from outside biological influences. When the immune system is functioning properly, it protects the body against microbial infections, and destroys cancer cells and foreign substances. If the immune system weakens, its ability to defend the body also weakens, allowing pathogens to grow in the body.

The immune system is often divided into: (a) an innate immunity comprised of components that provide an immediate "first-line" of defense to continuously ward off pathogens and (b) an adaptive (acquired) immunity comprising the manufacture of antibodies and production or stimulation of T-cells specifically designed to target particular pathogens. Using adaptive immunity the body can develop over time a specific immunity to particular pathogen(s). This response takes days to develop, and so is not effective at preventing an initial invasion, but it will normally prevent any subsequent infection, and also aids in clearing up longer-lasting infections.

In response to certain inflammatory stimuli, the secretory cells of the airway epithelium of mice and humans rapidly undergo a remarkable change in structure termed inflammatory metaplasia. Most of the structural changes can be ascribed to increased production of secreted, gel-forming mucins, while additional macromolecules with functions in mucin secretion, microbial killing or inflammatory signaling are also upregulated. The physiologic function of this response is thought to be augmentation of local defenses against microbial pathogens, although that hypothesis has received only limited formal testing. Paradoxically, excessive production and secretion of gel-forming mucins is a major cause of airflow obstruction in common inflammatory diseases of the airways such as asthma, cystic fibrosis, and chronic obstructive pulmonary disease (COPD). The stimulation of innate immunity without the production of mucin would provide an additional method of attenuating infection of the respiratory tract by preventing and/or treating a subject.

Embodiments of the invention include the stimulation of the airways of a subject with a composition comprising 1, 2, 3, 4, or more TLR agonists, including segments or derivatives or analogs thereof. A subject administered a composition of the invention is afforded a therapeutic, prophylactic, or therapeutic and prophylactic response to a potentially infecting organism. In particular aspects, a composition is aerosolized and administered via the respiratory tract. The composition is used to induce or otherwise elicit a protective effect by, for example, activating or augmenting innate immunity of the lungs.

Certain aspects of the invention include small molecules and/or TLR agonists derived from various microorganisms or sythesized by man. Typically, the small molecule and/or TLR agonist does not cause an increased production of secreted mucins. Embodiments of the invention can be used as a preventive and preemptive therapeutic against for example, bioweapons, neo-virulent microbes, or opportunistic microbes.

I. StIR COMPOSITIONS

A. Heterologous Compounds and Moieties

A number of non-host or heterologous molecules can stimulate, enhance or contribute to the production of an immune response. These moieties include various agonist of innate receptors and/or microbial components.

1. Innate Receptor Ligands

Pattern recognition receptors, or PRRs (innate receptors), are proteins expressed by cells of the innate immune system to identify pathogen-associated molecular patterns, or PAMPs, which are associated with microbial pathogens or cellular stress. PAMPs include, but are not limited to bacterial carbohydrates (e.g., lipopolysaccharide or LPS, mannose), nucleic acids (e.g., bacterial or viral DNA or RNA), peptidoglycans and lipotechoic acids (from Gram positive bacteria), N-formylmethionine, lipoproteins, fungal glucans, and the like.

PRRs are typically classified according to their ligand specificity, function, localization and/or evolutionary relationships. On the basis of function, PRRs may be divided into endocytic PRRs or signaling PRRs. Signaling PRRs include the large families of membrane-bound Toll-like receptors and cytoplasmic NOD-like receptors. Endocytic PRRs promote the attachment, engulfment and destruction of microorganisms by phagocytes, without relaying an intracellular signal. These PRRs recognize carbohydrates and include mannose receptors of macrophages, glucan receptors present on all phagocytes and scavenger receptors that recognize charged ligands, are found on all phagocytes and mediate removal of apoptotic cells.

A number of innate receptors have been identified as including, but not limited to Toll-like receptor (TLR), C-type lectin receptor (CLR), and nucleotide-binding oligomerization domain-like receptors (Nod-like receptor or NLR) TLRs are a class of proteins that play a key role in the innate immune system. They are single membrane-spanning non-catalytic receptors that recognize structurally conserved molecules derived from microbes. Once these microbes are present on or in the skin or intestinal tract mucosa, they are recognized by TLRs which activates immune cell responses. Interestingly, many of these TLR agonist do not induce a signficant StIR when administered alone. Typically, an individual or subject being treated using the methods described herein has been exposed to a pathogenic microbe or is at risk for such exposure.

a. Toll-Like Receptor (TLR) Agonist

Toll-like receptors (TLRs) are the best characterized of the PRRs (Ishii et al., 2008). They are highly conserved transmembrane proteins, consisting of an ectodomain with multiple leucine-rich repeats for pattern recognition, a membrane-spanning α-helix, and a Toll/interleukin-1 receptor (TIR) domain for intracellular signaling. At least 13 mammalian TLRs have been identified, each specifically localizing to either the plasma membrane or endosomal membranes, and each detects a unique complement of PAMPs (Akira et al., 2006; Shi et al., 2006). Upon PAMP recognition, signal transduction occurs via TLR-specific recruitment of cytosolic TIR adaptor protein combinations. In concert with one or more of the four other adaptors, the TIR adaptor protein MyD88 is required for signaling from most TLRs. The MyD88-independent signaling events observed from TLR3 and TLR4 require TIR adaptor TRIF (also known as TICAM-1), with or without participation of TRAM (Yamamoto et al., 2003). The TLR-specific TIR adaptor signaling cascade activates receptor-specific transcription factors, such as NF-κB, activating protein-1 and interferon regulatory factors (IRFs), leading to expression of inflammatory and antimicrobial genes (Akira et al., 2006; O'Neill, L. A., and Bowie, 2007; Takeda, K., and Akira, 2004).

A TLR agonist is any compound or substance that functions to activate a TLR, e.g., to induce a signaling event mediated by a TLR signal transduction pathway. Suitable TLR agonists include TLR1 agonists, TLR2 agonists, TLR3 agonists, TLR4 agonists, TLR5 agonists, TLR6 agonists, TLR7 agonists, TLR8 agonists, and TLR9 agonists.

It is now widely recognized that the generation of protective immunity depends not only on exposure to antigen, but also the context in which the antigen is encountered. Numerous examples exist in which introduction of a novel antigen into a host in an inflammatory context generates immunological tolerance rather than long-term immunity whereas exposure to antigen in the presence of an inflammatory agent (adjuvant) induces immunity (Mondino et al., 1996; Pulendran et al., 1998; Jenkins et al., 1994; and Keamey et al.,). Since it can mean the difference between tolerance and immunity, much effort has gone into discovering the "adjuvants" present within infectious agents that stimulate the molecular pathways involved in creating the appropriate immunogenic context of antigen presentation. It is now known that a good deal of the adjuvant activity is due to interactions of microbial and viral products with different members of the Toll Like Receptors (TLRs) expressed on immune cells (Beutler et al., 2004; Kaisho, 2002; Akira et al., 2003; and Takeda and Akira, 2004). The TLRs are named for their homology to a molecule in the *Drosophila*, called Toll, which functions in the development thereof and is involved in anti-microbial immunity (Lernaitre et al., 1996; and Hashimoto et al., 1988).

Early work showed the mammalian homologues to Toll and Toll pathway molecules were critical to the ability of cells of the innate immune system to respond to microbial challenges and microbial byproducts (Medzhitov et al., 1997; Medzhitov et al., 1998; Medzhitov et al., 2000; and Janeway et al., 2002). Since the identification of LPS as a TLR4 agonist (Poltorak et al., 1998) numerous other TLR agonists have been described such as tri-acyl multitype HPV polypeptides (TLR1), peptidoglycan, lipoteichoic acid and $Pam_3Cys$ (TLR2), dsRNA (TLM), flagellin (TLR5), diacyl multitype HPV polypeptides such as Malp-2 (TLR6), imidazoquinolines and single stranded RNA (TLR7,8), bacterial DNA, unmethylated CpG DNA sequences, and even human genomic DNA antibody complexes (TLR9) (Takeuchi et al., 2001; Edwards et al., 2002; Hayashi et al., 2003; Nagase et al., 2003).

The term "agonist," as used herein, refers to a compound that can combine with a receptor (e.g., a TLR) to produce a cellular activity. An agonist may be a ligand that directly binds to the receptor. Alternatively, an agonist may combine with a receptor indirectly by, for example, (a) forming a complex with another molecule that directly binds to the receptor, or (b) otherwise results in the modification of another compound so that the other compound directly binds to the receptor. An agonist may be referred to as an agonist of a particular TLR (e.g., a TLR7 agonist) or a particular combination of TLRs (e.g., a TLR 7/8 agonist—an agonist of both TLR7 and TLR8).

The terms "CpG-ODN," "CpG nucleic acid," "CpG polynucleotide," and "CpG oligonucleotide," used interchangeably herein, refer to a polynucleotide that comprises at least one 5'-CG-3' moiety, and in many embodiments comprises an unmethylated 5'-CG-3' moiety. In general, a CpG nucleic acid is a single- or double-stranded DNA or RNA polynucleotide having at least six nucleotide bases that may comprise, or consist of, a modified nucleotide or a sequence of modified nucleosides. In some embodiments, the 5'-CG-3' moiety of the CpG nucleic acid is part of a palindromic nucleotide sequence. In some embodiments, the 5'-CG-3' moiety of the CpG nucleic acid is part of a non-palindromic nucleotide sequence.

Suitable TLR agonists include isolated, naturally-occurring TLR agonists; and synthetic TLR agonists. TLR agonists isolated from a naturally-occurring source of TLR agonist are generally purified, e.g., the purified TLR agonist is at least about 80% pure, at least about 90% pure, at least about 95% pure, at least about 98% pure, at least about 99% pure, or more than 99% pure. Synthetic TLR agonists are prepared by standard methods, and are generally at least about 80% pure, at least about 90% pure, at least about 95% pure, at least about 98% pure, at least about 99% pure, or more than 99% pure.

Suitable TLR agonists include TLR agonists that are not attached to any other compound. Suitable TLR agonists include TLR agonists that are attached, covalently or non-covalently, to a second compound. In some embodiments, a TLR agonist is attached to another compound directly. In other embodiments, a TLR agonist is attached to another compound through a linker. The compound to which a TLR agonist is attached includes a carrier, a scaffold, an insoluble support, a microparticle, a microsphere, and the like. Carriers include therapeutic polypeptides; polypeptides that provide for increased solubility; polypeptides that increase the half-life of the TLR agonist in a physiological medium (e.g., serum or other bodily fluid); and the like. In some embodiments, a TLR agonist will be conjugated, directly or via a linker, to a second TLR agonist.

In some embodiments, the TLR agonist is a prodrug version of a TLR agonist. Prodrugs are composed of a prodrug portion covalently linked to an active therapeutic agent. Prodrugs are capable of being converted to drugs (active therapeutic agents) in vivo by certain chemical or enzymatic modifications of their structure. Examples of prodrug portions are well-known in the art and can be found in the following references: Biological Approaches to the Controlled Delivery of Drugs, R. L. Juliano, New York Academy of Sciences, (1988); Hydrolysis in Drug and Prodrug Metabolism: Chemistry, Biochemistry, and Enzymology, Bernard Testa, Vch Verlagsgesellschaft Mbh, (2003); and Prodrugs: Topical and Ocular Drug Delivery, Kenneth Sloan, Marcel Dekker; (1992). Examples of prodrug portions are peptides, e.g., peptides that direct the TLR ligand to the site of action, and a peptide which possesses two or more free and uncoupled carboxylic acids at its amino terminus. Other exemplary cleaveable prodrug portions include ester groups, ether groups, acyl groups, alkyl groups, phosphate groups, sulfonate groups, N-oxides, and tert-butoxy carbonyl groups.

In some embodiments, the TLR agonist is a monomeric TLR agonist. In other embodiments, the TLR agonist is multimerized, e.g., the TLR agonist is polymeric. In some embodiments, a multimerized TLR agonist is homofunctional, e.g., is composed of one type of TLR agonist. In other embodiments, the multimerized TLR agonist is a heterofunctional TLR agonist.

In some embodiments, a TLR ligand is a chimeric TLR ligand (also referred to herein as a "heterofunctional" TLR ligand). In some embodiments, a chimeric TLR agonist comprises a TLR9 agonist moiety, and a TLR2 agonist moiety. The following are non-limiting examples of heterofunctional TLR agonists.

In some embodiments, a chimeric TLR ligand has the following formula: (X)n-(Y)m, where X is a TLR1 agonist, TLR2 agonist, TLR3 agonist, TLR4 agonist, TLR5 agonist, TLR6 agonist, TLR7 agonist, TLR8 agonist, and TLR9 agonist, and where Y is a TLR2 agonist, TLR3 agonist, TLR4 agonist, TLR5 agonist, TLR6 agonist, TLR7 agonist, TLR8 agonist, and TLR9 agonist, and n and m are independently an integer from 1, 2, 3, 4, 5, 6, 7, 8, 9, 10 or more including all values and ranges there between. In certain embodiments, X or Y is TLR9 and X or Y is TLR2/6.

TLR2 agonists. TLR2 agonists include isolated, naturally-occurring TLR2 agonists; and synthetic TLR2 agonists. TLR2 agonists isolated from a naturally-occurring source of TLR2 agonist are generally purified, e.g., the purified TLR2 agonist is at least about 80% pure, at least about 90% pure, at least about 95% pure, at least about 98% pure, at least about 99% pure, or more than 99% pure. Synthetic TLR2 agonists are prepared by standard means, and are generally at least about 80% pure, at least about 90% pure, at least about 95% pure, at least about 98% pure, at least about 99% pure, or more than 99% pure.

TLR2 agonists include TLR2 agonists that are not attached to any other compound. TLR2 agonists include TLR2 agonists that are attached, covalently or non-covalently, to a second compound. In some embodiments, a TLR2 agonist is attached to another compound directly. In other embodiments, a TLR2 agonist is attached to another compound through a linker.

TLR2 agonists include synthetic triacylated and diacylated lipopeptides. A non-limiting example of a TLR2 ligand is FSL-1 (a synthetic lipoprotein derived from *Mycoplasma salivarium* 1), Pam$_3$Cys (tripalmitoyl-S-glyceryl cysteine) or S-[2,3-bis(palmitoyloxy)-(2RS)-propyl]-N-palmitoyl-(R)-cysteine, where "Pam$_3$" is "tripalmitoyl-S-glyceryl") (Aliprantis et al., 1999). Derivatives of Pam$_3$Cys are also suitable TLR2 agonists, where derivatives include, but are not limited to, S-[2,3-bis(palmitoyloxy)-(2-R,S)-propyl]-N-palmitoyl-(R)-Cys-(S)-Ser-(Lys)$_4$-hydroxytrihydrochloride; Pam$_3$Cys-Ser-Ser-Asn-Ala; PaM$_3$Cys-Ser-(Lys)$_4$; Pam$_3$Cys-Ala-Gly; Pam$_3$Cys-Ser-Gly; Pam$_3$Cys-Ser; PaM$_3$Cys-OMe; Pam$_3$Cys-OH; PamCAG, palmitoyl-Cys((RS)-2,3-di(palmitoyloxy)-propyl)-Ala-Gly-OH; and the like. Another non-limiting example of a suitable TLR2 agonist is Pam$_2$CSK$_4$ PaM$_2$CSK$_4$ (dipalmitoyl-S-glyceryl cysteine-serine-(lysine)$_4$; or Pam$_2$Cys-Ser-(Lys)$_4$) is a synthetic diacylated lipopeptide. Synthetic TLRs agonists have been described in the literature. See, e.g., Kellner et al. (1992); Seifer et al. (1990); Lee et al. (2003).

TLR3 Agonists.

TLR3 agonists include isolated, naturally-occurring TLR3 agonists; and synthetic TLR3 agonists. TLR3 agonists isolated from a naturally-occurring source of TLR3 agonist are generally purified, e.g., the purified TLR3 agonist is at least about 80% pure, at least about 90% pure, at least about 95% pure, at least about 98% pure, at least about 99% pure, or more than 99% pure. Synthetic TLR3 agonists are prepared by standard methods, and are generally at least about 80% pure, at least about 90% pure, at least about 95% pure, at least about 98% pure, at least about 99% pure, or more than 99% pure.

TLR3 agonists include TLR3 agonists that are not attached to any other compound. TLR3 agonists include TLR3 agonists that are attached, covalently or non-covalently, to a second compound. In some embodiments, a TLR3 agonist is attached to another compound directly. In other embodiments, a TLR3 agonist is attached to another compound through a linker.

TLR3 agonists include naturally-occurring double-stranded RNA (dsRNA); synthetic ds RNA; and synthetic dsRNA analogs; and the like (Alexopoulou et al., 2001). An exemplary, non-limiting example of a synthetic ds RNA analog is poly(I:C).

TLR4 Agonists.

Suitable TLR4 agonists include isolated, naturally-occurring TLR4 agonists; and synthetic TLR4 agonists. TLR4 agonists isolated from a naturally-occurring source of TLR4 agonist are generally purified, e.g., the purified TLR4 agonist is at least about 80% pure, at least about 90% pure, at least about 95% pure, at least about 98% pure, at least about 99% pure, or more than 99% pure. Synthetic TLR4 agonists are prepared by standard methods, and are generally at least about 80% pure, at least about 90% pure, at least about 95% pure, at least about 98% pure, at least about 99% pure, or more than 99% pure.

TLR4 agonists include TLR4 agonists that are not attached to any other compound. Suitable TLR4 agonists include TLR4 agonists that are attached, covalently or non-covalently, to a second compound. In some embodiments, a TLR4 agonist is attached to another compound directly. In other embodiments, a TLR4 agonist is attached to another compound through a linker. Suitable compounds to which a TLR4 agonist is attached include a carrier, a scaffold, and the like.

TLR4 agonists include naturally-occurring lipopolysaccharides (LPS), e.g., LPS from a wide variety of Gram negative bacteria; derivatives of naturally-occurring LPS; synthetic LPS; bacteria heat shock protein-60 (Hsp60); mannuronic acid polymers; flavolipins; teichuronic acids; *S. pneumoniae* pneumolysin; bacterial fimbriae, respiratory syncytial virus coat protein; and the like. TLR4 agonist also include monophosphoryl lipid A-synthetic (MPLAs, Invivogen) and Phosphorylated HexaAcyl Disaccharide (PHAD, Avanti Polar Lipids), as well as other synthetic TLR4 agonists.

TLR 5 Agonists.

Suitable TLR5 agonists include isolated, naturally-occurring TLR5 agonists; and synthetic TLR5 agonists. TLR5 agonists isolated from a naturally-occurring source of TLR5 agonist are generally purified, e.g., the purified TLR4 agonist is at least about 80% pure, at least about 90% pure, at least about 95% pure, at least about 98% pure, at least about 99% pure, or more than 99% pure. Synthetic TLR5 agonists are prepared by standard methods, and are generally at least about 80% pure, at least about 90% pure, at least about 95% pure, at least about 98% pure, at least about 99% pure, or more than 99% pure.

TLR5 agonists include TLR5 agonists that are not attached to any other compound. Suitable TLR5 agonists include TLR5 agonists that are attached, covalently or non-covalently, to a second compound. In some embodiments, a TLR5 agonist is attached to another compound directly. In other embodiments, a TLR5 agonist is attached to another compound through a linker. Suitable compounds to which a TLR5 agonist is attached include a carrier, a scaffold, and the like.

TLR5 agonists include a highly conserved 22 amino acid segment of flagellin as well as full length flagellin and other segments thereof.

TLR7 Agonists.

Suitable TLR7 agonists include isolated, naturally-occurring TLR7 agonists; and synthetic TLR7 agonists. TLR7 agonists isolated from a naturally-occurring source of TLR7 agonist are generally purified, e.g., the purified TLR7 agonist is at least about 80% pure, at least about 90% pure, at least about 95% pure, at least about 98% pure, at least about 99% pure, or more than 99% pure. Synthetic TLR7 agonists are prepared by standard means, and are generally at least about 80% pure, at least about 90% pure, at least about 95% pure, at least about 98% pure, at least about 99% pure, or more than 99% pure.

TLR7 agonists include TLR7 agonists that are not attached to any other compound. Suitable TLR7 agonists include TLR7 agonists that are attached, covalently or non-covalently, to a second compound. In some embodiments, a TLR7 agonist is attached to another compound directly. In other embodiments, a TLR7 agonist is attached to another compound through a linker.

TLR7 ligands include imidazoquinoline compounds; guanosine analogs; pyrimidinone compounds such as bropirimine and bropirimine analogs; and the like. Imidazoquinoline compounds that function as TLR7 ligands include, but are not limited to, imiquimod, (also known as Aldara, R-837, S-26308), and R-848 (also known as resiquimod, S-28463; having the chemical structure: 4-amino-2-ethoxymethyl-α, α-dimethyl-1H-imidazol[4,5-c]quinoli-ne-1-ethanol). Suitable imidazoquinoline agents include imidazoquinoline amines, imidazopyridine amines, 6,7-fused cycloalkylimidazopyridine amines, and 1,2 bridged imidazoquinoline amines. These compounds have been described in U.S. Pat. Nos. 4,689,338, 4,929,624, 5,238,944, 5,266,575, 5,268,376, 5,346,905, 5,352,784, 5,389,640, 5,395,937, 5,494,916, 5,482,936, 5,525,612, 6,039,969 and 6,110,929. Particular species of imidazoquinoline agents that are suitable for use in a subject method include R-848 (S-28463); 4-amino-2ethoxymethyl-α,α-dimethyl-1H-imidazo[4,5-c]quinoline-s-i-ethanol; and 1-(2-methylpropyl)-1H-imidazo[4,5-c]quinolin-4-amine (R-837 or Imiquimod). Also suitable for use is the compound 4-amino-2-(ethoxymethyl)-α,α-dimethyl-6,7,8,9-tetrahydro-1H-imidazo[4,5-c]quinoline-1-ethanol hydrate (see, e.g., BM-003 in Gorden et al. (2005).

Suitable compounds include those having a 2-aminopyridine fused to a five membered nitrogen-containing heterocyclic ring. Such compounds include, for example, imidazoquinoline amines including but not limited to substituted imidazoquinoline amines such as, for example, amide substituted imidazoquinoline amines, sulfonamide substituted imidazoquinoline amines, urea substituted imidazoquinoline amines, aryl ether substituted imidazoquinoline amines, heterocyclic ether substituted imidazoquinoline amines, amido ether substituted imidazoquinoline amines, sulfonamido ether substituted imidazoquinoline amines, urea substituted imidazoquinoline ethers, thioether substituted imidazoquinoline amines, and 6-, 7-, 8-, or 9-aryl or heteroaryl substituted imidazoquinoline amines; tetrahydroimidazoquinoline amines including but not limited to amide substituted tetrahydroimidazoquinoline amines, sulfonamide substituted tetrahydroimidazoquinoline amines, urea substituted tetrahydroimidazoquinoline amines, aryl ether substituted tetrahydroimidazoquinoline amines, heterocyclic ether substituted tetrahydroimidazoquinoline amines, amido ether substituted tetrahydroimidazoquinoline amines, sulfonamido ether substituted tetrahydroimidazoquinoline amines, urea substituted tetrahydroimidazoquinoline ethers, and thioether substituted tetrahydroimidazoquinoline amines; imidazopyridine amines including but not limited to amide substituted imidazopyridine amines, sulfonamido substituted imidazopyridine amines, urea substituted imidazopyridine amines, aryl ether substituted imidazopyridine amines, heterocyclic ether substituted imidazopyridine amines, amido ether substituted imidazopyridine amines, sulfonamido ether substituted imidazopyridine amines, urea substituted imidazopyridine ethers, and thioether substituted imidazopyridine amines; 1,2-bridged imidazoquinoline amines; 6,7-fused cycloalkylimidazopyridine amines; imidazonaphthyridine amines; tetrahydroimidazonaphthyridine amines; oxazoloquinoline amines; thiazoloquinoline amines; oxazolopyridine amines; thiazolopyridine amines; oxazolonaphthyridine amines; thiazolonaphthyridine amines; and 1H-imidazo dimers fused to pyridine amines, quinoline amines, tetrahydroquinoline amines, naphthyridine amines, and tetrahydronaphthyridine amines.

Compounds include a substituted imidazoquinoline amine, a tetrahydroimidazoquinoline amine, an imidazopyridine amine, a 1,2-bridged imidazoquinoline amine, a 6,7-fused cycloalkylimidazopyridine amine, an imidazonaphthyridine amine, a tetrahydroimidazonaphthyridine amine, an oxazoloquinoline amine, a thiazoloquinoline amine, an oxazolopyridine amine, a thiazolopyridine amine, an oxazolonaphthyridine amine, and a thiazolonaphthyridine amine.

As used herein, a substituted imidazoquinoline amine refers to an amide substituted imidazoquinoline amine, a sulfonamide substituted imidazoquinoline amine, a urea substituted imidazoquinoline amine, an aryl ether substituted imidazoquinoline amine, a heterocyclic ether substituted imidazoquinoline amine, an amido ether substituted imidazoquinoline amine, a sulfonamido ether substituted imidazoquinoline amine, a urea substituted imidazoquinoline ether, a thioether substituted imidazoquinoline amines, or a 6-, 7-, 8-, or 9-aryl or heteroaryl substituted imidazoquinoline amine.

Guanosine analogs that function as TLR7 ligands include certain C8-substituted and N7,C8-disubstituted guanine ribonucleotides and deoxyribonucleotides, including, but not limited to, Loxoribine (7-allyl-8-oxoguanosine), 7-thia-8-oxoguanosine (TOG), 7-deazaguanosine, and 7-deazadeoxyguanosine (Lee et al., 2003). Bropirimine (PNU-54461), a 5-halo-6-phenyl-pyrimidinone, and bropirimine analogs are described in the literature and are also suitable for use. See, e.g., Vroegop et al. (1999). Additional examples of suitable C8-substituted guanosines include but are not limited to 8-mercaptoguanosine, 8-bromoguanosine, 8-methylguanosine, 8-oxo-7,8-dihydroguanosine, C8-arylamino-2'-deoxyguanosine, C8-propynyl-guanosine, C8- and N7-substituted guanine ribonucleosides such as 7-allyl-8-oxoguanosine (loxoribine) and 7-methyl-8-oxoguanosine, 8-aminoguanosine, 8-hydroxy-2'-deoxyguanosine, and 8-hydroxyguanosine.

In some embodiments a substituted guanine TLR7 ligand is monomeric. In other embodiments, a substituted guanine TLR7 ligand is multimeric. Thus, in some embodiments, a TLR7 ligand has the formula: (B)q, where B is a substituted guanine TLR7 ligand, and q is 1, 2, 3, 4, 5, 6, 7, 8, 9, or 10. The individual TLR7 ligand monomers in a multimeric TLR7 ligand are linked, covalently or non-covalently, either directly to one another or through a linker. Suitable TLR7 agonists include a TLR7 ligand as described in U.S. Patent Publication 2004/0162309.

In some embodiments, a TLR7 agonist is a selective TLR7 agonist, e.g., the agonist modulates cellular activity through TLR7, but does not modulate cellular activity through TLR8. TLR7-selective agonists include those shown in U.S. Patent Publication 2004/0171086. Such TLR7 selective agonist compounds include, but are not limited to, $N^1$-{4-[4-amino-2-(2-methoxyethyl)-6,7,8,9-tetrahydro-1H-imidazo[4,5-c]quinolin-1-yl]butyl}-4-fluoro-1-benzenesulfonamide, $N^1$-[4-(4-amino-2-(2-methoxyethyl)-1H-imidazo[4,5-c]

quinolin-1-yl)butyl]-4-fluoro-1-benzenesulfonamide, N-[4-(4-amino-2-propyl-1H-imidazo[4,5-c]quinolin-1-yl)butyl]methanesulfonamide, N-{3-[4-amino-2-(2-methoxyethyl)-1H-imidazo[4,5-c]quinolin-1-yl]-2,2-dimethylpropyl}benzamide, N-(2-{2-[4-amino-2-(2-methoxyethyl)-1H-imidazo[4,5-c]quinolin-1-yl]ethoxy}ethyl)-N-methylmethane sulfonamide, N-(2-{2-[4-amino-2-(2-methoxyethyl)-6,7,8,9-tetrahydro-1H-imidazo[4,5-c]quinolin-1-yl]ethoxy}ethyl)benzamide, N-[4-(4-amino-2-methyl-1H-imidazo[4,5-c]quinolin-1-yl)butyl]cyclopentanecarboxamide, 1-[4-(1,1-dioxidoisothiazolidin-2-yl)butyl]-2-(2-methoxyethyl)-1H-imidazo[4,5-c]quinolin-4-amine, 2-methyl-1-(5-methylsulfonyl)pentyl-6,7,8,9-tetrahydro-1H-imidazo[4,5-c]quinolin-4-amine, N-{2-[4-amino-2-(ethoxymethyl)-6,7-dimethyl-1H-imidazo[4,5-c]pyridin-1-yl]-1,1-dimethylethyl}-N-cyclohexylurea, N-[2-(4-amino-2-ethyl-1H-imidazo[4,5-c]quinolin-1-yl)-1,1-dimethylethyl]benzamide, N-[3-(4-amino-2-butyl-1H-imidazo[4,5-c]quinolin-1-yl)-2,2-dimethylpropyl]methanesulfonamide, 1-[6-(methanesulfonyl)hexyl]-6,7-dimethyl-2-propyl-1 H-imidazo[4,5-c]pyridin-4-amine, 6-(6-amino-2-propyl-1H-imidazo[4,5-c]quinolin-1-yl)-N-methoxy-N-methylhexamide, 1-[2,2-dimethyl-3-(methylsulfonyl)propyl]-2-(ethoxymethyl)-1H-imidazo[4,5-c]quinolin-4-amine, N-[4-(4-amino-2-methyl-1H-imidazo[4,5-c]quinolin-1-yl)butyl]-N-methyl-N-phenylurea, 1-{3-[4-amino-1-(2-methylpropyl)-1H-imidazo[4,5-c]quinolin-8-yl]phenyl}ethanone, 7-(4-amino-2-propyl-1H-imidazo[4,5-c]quinolin-1-yl)-2-methylheptan-2-ol, N-methyl-4-(4-amino-2-ethyl-1H-imidazo[4,5-c]quinolin-1-yl)butane-1-sulfonamide, N-(4-methoxybenzyl)-4-(4-amino-2-ethyl-1H-imidazo[4,5-c]quinolin-1-yl)butane-1-sulfonamide, N-{2-[4-amino-3-(ethoxymethyl)-6,7-dimethyl-1H-imidazo[4,5-c]pyridin-1-yl]-1,1-dimethylethyl}methanesulfonamide, 2-ethoxymethyl-1-(3-methoxypropyl)-7-(5-hydroxymethylpyridin-3-yl)-1H-imidazo[4,5-c]quinolin-4-amine, 1-[(2,2-dimethyl-1,3-dioxolan-4-yl)methyl]-2-(ethoxymethyl)-7-(pyridin-3-yl)-1H-imidazo[4,5-c]quinolin-4-amine, 4-[3-(4-amino-6,7-dimethyl-2-propyl-1H-imithizo[4,5-c]pyridin-1-yl)propane-1-sulfonyl]-benzoic acid ethyl ester, 2-butyl-1-{2-[2-(methylsulfonyl)ethoxy]ethyl}-1H-imidazo[4,5-c]quinolin-4-amine, N-(2-{4-amino-2-ethoxymethyl-7-[6-(methanesulfonylamino)hexyloxy]-1H-imidazo[4,5-c]quinolin-1-yl}-1,1-dimethylethyl)methanesulfonamide, N-(6-{[4-amino-2-ethoxymethyl-1-(2-methanesulfonylamino-2-methylpropyl)-1H-imidazo[4,5-c]quinolin-7-yl]oxy}hexyl)acetamide, 1-[4-(1,1-dioxidoisothiazolidin-2-yl)butyl]-2-ethoxymethyl-7-(pyridin-3-yl)-1H-imidazo[4,5-c]quinolin-4-amine, 1-[4-(1,1-dioxidoisothiazolidin-2-yl)butyl]-2-ethoxymethyl-7-(pyridin-4-yl)-1H-imidazo[4,5-c]quinolin-4-amine, 1-[4-(1,1-dioxidoisothiazolidin-2-yl)butyl]-2-ethoxymethyl-7-phenyl-1H-imidazo[4,5-c]quinolin-4-amine, 2-(ethoxymethyl)-1-{[1-(methylsulfonyl)piperidin-4-yl]methyl}-7-(pyridin-3-yl)-1H-imidazo[4,5-c]quinolin-4-amine, 2-(ethoxymethyl)-1-[(1-isobutyrylpiperidin-4-yl)methyl]-7-(pyridin-3-yl)-1H-imidazo[4,5-c]quinolin-4-amine, 2-(ethoxymethyl)-1-{[1-(morpholic-4-ylcarbonyl)piperidin-4-yl]methyl}-7-(pyridin-3-yl)-1H-imidazo[4,5-c]quinolin-4-amine, Cyclopropanecarboxylic acid [3-(4-amino-2-propyl-1H-imidazo[4,5-c]quinolin-1-yl)propoxy]amide, Isopropylcarbamic acid 4-amino-2-(2-methoxyethyl)-1-propyl-1H-imidazo[4,5-c]quinolin-7-yl ester, Ethyl 4-(4-amino-2-propyl-1H-imidazo[4,5-c]quinolin-1-yl)butyrate, 1-[4-amino-2-ethyl-7-(pyridin-3-yl)-1H-imidazo[4,5-c]quinolin-1-yl]-2-methylpropan-2-ol, 1-(4-amino-2-ethyl-7-[5-{hydroxymethyl)pyridin-3-yl]-1H-imidazo[4,5-c]quinolin-1-yl}-2-methylpropan-2-ol, 1-(3-[4-amino-2-(2-methoxyethyl)-8-(pyridin-3-yl)-1H-imidazo[4,5-c]quinolin-1-yl]propyl}pyrolidin-2-one, N-(2-{4-amino-2-ethoxymethyl-7-[6-(methanesulfonylamino)hexyloxy]-1H-imidazo[4,5-c]quinolin-1-yl}-1,1-dimethylethyl)acetamide, 1-{3-[4-amino-7-(3-hydroxymethylphenyl)-2-(2-methoxyethyl)-1H-imidazo[4,5-c]quinolin-1-yl]propyl}pyrrolidin-2-one, N-{4-[4-amino-2-ethoxymethyl-7-(pyridin-3-yl)-1H-imidazo[4,5-c]quinolin-1-yl]butyl}-N'-propylurea, N-{4-[4-amino-2-ethoxymethyl-7-(pyridin-3-yl)-1H-imidazo[4,5-c]quinolin-1-yl]butyl}butyramide, 5-(4-amino-2-propyl-1H-imidazo[4,5-c]quinolin-1-yl)-4,4-dimethylpentan-2-one, 1-cyclohexylmethyl-2-ethoxymethyl-7-(5-hydroxymethylpyridin-3-yl)-1H-imidazo[4,5-c]quinolin-4-amine, N,N-dimethyl-5-(4-amino-2-ethoxymethyl-1H-imidazo[4,5-c]quinolin-1-yl)pentane-1-sulfonamide, N-{3-[(4-amino-2-ethoxymethyl-1H-imidazo[4,5-c]quinolin-1-yl)amino]propyl}methanesulfonamide, and/or N,N-dimethyl-4-(4-amino-2-ethoxymethyl-1H-imidazo[4,5-c]quinolin-1-yl)butane-1-sulfonamide.

Additional suitable TLR7 selective agonists include, but are not limited to, 2-(ethoxymethyl)-1-(2-methylpropyl)-1H-imidazo[4,5-c]quinolin-4-amine (U.S. Pat. No. 5,389,640); 2-methyl-1-[2-(3-pyridin-3-ylpropoxy)ethyl]-1H-imidazo[4,5-c]quinolin-4-amine (WO 02/46193); N-(2-{2-[4-amino-2-(2-methoxyethyl)-1H-imidazo[4,5-c]quinolin-1-yl]ethoxy}ethyl)-N-methylcyclohexanecarboxamide (U.S. Patent Publication 2004/0171086); 1-[2-(benzyloxy)ethyl]-2-methyl-1H-imidazo[4,5-c]quinolin-4-amine (WO 02/46189); N-{8-[4-amino-2-(2-methyoxyethyl)-1H-imidazo[4,5-c]quinolin-1-yl]octyl}-N-phenylurea (U.S. Patent Publication 2004/0171086 (IRM5)); 2-butyl-1-[5-(methylsulfonyl)pentyl]-1H-imidazo[4,5-c]quinolin-4-amine (WO 02/46192); N-{3-[4-amino-2-(2-methoxyethyl)-1H-imidazo[4,5-c]quinolin-1-yl]propyl}-4-methylbenzenesulfonamide (U.S. Pat. No. 6,331,539); and N-[4-(4-amino-2-ethyl-1H-imidazo[4,5-c]quinolin-1-yl)butyl]cyclohexanecar-boxamide (U.S. Patent Publication 2004/0171086 (IRM8)). Also suitable for use is the TLR7-selective agonist N-[4-(4-amino-2-ethyl-1H-imidazo[4,5-c]quinolin-1-yl)butyl-]methanesulfon-amide (Gorden et al., 2005).

TLR8 Agonists.

Suitable TLR8 agonists include isolated, naturally-occurring TLR8 agonists; and synthetic TLR8 agonists. TLR8 agonists isolated from a naturally-occurring source of TLR8 agonist are generally purified, e.g., the purified TLR8 agonist is at least about 80% pure, at least about 90% pure, at least about 95% pure, at least about 98% pure, at least about 99% pure, or more than 99% pure. Synthetic TLR8 agonists are prepared by standard methods, and are generally at least about 80% pure, at least about 90% pure, at least about 95% pure, at least about 98% pure, at least about 99% pure, or more than 99% pure.

TLR8 agonists include TLR8 agonists that are not attached to any other compound. TLR8 agonists include TLR8 agonists that are attached, covalently or non-covalently, to a second compound. In some embodiments, a TLR8 agonist is attached to another compound directly. In other embodiments, a TLR8 agonist is attached to another compound through a linker.

TLR8 agonists include, but are not limited to, compounds such as R-848, and derivatives and analogs thereof. Suitable TLR8 agonists include compounds having a 2-aminopyridine fused to a five membered nitrogen-containing heterocyclic ring. Such compounds include, for example, imidazoquinoline amines including but not limited to substituted imidazoquinoline amines such as, for example, amide substituted imidazoquinoline amines, sulfonamide substituted imidazoquinoline amines, urea substituted imidazoquinoline amines, aryl ether substituted imidazoquinoline amines, heterocyclic ether substituted imidazoquinoline amines, amido ether substituted imidazoquinoline amines, sulfonamido ether substituted imidazoquinoline amines, urea substituted imidazoquinoline ethers, thioether substituted imidazoquinoline amines, and 6-, 7-, 8-, or 9-aryl or heteroaryl substituted imidazoquinoline amines; tetrahydroimidazoquinoline amines including but not limited to amide substituted tetrahydroimidazoquinoline amines, sulfonamide substituted tetrahydroimidazoquinoline amines, urea substituted tetrahydroimidazoquinoline amines, aryl ether substituted tetrahydroimidazoquinoline amines, heterocyclic ether substituted tetrahydroimidazoquinoline amines, amido ether substituted tetrahydroimidazoquinoline amines, sulfonamido ether substituted tetrahydroimidazoquinoline amines, urea substituted tetrahydroimidazoquinoline ethers, and thioether substituted tetrahydroimidazoquinoline amines; imidazopyridine amines including but not limited to amide substituted imidazopyridine amines, sulfonamide substituted imidazopyridine amines, urea substituted imidazopyridine amines, aryl ether substituted imidazopyridine amines, heterocyclic ether substituted imidazopyridine amines, amido ether substituted imidazopyridine amines, sulfonamido ether substituted imidazopyridine amines, urea substituted imidazopyridine ethers, and thioether substituted imidazopyridine amines; 1,2-bridged imidazoquinoline amines; 6,7-fused cycloalkylimidazopyridine amines; imidazonaphthyridine amines; tetrahydroimidazonaphthyridine amines; oxazoloquinoline amines; thiazoloquinoline amines; oxazolopyridine amines; thiazolopyridine amines; oxazolonaphthyridine amines; thiazolonaphthyridine amines; and 1H-imidazo dimers fused to pyridine amines, quinoline amines, tetrahydroquinoline amines, naphthyridine amines, or tetrahydronaphthyridine amines.

In one particular embodiment, the TLR8 agonist is an amide substituted imidazoquinoline amine. In an alternative embodiment, the TLR8 agonist is a sulfonamide substituted imidazoquinoline amine. In another alternative embodiment, the TLR8 agonist is a urea substituted imidazoquinoline amine. In another alternative embodiment, the TLR8 agonist is an aryl ether substituted imidazoquinoline amine. In another alternative embodiment, the TLR8 agonist is a heterocyclic ether substituted imidazoquinoline amine. In another alternative embodiment, the TLR8 agonist is an amido ether substituted imidazoquinoline amine. In another alternative embodiment, the TLR8 agonist is a sulfonamido ether substituted imidazoquinoline amine. In another alternative embodiment, the TLR8 agonist is a urea substituted imidazoquinoline ether. In another alternative embodiment, the TLR8 agonist is a thioether substituted imidazoquinoline amine. In another alternative embodiment, the TLR8 agonist is a 6-, 7-, 8-, or 9-aryl or heteroaryl substituted imidazoquinoline amine.

In another alternative embodiment, the TLR8 agonist is an amide substituted tetrahydroimidazoquinoline amine. In another alternative embodiment, the TLR8 agonist is a sulfonamide substituted tetrahydroimidazoquinoline amine. In another alternative embodiment, the TLR8 agonist is a urea substituted tetrahydroimidazoquinoline amine.

In another alternative embodiment, the TLR8 agonist is an aryl ether substituted tetrahydroimidazoquinoline amine. In another alternative embodiment, the TLR8 agonist is a heterocyclic ether substituted tetrahydroimidazoquinoline amine. In another alternative embodiment, the TLR8 agonist is an amido ether substituted tetrahydroimidazoquinoline amine. In another alternative embodiment, the TLR8 agonist is a sulfonamido ether substituted tetrahydroimidazoquinoline amine. In another alternative embodiment, the TLR8 agonist is a urea substituted tetrahydroimidazoquinoline ether. In another alternative embodiment, the TLR8 agonist is a thioether substituted tetrahydroimidazoquinoline amine.

In another alternative embodiment, the TLR8 agonist is an amide substituted imidazopyridine amines. In another alternative embodiment, the TLR8 agonist is a sulfonamide substituted imidazopyridine amine. In another alternative embodiment, the TLR8 agonist is a urea substituted imidazopyridine amine. In another alternative embodiment, the TLR8 agonist is an aryl ether substituted imidazopyridine amine. In another alternative embodiment, the TLR8 agonist is a heterocyclic ether substituted imidazopyridine amine. In another alternative embodiment, the TLR8 agonist is an amido ether substituted imidazopyridine amine. In another alternative embodiment, the TLR8 agonist is a sulfonamido ether substituted imidazopyridine amine. In another alternative embodiment, the TLR8 agonist is a urea substituted imidazopyridine ether. In another alternative embodiment, the TLR8 agonist is a thioether substituted imidazopyridine amine.

In another alternative embodiment, the TLR8 agonist is a 1,2-bridged imidazoquinoline amine. In another alternative embodiment, the TLR8 agonist is a 6,7-fused cycloalkylimidazopyridine amine.

In another alternative embodiment, the TLR8 agonist is an imidazonaphthyridine amine. In another alternative embodiment, the TLR8 agonist is a tetrahydroimidazonaphthyridine amine. In another alternative embodiment, the TLR8 agonist is an oxazoloquinoline amine. In another alternative embodiment, the TLR8 agonist is a thiazoloquinoline amine. In another alternative embodiment, the TLR8 agonist is an oxazolopyridine amine. In another alternative embodiment, the TLR8 agonist is a thiazolopyridine amine. In another alternative embodiment, the TLR8 agonist is an oxazolonaphthyridine amine. In another alternative embodiment, the TLR8 agonist is a thiazolonaphthyridine amine.

In yet another alternative embodiment, the TLR8 agonist is a 1H-imidazo dimer fused to a pyridine amine, quinoline amine, tetrahydroquinoline amine, naphthyridine amine, or a tetrahydronaphthyridine amine.

In some embodiments, the TLR8 agonist is a selective TLR8 agonist, e.g., the agonist modulates cellular activity through TLR8, but does not modulate cellular activity through TLR7. TLR8-selective agonists include those in U.S. Patent Publication 2004/0171086. Such TLR8 selective agonist compounds include, but are not limited to, the compounds shown in U.S. Patent Publication No. 2004/0171086 that include N-{4-[4-amino-2-(2-methoxyethyl)-1H-imidazo[4,5-c]quinolin-1-yl]butyl}quinolin-3-carboxamide, N-{4-[4-amino-2-(2-methoxyethyl)-1H-imidazo[4,5-c]quinolin-1-yl]butyl}quinoxoline-2-carboxamide, and N-[4-(4-amino-2-propyl-1H-imidazo[4,5-c]quinolin-1-yl)butyl]morpholine-4-carboxamide.

Other suitable TLR8-selective agonists include, but are not limited to, 2-propylthiazolo[4,5-c]quinolin-4-amine (U.S. Pat. No. 6,110,929); $N^1$-[2-(4-amino-2-butyl-1H-imidazo[4,5-c][1,5]naphthridin-1-yl)ethyl]-2-amino-4-methylpentanamide (U.S. Pat. No. 6,194,425); $N^1$-[4-(4-amino-1H-imidazo[4,5-c]quinolin-1-yl)butyl]-2-phenoxy-benzamide (U.S. Pat. No. 6,451,810); $N^1$-[2-(4-amino-2-butyl-1H-imidazo[4,5-c]quinolin-1-yl)ethyl]-1-propa-nesulfonamide (U.S. Pat. No. 6,331,539); N-{2-[2-(4-amino-2-ethyl-1H-imidazo[4,5-c]quinolin-1-yl)ethyoxy]ethyl}-N'-phenylurea (U.S. Patent Publication 2004/0171086); 1-{4-[3,5-dichlorophenyl)thio]

butyl}-2-ethyl-1H-imidazo[4,5-c]quinolin-4-amine (U.S. Patent Publication 2004/0171086); N-{2-[4-amino-2-(ethoxymethyl)-1H-imidazo[4,5-c]quinolin-1-yl]ethyl}-N'-(3-cyanophenyl)urea (WO 00/76518 and U.S. Patent Publication No. 2004/0171086); and 4-amino-α,α-dimethyl-2-methoxyethyl-1H-imidazo[4,5-c]quinoli-ne-1-ethanol (U.S. Pat. No. 5,389,640). Included for use as TLR8-selective agonists are the compounds in U.S. Patent Publication No. 2004/0171086. Also suitable for use is the compound 2-propylthiazolo-4,5-c]quinolin-4-amine (Gorden et al., 2005 supra).

TLR9 Agonists.

Suitable TLR9 agonists include isolated, naturally-occurring TLR9 agonists; and synthetic TLR9 agonists. TLR9 agonists isolated from a naturally-occurring source of TLR9 agonist are generally purified, e.g., the purified TLR9 agonist is at least about 80% pure, at least about 90% pure, at least about 95% pure, at least about 98% pure, at least about 99% pure, or more than 99% pure. Synthetic TLR9 agonists are prepared by standard methods, and are generally at least about 80% pure, at least about 90% pure, at least about 95% pure, at least about 98% pure, at least about 99% pure, or more than 99% pure.

TLR9 agonists include TLR9 agonists that are not attached to any other compound. TLR9 agonists include TLR9 agonists that are attached, covalently or non-covalently, to a second compound. In some embodiments, a TLR9 agonist is attached to another compound directly. In other embodiments, a TLR9 agonist is attached to another compound through a linker.

Examples of TLR9 agonists (also referred to herein as "TLR9 ligands") include nucleic acids comprising the sequence 5'-CG-3' (a "CpG nucleic acid"), in certain aspects C is unmethylated. The terms "polynucleotide," and "nucleic acid," as used interchangeably herein in the context of TLR9 ligand molecules, refer to a polynucleotide of any length, and encompasses, inter alia, single- and double-stranded oligonucleotides (including deoxyribonucleotides, ribonucleotides, or both), modified oligonucleotides, and oligonucleosides, alone or as part of a larger nucleic acid construct, or as part of a conjugate with a non-nucleic acid molecule such as a polypeptide. Thus a TLR9 ligand may be, for example, single-stranded DNA (ssDNA), double-stranded DNA (dsDNA), single-stranded RNA (ssRNA) or double-stranded RNA (dsRNA). TLR9 ligands also encompasses crude, detoxified bacterial (e.g., mycobacterial) RNA or DNA, as well as enriched plasmids enriched for a TLR9 ligand. In some embodiments, a "TLR9 ligand-enriched plasmid" refers to a linear or circular plasmid that comprises or is engineered to comprise a greater number of CpG motifs than normally found in mammalian DNA.

Examples of non-limiting TLR9 ligand-enriched plasmids are described in Roman et al. (1997). Modifications of oligonucleotides include, but are not limited to, modifications of the 3'OH or 5'OH group, modifications of the nucleotide base, modifications of the sugar component, and modifications of the phosphate group.

A TLR9 ligand may comprise at least one nucleoside comprising an L-sugar. The L-sugar may be deoxyribose, ribose, pentose, deoxypentose, hexose, deoxyhexose, glucose, galactose, arabinose, xylose, lyxose, or a sugar "analog" cyclopentyl group. The L-sugar may be in pyranosyl or furanosyl form.

TLR9 ligands generally do not provide for, nor is there any requirement that they provide for, expression of any amino acid sequence encoded by the polynucleotide, and thus the sequence of a TLR9 ligand may be, and generally is, non-coding. TLR9 ligands may comprise a linear double or single-stranded molecule, a circular molecule, or can comprise both linear and circular segments. TLR9 ligands may be single-stranded, or may be completely or partially double-stranded.

In some embodiments, a TLR9 ligand for use in a subject method is an oligonucleotide, e.g., consists of a sequence of from about 5 nucleotides to about 200 nucleotides, from about 10 nucleotides to about 100 nucleotides, from about 12 nucleotides to about 50 nucleotides, from about 15 nucleotides to about 25 nucleotides, from 20 nucleotides to about 30 nucleotides, from about 5 nucleotides to about 15 nucleotides, from about 5 nucleotides to about 10 nucleotides, or from about 5 nucleotides to about 7 nucleotides in length. In some embodiments, a TLR9 ligand that is less than about 15 nucleotides, less than about 12 nucleotides, less than about 10 nucleotides, or less than about 8 nucleotides in length is associated with a larger molecule.

In some embodiments, a TLR9 ligand does not provide for expression of a peptide or polypeptide in a eukaryotic cell, e.g., introduction of a TLR9 ligand into a eukaryotic cell does not result in production of a peptide or polypeptide, because the TLR9 ligand does not provide for transcription of an mRNA encoding a peptide or polypeptide. In these embodiments, a TLR9 ligand lacks promoter regions and other control elements necessary for transcription in a eukaryotic cell.

A TLR9 ligand can be isolated from a bacterium, e.g., separated from a bacterial source; produced by synthetic methods (e.g., produced by standard methods for chemical synthesis of polynucleotides); produced by standard recombinant methods, then isolated from a bacterial source; or a combination of the foregoing. In many embodiments, a TLR9 ligand is purified, e.g., is at least about 80%, at least about 90%, at least about 95%, at least about 98%, at least about 99%, or more, e.g., 99.5%, 99.9%, or more, pure. In many embodiments, the TLR9 ligand is chemically synthesized, then purified.

In other embodiments, a TLR9 ligand is part of a larger nucleotide construct (e.g., a plasmid vector, a viral vector, or other such construct). A wide variety of plasmid and viral vector are known in the art, and need not be elaborated upon here. A large number of such vectors have been described in various publications, including, e.g., Current Protocols in Molecular Biology, (1987, and updates).

In general, a TLR9 ligand used in a subject composition comprises at least one unmethylated CpG motif. The relative position of any CpG sequence in a polynucleotide in certain mammalian species (e.g., rodents) is 5'-CG-3' (i.e., the C is in the 5' position with respect to the G in the 3' position).

In some embodiments, a TLR9 ligand comprises a central palindromic core sequence comprising at least one CpG sequence, where the central palindromic core sequence contains a phosphodiester backbone, and where the central palindromic core sequence is flanked on one or both sides by phosphorothioate backbone-containing polyguanosine sequences.

In other embodiments, a TLR9 ligand comprises one or more TCG sequences at or near the 5' end of the nucleic acid; and at least two additional CG dinucleotides. In some of these embodiments, the at least two additional CG dinucleotides are spaced three nucleotides, two nucleotides, or one nucleotide apart. In some of these embodiments, the at least two additional CG dinucleotides are contiguous with one another. In some of these embodiments, the TLR9 ligand comprises (TCG)n, where n=1 to 3, at the 5' end of the nucleic acid. In other embodiments, the TLR9 ligand comprises (TCG)n, where n=1 to 3, and where the (TCG)n sequence is flanked by one nucleotide, two nucleotides, three nucleotides, four nucleotides, or five nucleotides, on the 5' end of the (TCG)n sequence.

Exemplary consensus CpG motifs of TLR9 ligands useful in the invention include, but are not necessarily limited to: 5'-Purine-Purine-(C)-(G)-Pyrimidine-Pyrimidine-3', in which the TLR9 ligand comprises a CpG motif flanked by at least two purine nucleotides (e.g., GG, GA, AG, AA, II, etc.,) and at least two pyrimidine nucleotides (CC, TT, CT, TC, UU, etc.); 5'-Purine-TCG-Pyrimidine-Pyrimidine-3'; 5'-TCG-N-N-3'; where N is any base; 5'-Nx(CG)nNy, where N is any base, where x and y are independently any integer from 0 to 200, e.g., 0, 1, 2, 3, 4, 5, 6, 7, 8, 9, 10, 11-15, 16-20, 21-25, 25-30, 30-50, 50-75, 75-100, 100-150, or 150-200; and n is any integer that is 1 or greater, e.g., 1, 2, 3, 4, 5, 6, 7, 8, 9, 10, or greater. 5'-Nx(TCG)nNy, where N is any base, where x and y are independently any integer from 0 to 200, e.g., 0, 1, 2, 3, 4, 5, 6, 7, 8, 9, 10, 11-15, 16-20, 21-25, 25-30, 30-50, 50-75, 75-100, 100-150, or 150-200; and n is any integer that is 1 or greater, e.g., 1, 2, 3, 4, 5, 6, 7, 8, 9, 10, or greater. 5'-(TCG)n-3', where n is any integer that is 1 or greater, e.g., to provide a TCG-based TLR9 ligand (e.g., where n=3, the polynucleotide comprises the sequence 5'-TCGNNTCGNNTCG-3'; SEQ ID NO:3); 5'Nm-(TCG)n-Np-3', where N is any nucleotide, where m is zero, one, two, or three, where n is any integer that is 1 or greater, and where p is one, two, three, or four; 5'Nm-(TCG)n-Np-3', where N is any nucleotide, where m is zero to 5, and where n is any integer that is 1 or greater, where p is four or greater, and where the sequence N-N-N-N comprises at least two CG dinucleotides that are either contiguous with each other or are separated by one nucleotide, two nucleotides, or three nucleotides; and 5'-Purine-Purine-CG-Pyrimidine-TCG-3'.

Where a nucleic acid TLR9 ligand comprises a sequence of the formula: 5'-Nm-(TCG)n-Np-3', where N is any nucleotide, where m is zero to 5, and where n is any integer that is 1 or greater, where p is four or greater, and where the sequence N-N-N-N comprises at least two CG dinucleotides that are either contiguous with each other or are separated by one nucleotide, two nucleotides, or three nucleotides, exemplary TLR9 ligands useful in the invention include, but are not necessarily limited to: (1) a sequence of the formula in which n=2, and Np is NNCGNNCG; (2) a sequence of the formula in which n=2, and Np is AACGTTCG; (3) a sequence of the formula in which n=2, and Np is TTCGAACG; (4) a sequence of the formula in which n=2, and Np is TACGTACG; (5) a sequence of the formula in which n=2, and Np is ATCGATCG; (6) a sequence of the formula in which n=2, and Np is CGCGCGCG; (7) a sequence of the formula in which n=2, and Np is GCCGGCCG; (8) a sequence of the formula in which n=2, and Np is CCCGGGCG; (9) a sequence of the formula in which n=2, and Np is GGCGCCCG; (10) a sequence of the formula in which n=2, and Np is CCCGTTCG; (11) a sequence of the formula in which n=2, and Np is GGCGTTCG; (12) a sequence of the formula in which n=2, and Np is TTCGCCCG; (13) a sequence of the formula in which n=2, and Np is TTCGGGCG; (14) a sequence of the formula in which n=2, and Np is AACGCCCG; (15) a sequence of the formula in which n=2, and Np is AACGGGCG; (16) a sequence of the formula in which n=2, and Np is CCCGAACG; and (17) a sequence of the formula in which n=2, and Np is GGCGAACG; and where, in any of 1-17, m=zero, one, two, or three.

Where a nucleic acid TLR9 ligand comprises a sequence of the formula: 5'Nm-(TCG)n-Np-3', where N is any nucleotide, where m is zero, one, two, or three, where n is any integer that is 1 or greater, and where p is one, two, three, or four, exemplary TLR9 ligands useful in the invention include, but are not necessarily limited to: (1) a sequence of the formula where m=zero, n=1, and Np is T-T-T; (2) a sequence of the formula where m=zero, n=1, and Np is T-T-T-T; (3) a sequence of the formula where m=zero, n=1, and Np is C-C-C-C; (4) a sequence of the formula where m=zero, n=1, and Np is A-A-A-A; (5) a sequence of the formula where m=zero, n=1, and Np is A-G-A-T; (6) a sequence of the formula where Nm is T, n=1, and Np is T-T-T; (7) a sequence of the formula where Nm is A, n=1, and Np is T-T-T; (8) a sequence of the formula where Nm is C, n=1, and Np is T-T-T; (9) a sequence of the formula where Nm is G, n=1, and Np is T-T-T; (10) a sequence of the formula where Nm is T, n=1, and Np is A-T-T; (11) a sequence of the formula where Nm is A, n=1, and Np is A-T-T; and (12) a sequence of the formula where Nm is C, n=1, and Np is A-T-T.

The core structure of a TLR9 ligand useful in the invention may be flanked upstream and/or downstream by any number or composition of nucleotides or nucleosides. In some embodiments, the core sequence of a TLR9 ligand is at least 6 bases or 8 bases in length, and the complete TLR9 ligand (core sequences plus flanking sequences 5', 3' or both) is usually between 6 bases or 8 bases, and up to about 200 bases in length.

DNA-based TLR9 ligands useful in the invention include, but are not necessarily limited to, polynucleotides comprising one or more of the following nucleotide sequences:

AGCGCT, AGCGCC, AGCGTT, AGCGTC, AACGCT, AACGCC,

AACGTT, AACGTC, GGCGCT, GGCGCC, GGCGTT, GGCGTC,

GACGCT, GACGCC, GACGTT, GACGTC, GTCGTC, GTCGCT,

GTCGTT, GTCGCC, ATCGTC, ATCGCT, ATCGTT, ATCGCC,

TCGTCG, and TCGTCGTCG.

Additional TLR9 ligands useful in the invention include, but are not necessarily limited to, polynucleotides comprising one or more of the following nucleotide sequences:

TCGXXXX, TCGAXXX, XTCGXXX, XTCGAXX, TCGTCGA,

TCGACGT, TCGAACG, TCGAGAT, TCGACTC, TCGAGCG,

TCGATTT, TCGCTTT, TCGGTTT, TCGTTTT, TCGTCGT,

ATCGATT, TTCGTTT, TTCGATT, ACGTTCG, AACGTTC,

TGACGTT, TGTCGTT, TCGXXX, TCGAXX, TCGTCG, AACGTT,

ATCGAT, GTCGTT, GACGTT, TCGXX, TCGAX, TCGAT,

TCGTT, TCGTC, TCGA, TCGT, TCGX, and TCG.
(where "X" is any nucleotide)

DNA-based TLR9 ligands useful in the invention include, but are not necessarily limited to, polynucleotides comprising the following octameric nucleotide sequences:

AGCGCTCG, AGCGCCCG, AGCGTTCG, AGCGTCCG, AACGCTCG,

AACGCCCG, AACGTTCG, AACGTCCG, GGCGCTCG, GGCGCCCG,

GGCGTTCG, GGCGTCCG, GACGCTCG, GACGCCCG, GACGTTCG, and GACGTCCG.

A TLR9 ligand useful in carrying out a subject method can comprise one or more of any of the above CpG motifs. For example, a TLR9 ligand useful in the invention can comprise a single instance or multiple instances (e.g., 2, 3, 4, 5 or more) of the same CpG motif. Alternatively, a TLR9 ligand can comprise multiple CpG motifs (e.g., 2, 3, 4, 5 or more) where at least two of the multiple CpG motifs have different consensus sequences, or where all CpG motifs in the TLR9 ligand have different consensus sequences.

A TLR9 ligand useful in the invention may or may not include palindromic regions. If present, a palindrome may extend only to a CpG motif, if present, in the core hexamer or octamer sequence, or may encompass more of the hexamer or octamer sequence as well as flanking nucleotide sequences.

Multimeric TLR9 Ligands.

In some embodiments, a TLR9 ligand is multimeric. A multimeric TLR9 ligand comprises two, three, four, five, six, seven, eight, nine, ten, or more individual (monomeric) nucleic acid TLR9 ligands, as described above, linked via non-covalent bonds, linked via covalent bonds, and either linked directly to one another, or linked via one or more spacers. Suitable spacers include nucleic acid and non-nucleic acid molecules, as long as they are biocompatible. In some embodiments, multimeric TLR9 ligand comprises a linear array of monomeric TLR9 ligands. In other embodiments, a multimeric TLR9 ligand is a branched, or dendrimeric, array of monomeric TLR9 ligands.

In some embodiments, a multimeric TLR9 ligand has the general structure (X1)n(X2)n where X is a nucleic acid TLR9 ligand as described above, and having a length of from about 6 nucleotides to about 200 nucleotides, e.g., from about 6 nucleotides to about 8 nucleotides, from about 8 nucleotides to about 10 nucleotides, from about 10 nucleotides to about 12 nucleotides, from about 12 nucleotides to about 15 nucleotides, from about 15 nucleotides to about 20 nucleotides, from about 20 nucleotides to about 25 nucleotides, from about 25 nucleotides to about 30 nucleotides, from about 30 nucleotides to about 40 nucleotides, from about 40 nucleotides to about 50 nucleotides, from about 50 nucleotides to about 60 nucleotides, from about 60 nucleotides to about 70 nucleotides, from about 70 nucleotides to about 80 nucleotides, from about 80 nucleotides to about 90 nucleotides, from about 90 nucleotides to about 100 nucleotides, from about 100 nucleotides to about 125 nucleotides, from about 125 nucleotides to about 150 nucleotides, from about 150 nucleotides to about 175 nucleotides, or from about 175 nucleotides to about 200 nucleotides; and where n is any number from one to about 100, e.g., n=1, 2, 3, 4, 5, 6, 7, 8, 9, 10, from 10 to about 15, from 15 to about 20, from 20 to about 25, from 25 to about 30, from 30 to about 40, from 40 to about 50, from 50 to about 60, from 60 to about 70, from 70 to about 80, from 80 to about 90, or from 90 to about 100. In these embodiments, X and X2 differ in nucleotide sequence from one another by at least one nucleotide, and may differ in nucleotide sequence from one another by two, three, four, five, six, seven, eight, nine, ten, or more bases.

As noted above, in some embodiments, a subject multimeric TLR9 ligand comprises a TLR9 ligand separated from an adjacent TLR9 ligand by a spacer. In some embodiments, a spacer is a non-TLR9 ligand nucleic acid. In other embodiments, a spacer is a non-nucleic acid moiety. Suitable spacers include those described in U.S. Patent Publication 20030225016. A TLR9 ligand is multimerized using any known method.

TLR9 Ligand Modifications.

A TLR9 ligand suitable for use in a subject composition can be modified in a variety of ways. For example, a TLR9 ligand can comprise backbone phosphate group modifications (e.g., methylphosphonate, phosphorothioate, phosphoroamidate and phosphorodithioate internucleotide linkages), which modifications can, for example, enhance their stability in vivo, making them particularly useful in therapeutic applications. A particularly useful phosphate group modification is the conversion to the phosphorothioate or phosphorodithioate forms of a nucleic acid TLR9 ligand. Phosphorothioates and phosphorodithioates are more resistant to degradation in vivo than their unmodified oligonucleotide counterparts, increasing the half-lives of the TLR9 ligands and making them more available to the subject being treated.

Other modified TLR9 ligands encompassed by the present invention include TLR9 ligands having modifications at the 5' end, the 3' end, or both the 5' and 3' ends. For example, the 5' and/or 3' end can be covalently or non-covalently associated with a molecule (either nucleic acid, non-nucleic acid, or both) to, for example, increase the bio-availability of the TLR9 ligand, increase the efficiency of uptake where desirable, facilitate delivery to cells of interest, and the like. Molecules for conjugation to a TLR9 ligand include, but are not necessarily limited to, cholesterol, phospholipids, fatty acids, sterols, oligosaccharides, polypeptides (e.g., immunoglobulins), peptides, antigens (e.g., peptides, small molecules, etc.), linear or circular nucleic acid molecules (e.g., a plasmid), insoluble supports, therapeutic polypeptides, and the like. Therapeutic polypeptides that are suitable for attachment to a TLR9 agonist include, but are not limited to, a dendritic cell growth factor (e.g., GM-CSF); a cytokine; an interferon (e.g., an IFN-α, an IFN-β, etc.); a TNF-α antagonist; and the like.

A TLR9 ligand is in some embodiments linked (e.g., conjugated, covalently linked, non-covalently associated with, or adsorbed onto) an insoluble support. An exemplary, non-limiting example of an insoluble support is cationic poly(D, L-lactide-co-glycolide).

Additional TLR9 ligand conjugates, and methods for making same, are known in the art and described in, for example, WO 98/16427 and WO 98/55495. Thus, the term TLR9 ligand" includes conjugates comprising a nucleic acid TLR9 ligand.

A polypeptide, e.g., a therapeutic polypeptide, may be conjugated directly or indirectly, e.g., via a linker molecule, to a TLR9 ligand. A wide variety of linker molecules are known in the art and can be used in the conjugates. The linkage from the peptide to the oligonucleotide may be through a peptide reactive side chain, or the N- or C-terminus of the peptide. Linkage from the oligonucleotide to the peptide may be at either the 3' or 5' terminus, or internal. A linker may be an organic, inorganic, or semi-organic molecule, and may be a polymer of an organic molecule, an inorganic molecule, or a co-polymer comprising both inorganic and organic molecules.

If present, the linker molecules are generally of sufficient length to permit oligonucleotides and/or polynucleotides and a linked polypeptide to allow some flexible movement between the oligonucleotide and the polypeptide. The linker molecules are generally about 6-50 atoms long. The linker molecules may also be, for example, aryl acetylene, ethylene glycol oligomers containing 2-10 monomer units, diamines, diacids, amino acids, or combinations thereof. Other linker molecules which can bind to oligonucleotides may be used in light of this disclosure.

b. NOD Like Receptor (NLR) Agonist

The NOD-like receptors (NLRs) are cytoplasmic proteins that may have a variety of functions in regulation of inflammatory and apoptotic responses. Approximately 20 of these proteins have been found in the mammalian genome and include two major subfamilies called NODs and NALPs, the MHC Class II transactivator (CIITA), and some other molecules (e.g., IPAF and BIRC1). Current understanding suggests some of these proteins recognize endogenous or microbial molecules or stress responses and form oligomers that activate inflammatory caspases (e.g., caspase 1) causing cleavage and activation of important inflammatory cytokines such as IL-1, and/or activate the NF-κB signaling pathway to induce production of inflammatory molecules. The NLR family is known under several different names, including the CATERPILLER (or CLR) or NOD-LRR family.

The ligands are currently known for NOD1 and NOD2. NOD1 recognizes a molecule called meso-DAP, that is a peptidoglycan constituent of only Gram negative bacteria. NOD2 proteins recognize intracellular MDP (muramyl dipeptide), which is a peptidoglycan constituent of both Gram positive and Gram negative bacteria. NODS transduce signals in the pathway of NF-κB and MAP kinases via the serine-threonine kinase called RIP2. NOD proteins are so named as they contain a nucleotide-binding oligomerization domain which binds nucleotide triphosphate. NODs signal via N-terminal CARD domains to activate downstream gene induction events, and interact with microbial molecules by means of a C-terminal leucine-rich repeat (LRR) region.

Like NODs, NALP proteins contain C-terminal LRRs, which appear to act as a regulatory domain and may be involved in the recognition of microbial pathogens. Also like NODs, these proteins also contain a nucleotide binding site (NBS) for nucleotide triphosphates. Interaction with other proteins (e.g., the adaptor molecule ASC) is mediated via N-terminal pyrin (PYD) domain. There are 14 members of this subfamily in humans (called NALP1 to NALP14). Mutations in NALP3 are responsible for the autoinflammatory diseases familial cold autoinflammatory syndrome, Muckle-Wells syndrome and neonatal onset multisystem inflammatory disease. Activators of NALP3 include muramyl dipeptide, bacterial DNA, ATP, toxins, double stranded RNA, paramyxoviruses and uric acid crystals.

Other NLRs such as IPAF and NAIP5/Birc1e have also been shown to activate caspase-1 in response to *Salmonella* and *Legionella*.

NLR agonist include, but are not limited to GM-tripeptide (*Shigella flexneri*), Meso-lanthionine (*Helicobacter pylori*), meso-DAP, γ-D-Glu-DAP (iEDAP) (Enteroinvasive *Escherichia coli*), D-lactyl-L-ala-γ-Glu-meso-DAP-Gly (FK156) (*Pseudomonas*), Heptanolyl-γ-Glu-meso-DAP-D-ala (FK565) (*Chlamydia, Listeria monocyotgenes*), MDP (*Listeria monocyotgenes*), MurNAc-L-Ala-γ-D-Glu-L-Lys (M-TRILys) (*Streptococcus pneumoniae, Salmonella typhimurium, Salmonella flexneri*), Flagellin, Bacterial RNA, ATP, Nigericin, Maitotoxin, Uric acid crystals, Aerolysin, and Anthrax lethal toxin.

c. RIG-Like Receptor (RLR) Agonist

Various cells in the body are capable of sensing infectious viruses and initiating reactions collectively known as antiviral innate responses. These responses include the production of antiviral cytokines such as type I interferon (IFN) and subsequent synthesis of antiviral enzymes, which are responsible for the impairment of viral replication and promoting adaptive immune responses. RIG (retinoic acid inducible gene)-like receptors sense viral RNA molecules that trigger components of the innate immune system. Ligands for RLRs include, but are not limited to ssRNA, dsRNA, polyinosine-polycytidylic acid ("poly(rI:rC)", a synthetic analog of double-stranded RNA (dsRNA), and other viral nucleic acids—inlcuding portions RNA viral genomes (e.g., Japanese encephalitis virus (JEV), vesicular stomatitis virus (VSV), influenza virus, Dengue virus, West Nile virus, Reovirus, and encephalomyocarditis virus (EMCV))—and analogs thereof. An RNA segment or analog can at least 20, 25, 30, 35, 40 or more nucleotides or nucleotide pairs or the equivalent. In certain aspects the RNA is a 5' triphosphate RNA.

d. Leukocyte Immunoglobulin-Like Receptor (LIR) Agonist

The cloning of eight LIR-1-related molecules (see Fanger et al., 1999, and references therein), with 63-84% amino acid identity to LIR-1, established a novel family of immunoreceptors (LIRs). The LIRs can be grouped according to their structure. Five of the LIRs (1, 2, 3, 5, and 8) have cytoplasmic domains containing two, three, or four immunoreceptor tyrosine-based inhibitory motif (ITIM)-like sequences. Although two of the tyrosine-based motifs (motif nos. 2 and 3; I/VxYxxL/V) fit the original ITIM consensus sequence, some of these LIRs contain tyrosine-based motifs with an asparagine residue (motif no. 1; NxYxxL/V) or a serine residue (motif no. 4; SxYxxL/V) located two amino acids upstream of the tyrosine. In contrast to the ITIM-containing LIRs, three of the LIRs (6a, 6b, and 7) contain short cytoplasmic regions and a positively charged arginine residue in the transmembrane domain.

Members of the LIR family bind MHC class I molecules. LIR-1 and LIR-2 recognize HLA-A (A0101, A0301), HLA-B (B0702, B0802, B1501, B2702), and HLA-C (C0304) alleles and the non-classical class I molecule HLA-G1. The binding specificity of LIR-1 and LIR-2, therefore, is distinct from that of the KIRs, which recognize relatively restricted subsets of MHC class I alleles as well as CD94/NKG2A. The latter molecule recognizes HLA-E whose binding pockets are occupied by peptides derived from the signal sequence of specific MHC class I antigens.

2. Microbial Components a. EF2505

In certain aspects, methods of treating, inhibiting or attenuating a microbial infection in an individual who has or is at risk for developing such an infection is contemplated, the methods comprising administering an effective amount of a StIR peptide, e.g. *Enterococcus faecalis* protein EF2505 (SEQ ID NO:1), or a fragment of derivative thereof to said individual. Typically, the individual or subject has been exposed to a pathogenic microbe or is at risk for such exposure. In certain aspects the StIR peptide is a purified or isolated polypeptide or peptide. The term "purified" or "isolated" means that component was previously isolated away or purified from other proteins and that the component is at least about 70, 75, 80, 90, 95, 97, or 99% pure prior to being formulated in the composition. In certain embodiments, the purified or isolated component is about or is at least about 95, 96, 97, 98, 99, 99.1, 99.2, 99.3, 99.4, 99.5% pure or more, or any range derivable therein. Such a purified component may then be mixed with other components to form a composition as described herein.

A recombinant StIR protein, e.g., EF2505, or fragment or segment thereof or analog thereof comprises at least, at most, or about 5, 10, 15, 20, 25, 30, 35, 40, 50, 55, 60, 65, 70, 75, 80-, 85, 90, 95, 100, 150 200, 250, 300, 350, 400, 450, 500, 550, 600, 650, 700, 750, 800, 850, 900, 950, 1000, 1500, 1600 or 1651 consecutive amino acids, including all values and ranges there between, of SEQ ID NO:1. In certain aspects, a fragment or analog thereof includes at least or at most or about amino acid sequence from amino acid 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 40, 45, 50, 55, 60, 65, 70, 75, 80, 85, 90, 95, 100, 110, 111, 112, 113, 114, 115, 116, 117, 118, 119, 120 to amino acid 100, 150, 200, 250, 300, 350, 355, 360, 365, 370, 375, 380, 390, 395, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450 of SEQ ID NO:1, including all values and ranges there between. In a further aspect, a polypeptide fragment or analog thereof includes, but is not limited to an amino acid sequence comprising at least, at most, or about amino acids 20, 21, 22, 23, 24, 25, 26, 27, 28, 29, 30 to amino acid 440, 441, 442, 443, 444, 445, 446, 447, 448, 449, 450 of SEQ ID NO:1. In certain aspects, a polypeptide segment or fragment or analog thereof includes, but is not limited to an amino acid sequence comprising at least or at most or about amino acids 28, 29, 30, 35, 40, 45, 50, 55, 60, 65, 70, 75, 80, 85, 90, 95, 100, 110, 120, 130, 140, 150, 200, 250, to amino acid 440, 441, 442, 443, 444, 445, 446, 447, 448, 449, 450 of SEQ ID NO:1, including all values and ranges there between. In yet a further aspect, a polypeptide fragment or analog thereof comprises an amino acid sequence comprising an amino acid sequence that is at least 70, 75, 80, 85, 90, 95, 96, 97, 98, 99 or 100% identical to amino acid 28 to 449, 28 to 442, 111 to 449, 111 to 442, 223 to 449, or 223 to 442 of SEQ ID NO:1, including all values and ranges there between. Derivatives or variants of the StIR protein or its segments includes insertion, deletion, and point mutations. A particular insertional mutation is a fusion protein that comprises amino acid sequence exogenous to the EF2505 protein at the carboxy or amino terminus.

In certain aspects, the StIR protein or a fragment or a segment or a derivative thereof is administered in a nebulized or aerosolized formulation. The composition can be administer by inhalation or inspiration. The StIR or a fragment of derivative thereof can be administered in an amount of from about 0.01, 0.05. 0.1, 0.5, 1, 5, 10, 15, 20, 25, 30, 35, 40, 45, 50, 55, 60, 65, 70 μg or mg/kg to about 55, 60, 65, 70, 75, 80, 85, 90, 95, 100, 125, 150, 200 μg or mg/kg of the individual's body weight. In other aspect, a subject can be administered about 0.01, 0.05. 0.1, 0.5, 1, 5, 10, 15, 20, 25, 30, 35, 40, 45, 50, 55, 60, 65, 70, 75, 80, 85, 90, 95, 100, 125, 150, 200 μg or mg or StIR polypeptide or peptide or variant or derivative or analog thereof. Based on the following disclosure, a person having ordinary skill in this art would readily be able to determine useful segments, fragments, or derivatives of a StIR polypeptide, e.g., *Enterococcus faecalis* protein EF2505. In one preferred aspect, the fragment, segment, or derivative is at least 75% identical to a sequence of SEQ ID NO:1. In another aspect, the fragment, segment, or derivative is at least 80% identical to a sequence of SEQ ID NO:1. In another aspect, the fragment, segment, or derivative is at least 85% identical to a sequence of SEQ ID NO:1. In another aspect, the fragment, segment, or derivative is at least 90% identical to a sequence of SEQ ID NO:1. In another aspect, the fragment, segment, or derivative is at least 95% identical to a sequence of SEQ ID NO:1.

In yet another embodiment, the present invention is directed to a pharmaceutically acceptable composition comprising one or more StIR polypeptide (e.g., *Enterococcus faecalis* protein EF2505) or a fragment or a segment or a derivative or an analog thereof; an anti-inflammatory agent; an anti-microbial agent; and/or one or more pharmaceutical excipients. Typically such compositions are sterile and essentially free of pathogenic microbes.

b. Flagellin

In certain aspects the StIR composition comprises a flagellin polypeptide comprising 10, 11, 12, 13, 14, 15, 16, 17, 18, 19, 20, 21, or 22 consecutive amino acids of the peptide QRLSTGSRINSAKDDAAGLQIA (SEQ ID NO:2), which is known as a TLR5 agonist, or a segment or derivative thereof. A polypeptide of the invention can also comprise an amino acid sequence that is at least 70, 80, or 90%, including all values and ranges there between, identical to SEQ ID NO:2) In other aspects, flagellin is synthesized and/or purified or isolated flagellin polypeptide or peptide. The term "purified" or "isolated" means that component was previously isolated away or purified from other proteins or synthesis reagents or byproducts and that the component is at least about 95% pure prior to being formulated in the composition. In certain embodiments, the purified or isolated component is about or is at least about 80, 95, 96, 97, 98, 99, 99.1, 99.2, 99.3, 99.4, 99.5% pure or more, or any range derivable therein. Such a purified component may then be mixed with other components to form a composition as described herein.

A recombinant flagellin protein or fragment or segment thereof comprises 5, 10, 15, 20, 21, 22, 23, 24, 25, 30, 35, 40, 50, 55, 60, 65, 70, 75, 80, 85, 90, 95, 100, 150 200, 250, 300, 350, or 400 consecutive amino acids, including all values and ranges there between, of SEQ ID NO:2 or other flagellin polypeptides. These fragments or segments are at least, at most, or about 70, 75, 80, 85, 90, 95, 96, 97, 98, 99 or 100% identical to SEQ ID NO:2 or other falgellin polypetides. In certain aspects, a flagellin polypeptide or segment is at least 75% identical to the sequence of SEQ ID NO:2. In another aspect, flagellin polypeptide or segment is at least 80% identical to the sequence of SEQ ID NO:2. In another aspect, the flagellin polypeptide or segment is at least 85% identical to the sequence of SEQ ID NO:2. In another aspect, the flagellin polypeptide or segment is at least 90% identical to the sequence of SEQ ID NO:2. In another aspect, the flagellin polypeptide or segment is at least 95% identical to the sequence of SEQ ID NO:2. Derivatives or variants of flagellin or its segment includes insertion, deletion, and point mutations of SEQ ID NO:2. A particular insertional mutation is a fusion protein that comprises amino acid sequence exogenous to flagellin at the carboxy or amino terminus. A number of flagellin proteins are known in the and include, but are not limited to flagellin having accession number BAB58984 (gi|14278896); YP_001330159 (gi|150402865); YP_001323483 (gi|150399716); CAA28975 (gi|1333716); CAA02137 (gi|1567895); CAA67105 (gi|1580779); AAR10473 (gi|38049688); CAR58992 (gi|197093531); YP_001217666 (gi|147675484); CAL12564 (gi|122089712); BAD14977 (gi|46093563); or CAD05707 (gi|16503200), each of which is incorporated herein by reference in its entirety as of the priority date of this application.

c. Microbial Lysate

Embodiments of the invention also include pharmaceutically acceptable compositions comprising a lysate of an essentially non-pathogenic microbe, an anti-inflammatory agent and one or more pharmaceutical excipients, wherein said composition is sterile and essentially free of pathogenic microbes. A microbial lysate is typically sonicated; homogenized; irradiated; lysed by barometric, pneumatic, detergents, or enzymatic methods and combinations thereof. In a particular aspect the microbial lysate is UV irradiated before, during, or after lysis. The microbial lysate can include, but is not limited to a bacterial, fungal, or viral lysate. In certain embodiments the microbial lysate is a bacterial lysate. The microorganism from which the lysate is prepared need not be a virulent microorganism, and typically will not be a virulent microorganism. Aspects of the invention include a lysate derived from bacteria having a limited effect on the health of a subject. Limited effect refers to producing minimal adverse reactions and insubstantial impairment in the function of a tissue, an organ, or a system of a subject over a period of at least, at most, or about 1, 2, 3, 4, 5, 6, 7, 8, 9, or 10 days.

Compositions of the invention need not be derived directly from a virulent organism from which protection or therapy is sought. The bacteria can be from the genus *Haemophilus*, but is not limited to *Haemophilus*. Bacteria that pose a minimal threat of adverse effects in a subject can be identified. In certain aspects the bacteria is *Haemophilus influenzae*, particularly non-typeable *Haemophilus influenzae* (NTHi) (Clement et al., 2008; Clement et al., 2009; Evans et al., 2010; Tuvim et al., 2009).

A microbial lysate can have a protein concentration of at least about, about, or at most about 0.5, 1, 1.5, 2, 2.5, 3, 3.5, 4, 4.5, 5, 5.5, 6, 6.5, 7, 7.5, 8, 8.5, 9, 9.5 or 10 mg/ml, including all values and ranges there between. In certain aspects the microbial lysate can have a protein concentration of at least about, about, or at most about 10 mg/ml.

Embodiments of the invention include a microbial lysate that can be administered via the respiratory tract. In certain aspects administration is by inhalation. In a further aspect the composition is aerosolized or in a form that can be inhaled by a subject. In certain embodiments, a lysate composition comprises an anti-inflammatory agent, including steroidal and non-steroidal antiinflammatories (NSAIDs). For further detail see U.S. patent application Ser. No. 11/830,622 "Compositions and methods for stimulation of lung innate immunity" Dickey et al., which is incorporated herein by reference in its entirety.

B. Host or Autolgous Components

A number of molecules derived from cells and tissues of a subject or host can stimulate, enhance or contribute to the production of an immune response. These moieties are referred to as host or autologous moieties or components and include small molecules released from injured, stressed, or dying cells; components involved in microcroial killing or neutralization; cytokines; and macromolecules released from cells or tissues.

1. Small Molecule Host Compounds

Small molecules that are associated or released from cells that are injured, stressed, or dying, such as adenosine 5'-triphosphate (ATP), uric acid (urate), and adenosine. The receptors for many of these molecules and the pathways by which they modulate inflammation are well defined. Inflammation is one of the first responses of the immune system to infection or irritation. Inflammation is stimulated by chemical factors released by injured cells and serves to establish a physical barrier against the spread of infection, and to promote healing of any damaged tissue following the clearance of pathogens. Chemical factors produced during inflammation (histamine, bradykinin, serotonin, leukotrienes also prostaglandins) sensitize pain receptors, cause vasodilation of the blood vessels at the scene, and attract phagocytes, especially neutrophils. Neutrophils then trigger other parts of the immune system by releasing factors that summon other leukocytes and lymphocytes.

Small molecule host components that can be included in the StIR compositions of the invention include ATP, adenosine, histamine, bradykinin, serotonin, leukotrienes, prostaglandins.

2. Extracellular Host Moieties

Extracelllar host proteins having a role in direct microbial killing and/or in signaling, such as complement, pentraxins, defensins, and cathelicidins. These molecules are often present constitutively, but do not signal until they become activated by binding to microbial products, or being proteolytically cleaved, or some other activating mechanism. In addition, their production may be increased. In certain aspects these proteins are either in an activated form (either by in vitro activiation or processing, or by engineering of the protein).

The complement system is a biochemical cascade that helps clear pathogens from an organism. It is part of the larger immune system that is not adaptable and does not change over the course of an individual's lifetime; as such it belongs to the innate immune system. However, it can be recruited and brought into action by the adaptive immune system.

The complement system consists of a number of small proteins found in the blood, normally circulating as inactive zymogens. When stimulated by one of several triggers, proteases in the system cleave specific proteins to release cytokines and initiate an amplifying cascade of further cleavages. The end-result of this activation cascade is massive amplification of the response and activation of the cell-killing membrane attack complex. Over 20 proteins and protein fragments make up the complement system, including serum proteins, serosal proteins, and cell membrane receptors. These proteins are synthesized mainly in the liver, and they account for about 5% of the globulin fraction of blood serum.

Components of the complement system that can be included in a StIR composition include, but are not limited to C1-complex, (C1q, C1r, C1s and C1qr2s2), C1r2s2, C4, C2, C4a, C4b, C2a, C2b C3-convertase (C4b2a complex), C3a, C3b; C5 convertase (C4bC2aC3b complex), Decay accelerating factor (DAF), factor B, C3bB, factor D, Ba, Bb, C3bBb, C3bBbC3b, C5, C5a, C5b, C6, C7, C8, C9, and membrane attack complex (MAC) (C5b6789).

The Pentraxins are a family of proteins typically having calcium dependent ligand binding and a distinctive flattened β-jellyroll structure similar to that of the legume lectins. The "short" pentraxins include Serum Amyloid P component (SAP) and C reactive protein (CRP). The "long" pentraxins include PTX3 (a cytokine modulated molecule) and several neuronal pentraxins.

Defensins are small cysteine-rich cationic proteins found in both vertebrates and invertebrates. They are active against bacteria, fungi and many enveloped and nonenveloped viruses. They consist of 18-45 amino acids including six (in vertebrates) to 8 conserved cysteine residues. Cells of the immune system contain these peptides to assist in killing phagocytized bacteria, for example in neutrophil granulocytes and almost all epithelial cells. Most defensins function by binding to microbial cell membrane, and once embedded, forming pore-like membrane defects that allow efflux of essential ions and nutrients.

Defensin can be included in StIR compositions of the invention include, but are not limited to α-defensins (DEFA1, DEFA1A3, DEFA3, and/or DEFA4), β-defensins (DEFB1, DEFB4, DEFB103A/DEFB103B to DEFB107A/DEFB107B, DEFB110 to DEFB133), and/or θ-defensins (DEFT1P).

Cathelicidin antimicrobial peptide is a family of polypeptides found in lysosomes in polymorphonuclear leukocytes (PMNs). Members of the cathelicidin family of antimicrobial polypeptides are characterized by a highly conserved region (cathelin domain) and a highly variable cathelicidin peptide domain. Cathelicidin peptides have been isolated from many different species of mammals. Cathelicidins were originally found in neutrophils but have since been found in many other cells including epithelial cells and macrophages activated by bacteria, viruses, fungi, or the hormone 1,25-D. The cathelicidin family shares primary sequence homology with the cathepsin family of cysteine proteinase inhibitors, although amino acid residues thought to be important in such protease inhibition are usually lacking.

3. Cytokines

Cytokines are a category of signaling molecules that are used extensively in cellular communication. They are proteins, peptides or glycoproteins. The term cytokine encompasses a large and diverse family of polypeptide regulators that are produced widely throughout the body by cells of diverse embryological origin. The action of cytokines may be autocrine, paracrine, and endocrine. Cytokines are critical to the development and functioning of both the innate and adaptive immune response, although not limited to just the immune system. They are often secreted by immune cells that have encountered a pathogen, thereby activating and recruiting further immune cells to increase the system's response to the pathogen.

Cytokines that stimulate antimicrobial defenses of innate immune cells, in particular epithelial cells, such as IL-17, IL-22, IFN-γ. In some cases, this represents an amplification of innate inflammation by the adaptive innate immune system, as when IL-17 is produced by Th 17 cells. In other cases, cytokines are released by cells that are not part of the adaptive immune system, for example by epithelial cells, mesenchymal cells, or dendritic cells.

Cytokines that can be included in the StIR compositions of the invention include the IL-1 superfamily 1 ((IL-1Ra), IL-18, IL-33); the IL-6 like/gp130 utilizing family (IL-6, IL-11, IL-27, IL-30, IL-31, Oncostatin M, Leukemia inhibitory factor, Ciliary neurotrophic factor, Cardiotrophin 1); the IL-10 family (IL-10, IL-19, IL-20, IL-22, IL-24, IL-26); Interferon type III (IL-28, IL-29); Common γ-chain family (IL-2/15, IL-3, IL-4, IL-7, IL-9, IL-13, IL-21); the IL-12 family (IL-12, IL-23, IL-27, IL-35), IL-5; IL-8; IL-14; IL-16; IL-17/25; IL-32; the CCL chemokines (CCL1, CCL2, CCL3, CCL4, CCL5, CCL6, CCL7, CCL8, CCL9, CCL10, CCL11, CCL12, CCL13, CCL14, CCL15, CCL16, CCL17, CCL18, CCL19, CCL20, CCL21, CCL22, CCL23, CCL24, CCL25, CCL26, CCL27, CCL28); The CXCL chemokines (CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, CXCL17); CX3CL-1; XCL1; XCL 2; TNF (ligand) superfamily (4-1BB ligand, B-cell activating factor, FAS ligand, Lymphotoxin, OX40L, RANKL, TRAIL); Cluster of differentiation cytokines (CD70, CD153, CD154); Interferons (IFN-I alpha (Pegylated 2a, Pegylated 2b), IFN-Ibeta (1a, 1b)), IFN-IIγ, and IFN-III.

4. Macromolecular Host Moieties

Macromolecules or fragments thereof that can be released from the extracellular matrix, the cell surface, or the cell interior and activate innate inmmune signaling, such as dectin, versican, HMGB-I, DNA and RNA. Typically, these macromolecules are normally concealed from target receptors, either within the cell interior, or masked by intramolecular or intermolecular interactions. They are released to interact with target receptors after cell disruption, or after proteolysis of the cell surface of the matrix to reveal a signaling moiety, or some similar mechanism.

II. POLYPEPTIDE AND PEPTIDE COMPOSITIONS

In certain embodiments, the present invention concerns at least one polypeptide or peptide (e.g., a polypeptide segment) or derivative or variant thereof. As used herein, a "protein," "polypeptide," "peptide," "polypeptide or peptide composition," or "polypeptide or peptide compound," generally refers, but is not limited to, a protein or polypeptide of at least five amino acids or amino acid analogs (collectively an amino molecule, see below). All the "polypeptide or peptide" terms described above may be used interchangeably herein.

In certain embodiments the size of the at least one polypeptide or peptide molecule may comprise, but is not limited to, a molecule having at least, at most, or about 5, 10, 11, 12, 13, 14, 15, 16, 17, 18, 19, 20, 21, 22, 23, 24, 25, 26, 27, 28, 29, 30, 40, 50, 100, 500, 1000 to about 10, 11, 12, 13, 14, 15, 16, 17, 18, 19, 20, 21, 22, 23, 24, 25, 26, 27, 28, 29, 30, 40, 50, 100, 500, or greater amino molecule residues, and any value or range derivable therein. The invention includes those lengths of contiguous amino acids or analogs thereof of any sequence discussed herein.

Segments or fragment of a polypeptide or peptide include amino acid 1, 2, 3, 4, 5, 6, 7, 8, 9, 10, 15, 20, 30, 40, 50, 60, 70, 80, 90, 100, 150, 200, 300, 350, 400, 450, to amino acid 10, 15, 20, 30, 40, 50, 60, 70, 80, 90, 100, 150, 200, 300, 350, 400, 450, 500, 550, 600 amino acids of sequences disclosed or referenced herein, including all values and ranges there between.

As used herein, an "amino molecule" refers to any amino acid, amino acid derivative or amino acid mimic as known to one of ordinary skill in the art. In certain embodiments, the residues of the polypeptide or peptide molecule are sequential, without any non-amino molecule interrupting the sequence of amino molecule residues. In other embodiments, the sequence may comprise one or more non-amino molecule moieties. In certain embodiments, the sequence of residues of the polypeptide or peptide molecule may be interrupted by one or more non-amino molecule moieties.

Accordingly, the term "polypeptide or peptide composition" encompasses amino molecule sequences comprising at least one of the 20 common amino acids in naturally synthesized proteins, or at least one modified or unusual amino acid.

In certain embodiments the polypeptide or peptide composition comprises at least one protein, polypeptide or peptide. In methods that involve a TLR agonist composition a polypeptide or peptide can have all or part of the amino acid sequence of a flagellin polypeptide, such as SEQ ID NO:2 or homologous polypeptides. In certain embodiments, protein, polypeptide, or peptide containing compositions will generally be proteins or peptides or synthetic proteins or peptides each essentially free from toxins, pathogens, and harmful immunogens. In certain aspects the polypeptide is a recombinant or synthetic amino acid sequence.

Polypeptide or peptide compositions may be made by any technique known to those of skill in the art, including the expression of proteins, polypeptides or peptides through standard molecular biological techniques, the isolation of polypeptides or peptides from natural sources, or the chemical synthesis of polypeptide or peptide materials. The coding regions for these polypeptides or peptides may be amplified and/or expressed using the techniques disclosed herein or as would be know to those of ordinary skill in the art. Alternatively, various commercial preparations of proteins, polypeptides and peptides are known to those of skill.

In certain embodiments a polypeptide or peptide compound may be purified. Generally, "purified" will refer to a specific or protein, polypeptide, or peptide composition that has been subjected to fractionation to remove various other proteins, polypeptides, peptides, and other molecules and compounds, and which composition substantially retains its activity, as may be assessed, for example, by protein assays, as known to one of ordinary skill in the art for the specific or desired protein, polypeptide or peptide.

It is contemplated that virtually any protein, polypeptide or peptide containing component may be used in the compositions and methods disclosed herein. In certain embodiments, it is envisioned that the formation of a aerosol or nebulized or aerosolizable or nebulizable composition can allow the composition to be more precisely or easily applied to the respiratory system by inhalation, inspiration, and the like.

A. Polypeptide or Peptide Variants and Derivatives

Amino acid sequence variants or derivatives of the proteins, polypeptides and peptides of the present invention can be substitutional, insertional or deletion variants, as well as inclusion of amino acid analogs or derivatives. Deletion variants lack one or more residues of the native protein that are not essential for function or immunogenic activity. Another common type of deletion variant is one lacking secretory signal sequences or signal sequences directing a protein to bind to a particular part of a cell or membrane spanning regions or other functional sequences not needed for the in vivo activity sought. Insertional mutants typically involve the addition of material at a non-terminal point in the polypeptide. This may include the insertion of an immunoreactive epitope or simply a single residue. Terminal additions, called fusion proteins, are discussed below.

Substitutional variants typically contain the exchange of one amino acid for another at one or more sites within a polypeptide or peptide, and may be designed to modulate one or more properties, such as stability against proteolytic cleavage, without the loss of other functions or properties. Substitutions of this kind preferably are conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

The term “biologically functional equivalent” is well understood in the art and is further defined in detail herein. Accordingly, a biologically functional equivalent will have a sequence of about 70, 75, 80, 85, 90, 95, 96, 97, 98, 99% of amino acids that are identical or functionally equivalent to the amino acids of a polypeptide or peptide or variant or analog or derivative thereof and provide a similar biological activity/response to flagellin or other TLR agonist.

The following is a discussion based upon changing of the amino acids of a polypeptide or peptide to create an equivalent, or even an improved, second-generation molecule. For example, certain amino acids may be substituted for other amino acids in a polypeptide or peptide without appreciable loss of a particular activity such as, enhancement of immunologic response. Since it is the interactive capacity and nature of a polypeptide or peptide that typically defines a protein’s functional activity, certain amino acid substitutions can be made in a polypeptide or peptide sequence, and in its underlying DNA coding sequence, and nevertheless produce a protein with like properties. It is thus contemplated by the inventors that various changes may be made in the DNA sequences encoding polypeptides or peptides of the invention without appreciable loss of their biological utility or activity, as discussed below.

In making such changes, the hydropathic index of amino acids may be considered. The importance of the hydropathic amino acid index in conferring interactive biologic function on a protein is generally understood in the art (Kyte & Doolittle, 1982). It is accepted that the relative hydropathic character of the amino acid contributes to the secondary structure of the resultant protein, which in turn defines the interaction of the protein with other molecules, cells, tissue and the like, for example, enzymes, substrates, receptors, DNA, antibodies, antigens, immunologic cells and systems, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine*−0.5); cysteine (−1.0); methionine (−1.3); valine (−1.5); leucine (−1.8); isoleucine (−1.8); tyrosine (−2.3); phenylalanine (−2.5); tryptophan (−3.4).

It is also understood that an amino acid can be substituted for another having a similar hydrophilicity value and still produce a biologically equivalent and immunologically equivalent protein. In such changes, the substitution of amino acids whose hydrophilicity values are within ±2 is preferred, those that are within ±1 are particularly preferred, and those within ±0.5 are even more particularly preferred.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

One can also modify the internal amino acids, and/or amino and/or carboxy termini of polypeptide or peptide compounds of the invention to produce other compounds of the invention, i.e., polypeptide or peptide derivatives. Amino terminus modifications include methylation (e.g., $—NHCH_3$ or $—N(CH_3)_2$), acetylation (e.g., with acetic acid or a halogenated derivative thereof such as α-chloroacetic acid, α-bromoacetic acid, or α-iodoacetic acid), adding a benzyloxycarbonyl (Cbz) group, or blocking the amino terminus with any blocking group containing a carboxylate functionality defined by RCOO— or sulfonyl functionality defined by $R—SO_2—$, where R is selected from alkyl, aryl, heteroaryl, alkyl aryl, and the like, and similar groups. One can also incorporate a desamino acid at the N-terminus (so that there is no N-terminal amino group) to decrease susceptibility to proteases or to restrict the conformation of the polypeptide or peptide compound.

Carboxy terminus modifications include replacing the free acid with a carboxamide group or forming a cyclic lactam at the carboxy terminus to introduce structural constraints. One can also cyclize the peptides of the invention, or incorporate a desamino or descarboxy residue at the termini of the peptide, so that there is no terminal amino or carboxyl group, to decrease susceptibility to proteases or to restrict the conformation of the peptide. C-terminal functional groups of the compounds of the present invention include amide, amide lower alkyl, amide di(lower alkyl), lower alkoxy, hydroxy, and carboxy, and the lower ester derivatives thereof, and the pharmaceutically acceptable salts thereof.

One can replace the naturally occurring side chains of the 20 genetically encoded amino acids (or the stereoisomeric D amino acids) with other side chains, for instance with groups such as alkyl, lower alkyl, cyclic 4-, 5-, 6-, to 7-membered alkyl, amide, amide lower alkyl, amide di(lower alkyl), lower alkoxy, hydroxy, carboxy and the lower ester derivatives thereof, and with 4-, 5-, 6-, to 7-membered heterocyclic. In particular, proline analogues in which the ring size of the proline residue is changed from 5 members to 4, 6, or 7 members can be employed. Cyclic groups can be saturated or unsaturated, and if unsaturated, can be aromatic or non-aromatic. Heterocyclic groups preferably contain one or more nitrogen, oxygen, and/or sulfur heteroatoms. Examples of such groups include the furazanyl, furyl, imidazolidinyl, imidazolyl, imidazolinyl, isothiazolyl, isoxazolyl, morpholinyl (e.g. morpholino), oxazolyl, piperazinyl (e.g., 1-piperazinyl), piperidyl (e.g., 1-piperidyl, piperidino), pyranyl, pyrazinyl, pyrazolidinyl, pyrazolinyl, pyrazolyl, pyridazinyl, pyridyl, pyrimidinyl, pyrrolidinyl (e.g., 1-pyrrolidinyl), pyrrolinyl, pyrrolyl, thiadiazolyl, thiazolyl, thienyl, thiomorpholinyl (e.g., thiomorpholino), and triazolyl. These heterocyclic groups can be substituted or unsubstituted. Where a group is substituted, the substituent can be alkyl, alkoxy, halogen, oxygen, or substituted or unsubstituted phenyl.

One can also readily modify polypeptides or peptides by phosphorylation, and other methods (e.g., as described in Hruby et al. (1990).

The peptide compounds of the invention also serve as structural models for non-peptidic compounds with similar biological activity. Those of skill in the art recognize that a variety of techniques are available for constructing compounds with the same or similar desired biological activity as the lead peptide compound, but with more favorable activity than the lead with respect to solubility, stability, and susceptibility to hydrolysis and proteolysis (See, Morgan and Gainor, 1989). These techniques include replacing the peptide backbone with a backbone composed of phosphonates, amidates, carbamates, sulfonamides, secondary amines, and N-methylamino acids.

Furthermore, the compounds of the present invention may contain one or more intramolecular disulfide bonds. In one embodiment, a peptide monomer or dimer comprises at least one intramolecular disulfide bond. In preferred embodiments, a peptide dimer comprises two intramolecular disulfide bonds. Such disulfide bonds may be formed by oxidation of the cysteine residues of the peptide core sequence. In one embodiment the control of cysteine bond formation is exercised by choosing an oxidizing agent of the type and concentration effective to optimize formation of the desired isomer. For example, oxidation of a peptide dimer to form two intramolecular disulfide bonds (one on each peptide chain) is preferentially achieved (over formation of intermolecular disulfide bonds) when the oxidizing agent is DMSO. In certain embodiments, the formation of cysteine bonds is controlled by the selective use of thiol-protecting groups during peptide synthesis.

Other embodiments of this invention provide for analogs of these disulfide derivatives in which one of the sulfurs has been replaced by a $CH_2$ group or other isotere for sulfur. These analogs can be prepared from the compounds of the present invention, wherein each core sequence contains at least one Cys (C) or homocysteine residue and an α-amino-γ-butyric acid in place of the second C residue, via an intramolecular or intermolecular displacement, using methods known in the art (See, e.g., Barker et al., 1992 and Or et al., 1991). One of skill in the art will readily appreciate that this displacement can also occur using other homologs of α-amino-γ-butyric acid and homocysteine.

In addition to the foregoing cyclization strategies, other non-disulfide peptide cyclization strategies can be employed. Such alternative cyclization strategies include, for example, amide-cyclization strategies as well as those involving the formation of thio-ether bonds. Thus, the compounds of the present invention can exist in a cyclized form with either an intramolecular amide bond or an intramolecular thio-ether bond. For example, a peptide may be synthesized wherein one cysteine of the core sequence is replaced with lysine and the second cysteine is replaced with glutamic acid. Thereafter a cyclic monomer may be formed through an amide bond between the side chains of these two residues. Alternatively, a peptide may be synthesized wherein one cysteine of the core sequence is replaced with lysine. A cyclic monomer may then be formed through a thio-ether linkage between the side chains of the lysine residue and the second cysteine residue of the core sequence. As such, in addition to disulfide cyclization strategies, amide-cyclization strategies and thio-ether cyclization strategies can both be readily used to cyclize the compounds of the present invention. Alternatively, the amino-terminus of the peptide can be capped with an α-substituted acetic acid, wherein the α-substituent is a leaving group, such as an α-haloacetic acid, for example, α-chloroacetic acid, α-bromoacetic acid, or α-iodoacetic acid.

Included with the below description, the U.S. patent application Ser. No. 10/844,933 filed May 12, 2004, is incorporated by reference herein in its entirety. Water-soluble polymers, such as polyethylene glycol (PEG), can be used for the covalent modification of polypeptides or peptides of therapeutic importance. Attachment of such polymers is thought to enhance biological activity, increase aqueous solubility, and enhance resistance to protease digestion. For example, covalent attachment of PEG to therapeutic polypeptides such as interleukins (Knauf, et al., 1988; 15064; Tsutsumi et al., 1995, interferons (Kita et al., 1990), catalase (Abuchowski et al., 1977, superoxide dismutase (Beauchamp et al., 1983, and adenosine deaminase (Chen et al., 1981), has been reported to extend their half life in vivo, and/or reduce their immunogenicity and antigenicity.

The compounds of the invention may further comprise one or more water soluble polymer moieties. Preferably, these polymers are covalently attached to the compounds. The water soluble polymer may be, for example, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), poly(n-vinyl pyrrolidone)polyethylene glycol, propropylene glycol homopolymers, polypropylene oxide/ethylene oxide copolymers, and polyoxyethylated polyols.

Compounds of the invention can be attached to water-soluble polymers (e.g., PEG) using any of a variety of chemistries to link the water-soluble polymer(s) to the receptor-binding portion of the molecule (e.g., peptide+spacer). A typical embodiment employs a single attachment junction for covalent attachment of the water soluble polymer(s) to the receptor-binding portion, however in alternative embodiments multiple attachment junctions may be used, including further variations wherein different species of water-soluble polymer are attached to the receptor-binding portion at distinct attachment junctions, which may include covalent attachment junction(s) to the spacer and/or to one or both peptide chains.

PEG reagents include, but are not limited to mPEG2-NHS, mPEG2-ALD, multi-Arm PEG, mPEG(MAL)$_2$, mPEG2 (MAL), mPEG-NH$_2$, mPEG-SPA, mPEG-SBA, mPEGthioesters, mPEG-Double Esters, mPEG-BTC, mPEG-ButyrALD, mPEG-ACET, heterofunctional PEGs (NH$_2$-PEG-COOH, Boc-PEG-NHS, Fmoc-PEG-NHS, NHS-PEG-VS, NHS-PEG-MAL), PEG acrylates (ACRL-PEG-NHS), PEG-phospholipids (e.g., mPEG-DSPE), multiarmed PEGs of the SUNBRITE series including the GL series of glycerine-based PEGs activated by a chemistry chosen by those skilled in the art, any of the SUNBRITE activated PEGs (including but not limited to carboxyl-PEGs, p-NP-PEGs, Tresyl-PEGs, aldehyde PEGs, acetal-PEGs, amino-PEGs, thiol-PEGs, maleimido-PEGs, hydroxyl-PEG-amine, amino-PEG-COOH, hydroxyl-PEG-aldehyde, carboxylic anhydride type-PEG, functionalized PEG-phospholipid, and other similar and/or suitable reactive PEGs as selected by those skilled in the art for their particular application and usage.

The number of polymer molecules attached may vary; for example, one, two, three, or more polymers may be attached to a polypeptide or peptide of the invention. The multiple attached polymers may be the same or different chemical moieties (e.g., PEGs of different molecular weight). In some cases, the degree of polymer attachment (the number of polymer moieties attached to a peptide and/or the total number of peptides to which a polymer is attached) may be influenced by the proportion of polymer molecules versus peptide molecules in an attachment reaction, as well as by the total concentration of each in the reaction mixture. In general, the optimum polymer versus peptide ratio (in terms of reaction efficiency to provide for no excess unreacted peptides and/or polymer moieties) will be determined by factors such as the desired degree of polymer attachment (e.g., mono, di-, tri-, etc.), the molecular weight of the polymer selected, whether the polymer is branched or unbranched, and the reaction conditions for a particular attachment method.

In other aspects, a compound of the invention can be derivatized by the addition of water insoluble polymers. Representative water-insoluble polymers include, but are not limited to, polyphosphazines, poly(vinyl alcohols), polyamides, polycarbonates, polyalkylenes, polyacrylamides, polyalkylene glycols, polyalkylene oxides, polyalkylene terephthalates, polyvinyl ethers, polyvinyl esters, polyvinyl halides, polyvinylpyrrolidone, polyglycolides, polysiloxanes, polyurethanes, poly(methyl methacrylate), poly(ethyl methacrylate), poly(butyl methacrylate), poly(isobutyl methacrylate), poly(hexyl methacrylate), poly(isodecyl methacrylate), poly (lauryl methacrylate), poly(phenyl methacrylate), poly(methyl acrylate), poly(isopropyl acrylate), poly(isobutyl acrylate), poly(octadecyl acrylate) polyethylene, polypropylene, poly(ethylene glycol), poly(ethylene oxide), poly (ethylene terephthalate), poly(vinyl acetate), polyvinyl chloride, polystyrene, polyvinyl pyrrolidone, pluronics and polyvinylphenol and copolymers thereof.

Synthetically modified natural polymers of use in derivatives of the invention include, but are not limited to, alkyl celluloses, hydroxyalkyl celluloses, cellulose ethers, cellulose esters, and nitrocelluloses. Members of the broad classes of synthetically modified natural polymers include, but are not limited to, methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose, cellulose triacetate, cellulose sulfate sodium salt, and polymers of acrylic and methacrylic esters and alginic acid.

In certain aspects a polypeptide or peptide of the invention can be modified or derivatized by addition of saccharide groups, or modified sugars. The present invention provides for polypeptide and peptide derivatives that contain modified sugars, modified sugar nucleotides and conjugates of the modified sugars. In modified sugar compounds of the invention, the sugar moiety is preferably a saccharide, a deoxysaccharide, an amino-saccharide, or an N-acyl saccharide. The term "saccharide" and its equivalents, "saccharyl," "sugar," and "glycosyl" refer to monomers, dimers, oligomers and polymers. The sugar moiety can also be functionalized with a modifying group. The modifying group is conjugated to the sugar moiety, typically, through conjugation with an amine, sulfhydryl or hydroxyl, e.g., primary hydroxyl, moiety on the sugar. In one embodiment, the modifying group is attached through an amine moiety on the sugar, e.g., through an amide, a urethane or a urea that is formed through the reaction of the amine with a reactive derivative of the modifying group.

Any sugar can be utilized as the sugar for conjugates of the invention. Such sugars include, but are not limited to, glucose, galactose, mannose, fucose, and sialic acid. Other useful sugars include amino sugars such as glucosamine, galactosamine, mannosamine, the 5-amine analogue of sialic acid and the like. The sugar can be a structure found in nature or it can be modified to provide a site for conjugating an additional modifying group.

Those of skill in the art will recognize that the structures and compositions set forth are generally applicable across the genus of saccharide groups, modified saccharide groups, activated modified saccharide groups and conjugates of modified saccharide groups.

III. STIMULATION OF LUNG DEFENSES

The inventors have used the mouse as model for microbial infection of the lung. In certain studies, untreated mice have mortality of 100%, but treated mice are highly protected. Not be held to any particular mechanism or theory, it is believed that protection is due to activation of local defenses or innate immunity. The effects of single and repetitive exposure of a subject to a composition of the invention have been determined and no obvious gross pathology, such as premature death, weight loss, or behavioral changes have been observed.

One non-limiting benefit of the present invention is that it can be delivered and have effect quickly and easily. Also, the compositions can be produced economically in large quantities and easily stored, as well as easily transported by a person outside of a hospital setting. Typically, the administration of the inventive compositions and the methods of the invention result in at least some killing or inhibition of the invading pathogens even before cellular entry. In the case that some pathogens do enter cells in the lungs either by escaping extracellular killing or because the compositions are administered after pathogen exposure (preemptively) instead of before pathogen exposure (preventatively), it is contemplated that the compositions and related methods promote intracellular killing resulting from the enhanced or augmented local responses in the lungs. The compositions and related methods are contemplated to have or produce protective or therapeutic responses against a variety of respiratory pathogens.

The protection or therapy afforded an individual by a StIR composition may be extended to additional classes of microbial pathogens including gram negative bacteria, intracellular bacteria, fungi, and viruses because of the broad activity of the antimicrobial mechanisms of the respiratory tract. An agent such as that described in this application would simplify countermeasure stockpiling and deployment. Also, the compositions and methods of the invention would eliminate the difficulty of rapidly identifying a specific pathogen during a bioweapon attack or other exposure or potential exposure event.

In addition, the economic advantages of producing and purchasing an agent with applicability in multiple civilian and biodefense settings are significant. Augmenting local epithelial mechanisms is particularly attractive in subjects who often have neutropenia or impaired adaptive immune function, e.g., immune compromised subjects. The methods typically act locally rather than systemically, and provide broad effects against multiple pathogens. The effects are rapid and are attractive in a biodefense, medical, and epidemic setting.

Augmentation of innate defense capabilities of the lungs in normal hosts would be valuable during influenza or emergent respiratory viral epidemics for which adaptive immune vaccines are not available. Bacterial outbreaks with emergent or drug-resistant organisms might also be a situation in which boosting innate lung defenses could be helpful. Similarly, protection of caregivers during an epidemic would facilitate care of the sick while limiting spread.

Many people in the community live with chronically compromised defenses against infection, such as patients with diabetes and patients taking immunosuppressive drugs for autoimmune diseases or to prevent transplant rejection. These people might particularly benefit from augmentation of lung defenses during epidemics or times where potential for exposure to microbes is elevated. Even more strikingly, cancer patients undergoing chemotherapy who have transient but severely compromised immune defenses might benefit from transient protection. Pneumonia is a common occurrence in these patients, and is the leading cause of infectious death. Many chemotherapy drugs, such as alkylating agents and nucleoside analogs, cause severe transient neutropenia. Initially, neutropenic patients are susceptible to bacterial pneumonia from organisms seen in normal hosts, as well as bacteria of low virulence such as *Stenotrophomonas maltophilia*. With prolonged neutropenia, patients also become susceptible to infection with fungi of low virulence, particularly *Aspergillus* species.

Defenses of the lung can be stimulated to provide transient protection during prolonged periods of neutropenia. Other cancer patients, such as those receiving fludarabine or anti-lymphocyte antibodies, or those receiving calcineurin inhibitors and steroids after hematopoietic stem cell transplantation, have impaired adaptive immunity. These patients might also benefit from episodic stimulation of lung immunity to protect against invasion by fungi and bacteria that have colonized the airways, or to protect against epidemic viruses. Community outbreaks of seasonal respiratory "cold" viruses such as parainfluenza and RSV can cause fatal pneumonia in these compromised patients, and infection with many of these viruses can be rapidly identified from nasal washings.

Upon infection, recognition of microorganisms is primarily mediated by a set of germline-encoded molecules on innate immune cells that are referred to as pattern recognition receptors (PRRs) (Medzhitov and Janeway, 1997). These pattern recognition receptors are expressed as either membrane-bound or soluble proteins that recognize invariant molecular structures, called pathogen-associated molecular patterns (PAMPs) (Janeway and Medzhitov, 2002). Pathogen-associated molecular patterns are unique, conserved, and essential microbial components, such as LPS, that are structurally different from host molecules (Medzhitov and Janeway, 1997; Janeway and Medzhitov, 2002).

Most multicellular organisms possess an "innate immune system" that does not change during the lifetime of the organism. In contrast, adaptive immunity is the responses to pathogens that change and develop during the lifetime of an individual. Organisms that possess an adaptive immunity also possess an innate immunity, and with many of the mechanisms between the systems being common, it is not always possible to draw a hard and fast boundary between the individual components involved in each, despite the clear difference in operation. Higher vertebrates and all mammals have both an innate and an adaptive immune system.

A. Innate Immune System.

The adaptive immune system may take days or weeks after an initial infection to have an effect. However, most organisms are under constant assault from pathogens that must be kept in check by the faster-acting innate immune system. Innate immunity defends against pathogens by rapid responses coordinated through "innate" mechanisms that recognize a wide spectrum of conserved pathogenic components. Most studies of innate immunity have focused on leukocytes such as neutrophils, macrophages, and natural killer cells. However, epithelial cells play key roles in innate defenses that include providing a mechanical barrier to microbial entry, signaling to leukocytes, and directly killing pathogens. Importantly, all these defenses are highly inducible in response to the sensing of microbial and host products. In healthy lungs, the level of innate immune epithelial function is low at baseline. This is indicated by low levels of spontaneous microbial killing and cytokine release, reflecting low constitutive stimulation in the nearly sterile lower respiratory tract when mucociliary clearance mechanisms are functioning effectively. This contrasts with the colon, where bacteria are continuously present and epithelial cells are constitutively activated. Although the surface area of the lungs presents a large target for microbial invasion, activated lung epithelial cells that are closely apposed to deposited pathogens are ideally positioned for microbial killing. (See Evans et al., 2010). Plants and many lower animals do not possess an adaptive immune system, and rely instead on their innate immunity. Substances of both microbial and non-microbial sources are able to stimulate innate immune responses.

The innate immune system, when activated, has a wide array of effector cells and mechanisms. There are several different types of phagocytic cells, which ingest and destroy invading pathogens. The most common phagocytes are neutrophils, macrophages, and dendritic cells. Another cell type, natural killer cells are especially adept at destroying cells infected with viruses. Another component of the innate immune system is known as the complement system. Complement proteins are normally inactive components of the blood. However, when activated by the recognition of a pathogen or antibody, the various proteins are activated to recruit inflammatory cells, coat pathogens to make them more easily phagocytosed, and to make destructive pores in the surfaces of pathogens.

The "first-line" defense includes physical and chemical barriers to infection, such as skin and mucus coating of the gut and airways, physically preventing the interaction between the host and the pathogen. Pathogens, which penetrate these barriers, encounter constitutively-expressed anti-microbial molecules (e.g., lysozyme) that restrict the infection. The "second-line" defense includes phagocytic cells (macrophages and neutrophil granulocytes) that can engulf (phagocytose) foreign substances.

Phagocytosis involves chemotaxis, where phagocytic cells are attracted to microorganisms by means of chemotactic chemicals such as microbial products, complement, damaged cells and white blood cell fragments. Chemotaxis is followed by adhesion, where the phagocyte sticks to the microorganism. Adhesion is enhanced by opsonization, where proteins like opsonins are coated on the surface of the bacterium. This is followed by ingestion, in which the phagocyte extends projections, forming pseudopods that engulf the foreign organism. Finally, the pathogen is digested by the enzymes in the lysosome, involving reactive oxygen species and proteases.

In addition, anti-microbial proteins may be activated if a pathogen passes through a physical barrier. There are several classes of antimicrobial proteins, such as acute phase proteins (e.g., C-reactive protein, which enhances phagocytosis and activates complement when it binds the C-protein of *S. pneumoniae*), lysozyme, and the complement system).

The complement system is a very complex group of serum proteins, which is activated in a cascade fashion. Three different pathways are involved in complement activation: (a) a classical pathway that recognizes antigen-antibody complexes, (b) an alternative pathway that spontaneously activates on contact with pathogenic cell surfaces, and (c) a mannose-binding lectin pathway that recognizes mannose sugars, which tend to appear only on pathogenic cell surfaces. A cascade of protein activity follows complement activation; this cascade can result in a variety of effects, including opsonization of the pathogen, destruction of the pathogen by the formation and activation of the membrane attack complex, and inflammation.

Interferons are also anti-microbial proteins. These molecules are proteins that are secreted by virus-infected cells. These proteins then diffuse rapidly to neighboring cells, inducing the cells to inhibit the spread of the viral infection. Essentially, these anti-microbial proteins act to prevent the cell-to-cell proliferation of viruses.

B. Adaptive Immune System

The adaptive immune system, also called the "acquired immune system," ensures that most mammals that survive an initial infection by a pathogen are generally immune to further illness, caused by that same pathogen. The adaptive immune system is based on dedicated immune cells termed leukocytes (white blood cells) that are produced by stem cells in the bone marrow, and mature in the thymus and/or lymph nodes. In many species, including mammals, the adaptive immune system can be divided into: (a) a humoral immune system that acts against bacteria and viruses in the body liquids (e.g., blood) by means of proteins, called immunoglobulins (also known as antibodies), which are produced by B cells; and (b) a cellular immune system that destroys virus-infected cells (among other duties) with T cells (also called "T lymphocytes"; "T" means they develop in the thymus). The adaptive immune system is typically directed toward a specific pathogen, e.g., vaccination.

IV. MICROBIAL ORGANISMS

Embodiments of the invention include compositions and related methods for a broad protection against a variety of pathogens or potential pathogens (e.g., NIAID Category A, B, and C priority pathogens). For example, bacterial pneumonia in a normal host occurs at a rate of 1/100 persons/year, mostly in elderly adults and young children and can be caused by a variety of organisms. It is most commonly caused by *Streptococcus pneumoniae*, followed in frequency by encapsulated *Hemophilus influenzae*. Other bacteria such as enteric gram negatives, anaerobes, and *Staphylococcus aureus* are significant causes of pneumonia in specific settings, such as healthcare facilities. *Mycobacterium tuberculosis* is highly infectious, and historically was an important cause of mortality worldwide. It has mostly been controlled with antibiotics in the developed world, though multidrug-resistant strains continue to cause problems and are classified as Category C bioweapon agents. *Legionella pneumophila* was first identified during an outbreak in Philadelphia in 1978, though it is now recognized to occur widely at a low endemic rate related to environmental sources. Also, fungal infections of the lungs can cause symptomatic disease in normal hosts. *Histoplasma capsulatum, Coccidiodes immitis, Blastomyces dermatitidis*, and *Crytococcus neoformans* can all cause pneumonia related to local exposure to high environmental concentrations. Pneumonia due to these pathogenic fungi is usually self-limited in normal hosts. Some additional "atypical" microorganisms, such as mycoplasmas, account for a substantial fraction of additional pneumonias in normal hosts. It is contemplated that a composition of the present invention can provide a rapid, temporal protection against a spectrum of agents that can cause, for example pneumonia or other disease states. In certain aspects the present invention may be used in combination with a vaccination regime to provide an additional protection to a subject that may or is exposed to one or more pathogenic or potentially pathogenic organism.

In particular aspects of the invention the compositions and methods of the invention may be used to prevent, reduce the risk of or treat infection or exposure to a biological weapon/opportunistic microbe or exposure of a subject(s) to an inhaled infective agent. The only microbial pathogen that has been used as a terrorist weapon in the modern era is *Bacillus anthracis*, which has a case-fatality rate of 75% when infection occurs by the respiratory route, even with the use of appropriate antibiotics. *Francisella tularensis* is an aerobic, gram negative coccobacillus that is a facultative intracellular pathogen. It is highly infectious, highly pathogenic, and survives under harsh environmental conditions, making it a serious bioterror threat even though it is poorly transmissible from person to person (Dennis, 2001). A vaccine is available, but is only partially protective. The World Health Orgainization estimated that aerosol dispersal of 50 kg of virulent *Francisella tularensis* over a metropolitan area with 5 million inhabitants would result in 250,000 incapacitating casualties, including 19,000 deaths; the Centers for Disease Control (CDC) estimated the economic cost of such an attack to be $5.4 billion for every 100,000 persons exposed (Dennis, 2001).

Other Class A bioterrorism agents that can be transmitted by aerosol are *Yersinia pestis*, smallpox virus, and hemorrhagic fever viruses. In addition, multiple Class B and C agents can be effectively delivered by the respiratory route. Together, these organisms comprise gram-positive, gram-negative, intracellular, and extracellular bacteria, as well as a variety of viral classes. Because of the potential difficulty in initially identifying a specific bioterrorism agent, the complexity of locally stockpiling adaptive immune vaccines and antibiotics directed at specific agents, and the remarkable virulence of organisms such as *Bacillus anthracis* despite appropriate treatment, stimulation of innate defense capabilities of the lungs that could either prevent or preempt or attenuate infection with a bioterror agent delivered by the respiratory route; such an effect could have great public health value.

A. Pathogenic or Potentially Pathogenic Microbes

There are numerous microbes that are considered pathogenic or potentially pathogenic under certain conditions (i.e., opportunistic pathogens/microbes). In certain aspects, the pathogenicity is determined relative to infection via the lungs. Bacterial microbes include, but are not limited to various species of the *Bacillus, Yersinia, Franscisella, Streptococcus, Staphylococcus, Pseudomonas, Mycobacterium, Burkholderia* genus of bacteria. Particular species of bacteria from which a subject may be protected include, but is not limited to *Bacillus anthracis, Yersinia pestis, Francisella tularensis, Streptococcus pnemoniae, Staphylococcus aureas, Pseudomonas aeruginosa, Burkholderia cepacia, Corynebacterium diphtheriae, Clostridia* spp, *Shigella* spp., *Mycobacterium avium, M. intracellulare, M. kansasii, M paratuberculosis, M scrofulaceum, M. simiae, M. habana, M. interjectum, M xenopi, M. heckeshornense, M. szulgai, M. fortuitum, M. immunogenum, M. chelonae, M. marinum, M. genavense, M haemophilum, M. celatum, M. conspicuum, M malmoense, M. ulcerans, M. smegmatis, M wolinskyi, M. goodii, M. thermoresistible, M neoaurum, M. vaccae, M. palustre, M elephantis, M. bohemicam* and *M. septicum.*

B. Viruses

There are numerous viruses and viral strains that are considered pathogenic or potentially pathogenic under certain conditions. Viruses can be placed in one of the seven following groups: Group I: double-stranded DNA viruses, Group II: single-stranded DNA viruses, Group III: double-stranded RNA viruses, Group IV: positive-sense single-stranded RNA viruses, Group V: negative-sense single-stranded RNA viruses, Group VI: reverse transcribing Diploid single-stranded RNA viruses, Group VII: reverse transcribing Circular double-stranded DNA viruses. Viruses include the family Adenoviridae, Arenaviridae, Caliciviridae, Coronaviridae, Filoviridae, Flaviviridae, Hepadnaviridae, Herpesviridae (Alphaherpesvirinae, Betaherpesvirinae, Gammaherpesvirinae), Nidovirales, Papillomaviridae, Paramyxoviridae (Paramyxovirinae, Pneumovirinae), Parvoviridae (Parvovirinae, Picornaviridae), Poxviridae (Chordopoxvirinae), Reoviridae, Retroviridae (Orthoretrovirinae), and/or Togaviridae. These virus include, but are not limited to various strains of influenza, such as avian flu (e.g., H5N1). Particular virus from which a subject may be protected include, but is not limited to Cytomegalovirus, Respiratory syncytial virus and the like.

Examples of pathogenic virus include, but are not limited to Influenza A, H5N1, Marburg, Ebola, Dengue, Severe acute respiratory syndrome coronavirus, Yellow fever virus, Human respiratory syncytial virus, Vaccinia virus and the like.

C. Fungi

There are numerous fungal species that are considered pathogenic or potentially pathogenic under certain conditions. Protection can be provided for, but not limited to *Aspergillus fumigatus, Candida albicans, Cryptococcus neoformans, Histoplasma capsulatum, Coccidioides immitis,* or *Pneumocystis carinii,* and/or *Blastomyces dermatitidis.*

V. FORMULATIONS AND ADMINISTRATION

The pharmaceutical compositions disclosed herein may be administered via the respiratory system of a subject. In certain aspects the compositions are deposited in the lung by methods and devices known in the art. StIR compositions may be prepared in water suitably mixed with a surfactant, such as hydroxypropylcellulose. Dispersions may also be prepared in glycerol, liquid polyethylene glycols and mixtures thereof, and in oils. Under ordinary conditions of storage and use, these preparations contain a preservative to prevent the growth of microorganisms. The pharmaceutical forms suitable for inhalation include sterile aqueous solutions or dispersions and sterile powders for the extemporaneous preparation of sterile inhalable solutions or dispersions. In all cases the form is typically sterile and capable of inhalation directly or through some intermediary process or device. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. The prevention of the action of microorganisms can be brought about by various antibacterial and antifungal agents, for example, parabens, chlorobutanol, phenol, sorbic acid, thimerosal, and the like.

Some variation in dosage will necessarily occur depending on the condition of the subject being treated and the particular circumstances involving exposure or potential exposure. The person responsible for administration will, in any event, determine the appropriate dose for the individual subject. Moreover, for human administration, preparations should meet sterility, pyrogenicity, general safety, and purity standards as required by FDA Office of Biologics standards or other similar organizations.

Sterile compositions are prepared by incorporating the active components in the required amount in the appropriate solvent with various other ingredients enumerated above, as required, followed by, for example, filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile compositions, some methods of preparation are vacuum-drying and freeze-drying techniques which yield a powder of the active ingredient plus any additional desired ingredient from a previously sterile-filtered solution.

Pulmonary/respiratory drug delivery can be implemented by different approaches, including liquid nebulizers, aerosol-based metered dose inhalers (MDI's), sprayers, dry powder dispersion devices and the like. Such methods and compositions are well known to those of skill in the art, as indicated by U.S. Pat. Nos. 6,797,258, 6,794,357, 6,737,045, and 6,488,953, all of which are incorporated by reference. According to the invention, at least one pharmaceutical composition can be delivered by any of a variety of inhalation or nasal devices known in the art for administration of a therapeutic agent by inhalation. Other devices suitable for directing pulmonary or nasal administration are also known in the art. Typically, for pulmonary administration, at least one pharmaceutical composition is delivered in a particle size effective for reaching the lower airways of the lung or sinuses. Some specific examples of commercially available inhalation devices suitable for the practice of this invention are Turbohaler™ (Astra), Rotahaler® (Glaxo), Diskus® (Glaxo), Spiros™ inhaler (Dura), devices marketed by Inhale Therapeutics, AERx™ (Aradigm), the Ultravent® nebulizer (Mallinckrodt), the Acorn II® nebulizer (Marquest Medical Products), the Ventolin® metered dose inhaler (Glaxo), the Spinhaler® powder inhaler (Fisons), or the like.

All such inhalation devices can be used for the administration of a pharmaceutical composition in an aerosol. Such aerosols may comprise either solutions (both aqueous and non aqueous) or solid particles. Metered dose inhalers typically use a propellant gas and require actuation during inspiration. See, e.g., WO 98/35888; WO 94/16970. Dry powder inhalers use breath-actuation of a mixed powder. See U.S. Pat. Nos. 5,458,135; 4,668,218; PCT publications WO 97/25086; WO 94/08552; WO 94/06498; and European application EP 0237507, each of which is incorporated herein by reference in their entirety. Nebulizers produce aerosols from solutions, while metered dose inhalers, dry powder inhalers, and the like generate small particle aerosols. Suitable formulations for administration include, but are not limited to nasal spray or nasal drops, and may include aqueous or oily solutions of a StIR composition.

A spray comprising a pharmaceutical composition of the present invention can be produced by forcing a suspension or solution of a composition through a nozzle under pressure. The nozzle size and configuration, the applied pressure, and the liquid feed rate can be chosen to achieve the desired output and particle size. An electrospray can be produced, for example, by an electric field in connection with a capillary or nozzle feed.

A pharmaceutical composition of the present invention can be administered by a nebulizer such as a jet nebulizer or an ultrasonic nebulizer. Typically, in a jet nebulizer, a compressed air source is used to create a high-velocity air jet through an orifice. As the gas expands beyond the nozzle, a low-pressure region is created, which draws a composition through a capillary tube connected to a liquid reservoir. The liquid stream from the capillary tube is sheared into unstable filaments and droplets as it exits the tube, creating the aerosol. A range of configurations, flow rates, and baffle types can be employed to achieve the desired performance characteristics from a given jet nebulizer. In an ultrasonic nebulizer, high-frequency electrical energy is used to create vibrational, mechanical energy, typically employing a piezoelectric transducer. This energy is transmitted to the composition creating an aerosol.

In a metered dose inhaler (MDI), a propellant, a composition, and any excipients or other additives are contained in a canister as a mixture with a compressed gas. Actuation of the metering valve releases the mixture as an aerosol.

Pharmaceutical compositions for use with a metered-dose inhaler device will generally include a finely divided powder containing a composition of the invention as a suspension in a non-aqueous medium, for example, suspended in a propellant with the aid of a surfactant. The propellant can be any conventional material employed for this purpose such as chlorofluorocarbon, a hydrochlorofluorocarbon, a hydrofluorocarbon, or a hydrocarbon including trichlorofluoromethane, dichlorodifluoromethane, dichlorotetrafluoroethanol and 1,1,1,2-tetrafluoroethane, HFA-134a (hydrofluroalkane-134a), HFA-227 (hydrofluroalkane-227), or the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically acceptable" refers to molecular entities and compositions that do not produce an allergic or similar untoward reaction when administered to a subject. The preparation of an aqueous composition that contains a polypeptide or peptide as an active ingredient is well understood in the art.

VI. COMBINATION TREATMENTS

The compositions and methods of the present invention may be used in the context of a number of therapeutic or prophylactic applications. In order to increase the effectiveness of a treatment with the compositions of the present invention or to augment the protection of another therapy (second therapy), e.g., vaccination or antimicrobial therapy, it may be desirable to combine these compositions and methods with other agents and methods effective in the treatment, reduction of risk of infection, or prevention of diseases and pathologic conditions, for example, anti-bacterial, anti-viral, and/or anti-fungal treatments.

Various combinations may be employed; for example, a StIR composition is "A" and the secondary therapy is "B":

| | | | | | |
|---|---|---|---|---|---|
| A/B/A | B/A/B | B/B/A | A/A/B | A/B/B | B/A/A |
| A/B/B/B | B/A/B/B | B/B/B/A | B/B/A/B | A/A/B/B | A/B/A/B |
| A/B/B/A | B/B/A/A | B/A/B/A | B/A/A/B | A/A/A/B | B/A/A/A |
| A/B/A/A | A/A/B/A | | | | |

Administration of a composition of the present invention to a subject will follow general protocols for the administration via the respiratory system, and the general protocols for the administration of a particular secondary therapy will also be followed, taking into account the toxicity, if any, of the treatment. It is expected that the treatment cycles would be repeated as necessary. It also is contemplated that various standard therapies, as well as vaccination, may be applied in combination with the described therapies.

A. Anti-Virals

In certain aspects of the invention an anti-viral agent may be used in combination with a StIR composition. Antiviral drugs are a class of medication used specifically for treating viral infections and they should be distinguished from viricides, which actively deactivate virus particles outside the body. Most of the antivirals now available are designed to help deal with HIV, herpes viruses, the hepatitis B and C viruses, and influenza A and B viruses. Anti-viral agents useful in the invention include, but are not limited to, immunoglobulins, amantadine, interferons, nucleotide analogues, and protease inhibitors.

One anti-viral strategy is to interfere with the ability of a virus to infiltrate a target cell. This stage of viral replication can be inhibited by using agents which mimic the virus-associated protein (VAP) and bind to the cellular receptors. Or by using agents which mimic the cellular receptor and bind to the VAP. This includes anti-VAP antibodies, receptor anti-idiotypic antibodies, extraneous receptor and synthetic receptor mimics. Two such "entry-blockers," amantadine and rimantadine, have been introduced to combat influenza.

A second approach to anti-viral therapy is to target the processes that synthesize virus components after a virus invades a cell. One way of doing this is to develop nucleotide or nucleoside analogues that look like the building blocks of RNA or DNA, but deactivate the enzymes that synthesize the RNA or DNA once the analog is incorporated. Nucleotide analogs include, but are not limited to ribivirin, vidarabine, acyclovir, gangcyclovir, zidovudine, didanosine, zalcitabine, stavudine, and lamivudine.

Yet another antiviral technique is a set of drugs based on ribozymes, which are enzymes that will cut apart viral RNA or DNA at selected sites. In their natural course, ribozymes are used as part of the viral manufacturing sequence, but these synthetic ribozymes are designed to cut RNA and DNA at sites that will disable them.

Some viruses include an enzyme known as a protease that cuts viral protein chains apart so they can be assembled into their final configuration. HIV includes a protease, and so considerable research has been performed to find "protease inhibitors" to attack HIV at that phase of its life cycle. Protease inhibitors became available in the 1990s and have proven effective, though they can have unusual side effects, for example causing fat to build up in unusual places. Improved protease inhibitors are now in development.

The final stage in the life cycle of a virus is the release of completed viruses from the host cell, and this step has also been targeted by antiviral drug developers. Two drugs named zanamivir (RELENZA™) and oseltamivir (TAMIFLU™) that have been introduced to treat influenza prevent the release of viral particles by blocking a molecule named neuraminidase that is found on the surface of flu viruses, and also seems to be constant across a wide range of flu strains.

Anti-viral agents include, but are not limited to abacavir; acemannan; acyclovir; acyclovir sodium; adefovir; alovudine; alvircept sudotox; amantadine hydrochloride; amprenavir; aranotin; arildone; atevirdine mesylate; avridine; cidofovir; cipamfylline; cytarabine hydrochloride; delavirdine mesylate; desciclovir; didanosine; disoxaril; edoxudine; efavirenz; enviradene; enviroxime; famciclovir; famotine hydrochloride; fiacitabine; fialuridine; fosarilate; trisodium phosphonoformate; fosfonet sodium; ganciclovir; ganciclovir sodium; idoxuridine; indinavir; kethoxal; lamivudine; lobucavir; memotine hydrochloride; methisazone; nelfinavir; nevirapine; penciclovir; pirodavir; ribavirin; rimantadine hydrochloride; ritonavir; saquinavir mesylate; somantadine hydrochloride; sorivudine; statolon; stavudine; tilorone hydrochloride; trifluridine; valacyclovir hydrochloride; vidarabine; vidarabine phosphate; vidarabine sodium phosphate; viroxime; zalcitabine; zidovudine; zinviroxime, interferon, cyclovir, alpha-interferon, and/or beta globulin.

In certain embodiments an anti-viral is ribivirin and high dose ribivirin. Ribavirin is an anti-viral drug that is active against a number of DNA and RNA viruses. It is a member of the nucleoside antimetabolite drugs that interfere with duplication of viral genetic material. Though not effective against all viruses, ribavirin has wide range of activity, including important activities against influenzas, flaviviruses, and agents of many viral hemorrhagic fevers.

Typically, the oral form of ribavirin is used in the treatment of hepatitis C, in combination with pegylated interferon drugs. The aerosol form has been used in the past to treat respiratory syncytial virus-related diseases in children. However, its efficacy has been called into question by multiple studies, and most institutions no longer use it.

B. Anti-Bacterials

Examples of anti-bacterials include, but are not limited to, β-lactam antibiotics, penicillins (such as natural penicillins, aminopenicillins, penicillinase-resistant penicillins, carboxy penicillins, ureido penicillins), cephalosporins (first generation, second generation, and third generation cephalosporins), and other β-lactams (such as imipenem, monobactams), β-lactamase inhibitors, vancomycin, aminoglycosides and spectinomycin, tetracyclines, chloramphenicol, erythromycin, lincomycin, clindamycin, rifampin, metronidazole, polymyxins, sulfonamides and trimethoprim, and quinolines. Anti-bacterials also include, but are not limited to: Acedapsone, Acetosulfone Sodium, Alamecin, Alexidine, Amdinocillin, Amdinocillin Pivoxil, Amicycline, Amifloxacin, Amifloxacin Mesylate, Amikacin, Amikacin Sulfate, Aminosalicylic acid, Aminosalicylate sodium, Amoxicillin, Amphomycin, Ampicillin, Ampicillin Sodium, Apalcillin Sodium, Apramycin, Aspartocin, Astromicin Sulfate, Avilamycin, Avoparcin, Azithromycin, Azlocillin, Azlocillin Sodium, Bacampicillin Hydrochloride, Bacitracin, Bacitracin Methylene Disalicylate, Bacitracin Zinc, Bambermycins, Benzoylpas Calcium, Berythromycin, Betamicin Sulfate, Biapenem, Biniramycin, Biphenamine Hydrochloride, Bispyrithione Magsulfex, Butikacin, Butirosin Sulfate, Capreomycin Sulfate, Carbadox, Carbenicillin Disodium, Carbenicillin Indanyl Sodium, Carbenicillin Phenyl Sodium, Carbenicillin Potassium, Carumonam Sodium, Cefaclor, Cefadroxil, Cefamandole, Cefamandole Nafate, Cefamandole Sodium, Cefaparole, Cefatrizine, Cefazaflur Sodium, Cefazolin, Cefazolin Sodium, Cefbuperazone, Cefdinir, Cefepime, Cefepime Hydrochloride, Cefetecol, Cefixime, Cefmenoxime Hydrochloride, Cefmetazole, Cefmetazole Sodium, Cefonicid Monosodium, Cefonicid Sodium, Cefoperazone Sodium, Ceforanide, Cefotaxime Sodium, Cefotetan, Cefotetan Disodium, Cefotiam Hydrochloride, Cefoxitin, Cefoxitin Sodium, Cefpimizole, Cefpimizole Sodium, Cefpiramide, Cefpiramide Sodium, Cefpirome Sulfate, Cefpodoxime Proxetil, Cefprozil, Cefroxadine, Cefsulodin Sodium, Ceftazidime, Ceftibuten, Ceftizoxime Sodium, Ceftriaxone Sodium, Cefuroxime, Cefuroxime Axetil, Cefuroxime Pivoxetil, Cefuroxime Sodium, Cephacetrile Sodium, Cephalexin, Cephalexii Hydrochloride, Cephaloglycini, Cephaloridine, Cephalothin Sodium, Cephapirin Sodium, Cephradine, Cetocycline Hydrochloride, Cetophenicol, Chloramphenicol, Cliloramphenicol Palmitate, Chloramphenicol Pantotheniate Complex, Chloramphenicol Sodium Succinate, Chlorhexidine Phosphanilate, Chloroxylenol, Chlortetracycline Bisulfate, Chlortetracycline Hydrochloride, Cinoxacin, Ciprofloxacin, Ciprofloxacin Hydrochloride, Cirolemycin, Clarithromycin, Clinafloxacin Hydrochloride, Clildamycin, Clindamycin Hydrochloride, Clindamycin Palmitate Hydrochloride, Clindamycin Phosphate, Clofazimine, Cloxacillin Benzathine, Cloxacillin Sodium, Cloxyquin, Colistimethate Sodium, Colistin Sulfate, Coumermycin, Coumermycin Sodium, Cyclacillin, Cycloserine, Dalfopristin, Dapsone, Daptomycin, Demeclocycine, Demeclocycine Hydrochloride, Demecycline, Denofungin, Diaveridine, Dicloxacillin, Dicloxacillin Sodium, Dihydrostreptomycin Sulfate, Dipyrithione, Dirithromycin, Doxycycline, Doxycycline Calcium, Doxycycline Fosfatex, Doxycycline Hyclate, Droxacin Sodium, Enoxacin, Epicillin, Epitetracycline Hydrochloride, Erythromycin, Erythromycin Acistrate, Erythromycin Estolate, Erythromycin Ethylsuccinate, Erythromycin Glucepate, Erythromycin Lactobionate, Erythromycin Propionate, Erythromycin Stearate, Ethambutol Hydrochloride, Ethionamide, Fleroxacin, Floxacillin, Fludalanine, Flumequine, Fosfomycin, Fosfomycin Tromethamine, Fumoxicillin, Furazolium Chloride, Furazolium Tartrate, Fusidate Sodium, Fusidic Acid, Gentamicin Sulfate, Gloximonam, Gramicidin, Haloprogin, Hetacillin, Hetacillin Potassium, Hexedine, Ibafloxacin, Imipenem, Isoconazole, Isepamicin, Isoniazid, Josamycin, Kanamycin Sulfate, Kitasamycin, Levofuraltadone, Levopropylcillin Potassium, Lexithromycin, Lincomycin, Lincomycin Hydrochloride, Lomefloxacin, Lomefloxacin Hydrochloride, Lomefloxacin Mesylate, Loracarbef, Mafenide, Meclocycline, Meclocycline Sulfosalicylate, Megalomicin Potassium Phosphate, Mequidox, Meropenem, Methacycline, Methacycline Hydrochloride, Methenamine, Methenamine Hippurate, Methenamine Mandelate, Methicillin Sodium, Metioprim, Metronidazole Hydrochloride, Metronidazole Phosphate, Mezlocillin, Mezlocillin Sodium, Minocycline, Minocycline Hydrochloride, Mirincamycin Hydrochloride, Monensin, Monensin Sodium, Nafcillin Sodium, Nalidixate Sodium, Nalidixic Acid, Natamycin, Nebramycin, Neomycin Palmitate, Neomycin Sulfate, Neomycin Undecylenate, Netilmicin Sulfate, Neutramycin, Nifuradene, Nifuraldezone, Nifuratel, Nifuratrone, Nifurdazil, Nifurimide, Nifuirpirinol, Nifurquinazol, Nifurthiazole, Nitrocycline, Nitrofurantoin, Nitromide, Norfloxacin, Novobiocin Sodium, Ofloxacin, Ormetoprim, Oxacillin Sodium, Oximonam, Oximonam Sodium, Oxolinic Acid, Oxytetracycline, Oxytetracycline Calcium, Oxytetracycline Hydrochloride, Paldimycin, Parachlorophenol, Paulomycin, Pefloxacin, Pefloxacin Mesylate, Penamecillin, Penicillin G Benzathine, Penicillin G Potassium, Penicillin G Procaine, Penicillin G Sodium, Penicillin V, Penicillin V Benzathine, Penicillin V Hydrabamine, Penicillin V Potassium, Pentizidone Sodium, Phenyl Aminosalicylate, Piperacillin Sodium, Pirbenicillin Sodium, Piridicillin Sodium, Pirlimycin Hydrochloride, Pivampicillin Hydrochloride, Pivampicillin Pamoate, Pivampicillin Probenate, Polymyxin B Sulfate, Porfiromycin, Propikacin, Pyrazinamide, Pyrithione Zinc, Quindecamine Acetate, Quinupristin, Racephenicol, Ramoplanin, Ranimycin, Relomycin, Repromicin, Rifabutin, Rifametane, Rifamexil, Rifamide, Rifampin, Rifapentine, Rifaximin, Rolitetracycline, Rolitetracycline Nitrate, Rosaramicin, Rosaramicin Butyrate, Rosaramicin Propionate, Rosaramicin Sodium Phosphate, Rosaramicin Stearate, Rosoxacin, Roxarsone, Roxithromycin, Sancycline, Sanfetrinem Sodium, Sarmoxicillin, Sarpicillin, Scopafungin, Sisomicin, Sisomicin Sulfate, Sparfloxacin, Spectinomycin Hydrochloride, Spiramycin, Stallimycin Hydrochloride, Steffimycin, Streptomycin Sulfate, Streptonicozid, Sulfabenz, Sulfabenzamide, Sulfacetamide, Sulfacetamide Sodium, Sulfacytine, Sulfadiazine, Sulfadiazine Sodium, Sulfadoxine, Sulfalene, Sulfamerazine, Sulfameter, Sulfamethazine, Sulfamethizole, Sulfamethoxazole, Sulfamonomethoxine, Sulfamoxole, Sulfanilate Zinc, Sulfanitran, Sulfasalazine, Sulfasomizole, Sulfathiazole, Sulfazamet, Sulfisoxazole, Sulfisoxazole Acetyl, Sulfisoxazole Diolamine, Sulfomyxin, Sulopenem, Sultamicillin, Suncillin Sodium, Talampicillin Hydrochloride, Teicoplanin, Temafloxacin Hydrochloride, Temocillin, Tetracycline, Tetracycline Hydrochloride, Tetracycline Phosphate Complex, Tetroxoprim, Thiamphenicol, Thiphencillin Potassium, Ticarcillin Cresyl Sodium, Ticarcillin Disodium, Ticarcillin Monosodium, Ticlatone, Tiodonium Chloride, Tobramycin, Tobramycin Sulfate, Tosufloxacin, Trimethoprim, Trimethoprim Sulfate, Trisulfapyrimidines, Troleandomycin, Trospectomycin Sulfate, Tyrothricin, Vancomycin, Vancomycin Hydrochloride, Virginiamycin, and/or Zorbamycin.

B. Anti-Fungals

Anti-fungal agents include, but are not limited to, azoles, imidazoles, polyenes, posaconazole, fluconazole, itraconazole, amphotericin B, 5-fluorocytosine, miconazole, ketoconazole, Myambutol (Ethambutol Hydrochloride), Dapsone (4,4'-diaminodiphenylsulfone), Paser Granules (aminosalicylic acid granules), rifapentine, Pyrazinamide, Isoniazid, Rifadin IV, Rifampin, Pyrazinamide, Streptomycin Sulfate and Trecator-SC (Ethionamide) and/or voriconazole (Vfend™)

C. Other Agents

In certain aspects of the invention an anti-inflammatory agent may be used in combination with a StIR composition.

Steroidal anti-inflammatories for use herein include, but are not limited to fluticasone, beclomethasone, any pharmaceutically acceptable derivative thereof, and any combination thereof. As used herein, a pharmaceutically acceptable derivative includes any salt, ester, enol ether, enol ester, acid, base, solvate or hydrate thereof. Such derivatives may be prepared by those of skill in the art using known methods for such derivatization.

Fluticasone—

Fluticasone propionate is a synthetic corticosteroid and has the empirical formula $C_{25}H_{31}F_3O_5S$. It has the chemical name S-(fluromethyl)6α,9-difluoro-11β-17-dihydroxy-16α-methyl-3-oxoandrosta-1,4-diene-17β-carbothioate,17-propionate. Fluticasone propionate is a white to off-white powder with a molecular weight of 500.6 and is practically insoluble in water, freely soluble in dimethyl sulfoxide and dimethylformamide, and slightly soluble in methanol and 95% ethanol.

In an embodiment, the formulations of the present invention may comprise a steroidal anti-inflammatory (e.g., fluticasone propionate)

Beclomethasone—

In certain aspects the steroidal anti-inflammatory can be beclomethasone dipropionate or its monohydrate. Beclomethasone dipropionate has the chemical name 9-chloro-11b,17,21-trihydroxy-16b-methylpregna-1,4-diene-3,20-doine17,21-dipropionate. The compound may be a white powder with a molecular weight of 521.25; and is very slightly soluble in water (Physicians' Desk Reference), very soluble in chloroform, and freely soluble in acetone and in alcohol.

Providing steroidal anti-inflammatories according to the present invention may enhance the compositions and methods of the invention by, for example, attenuating any unwanted inflammation. Examples of other steroidal anti-inflammatories for use herein include, but are not limited to, betamethasone, triamcinolone, dexamethasone, prednisone, mometasone, flunisolide and budesonide.

In accordance with yet another aspect of the invention, the non-steroidal anti-inflammatory agent may include aspirin, sodium salicylate, acetaminophen, phenacetin, ibuprofen, ketoprofen, indomethacin, flurbiprofen, diclofenac, naproxen, piroxicam, tebufelone, etodolac, nabumetone, tenidap, alcofenac, antipyrine, amimopyrine, dipyrone, anisopyrone, phenylbutazone, clofezone, oxyphenbutazone, prexazone, apazone, benzydamine, bucolome, cinchopen, clonixin, ditrazol, epirizole, fenoprofen, floctafeninl, flufenamic acid, glaphenine, indoprofen, meclofenamic acid, mefenamic acid, niflumic acid, salidifamides, sulindac, suprofen, tolmetin, nabumetone, tiaramide, proquazone, bufexamac, flumizole, tinoridine, timegadine, dapsone, diflunisal, benorylate, fosfosal, fenclofenac, etodolac, fentiazac, tilomisole, carprofen, fenbufen, oxaprozin, tiaprofenic acid, pirprofen, feprazone, piroxicam, sudoxicam, isoxicam, celecoxib, Vioxx®, and/or tenoxicam.

VII. KITS

Any of the compositions described herein may be comprised in a kit. In a non-limiting example, reagents for production and/or delivery of a StIR composition are included in a kit. In certain aspects the kit is portable and may be carried on a person much like an asthma inhaler is carried. The kit may further include a pathogen detector. The kit may also contain a gas or mechanical propellant for compositions of the invention.

The components of the kits may be packaged either in an aqueous, powdered, or lyophilized form. The container means of the kits will generally include at least one inhaler, canister, vial, test tube, flask, bottle, syringe or other container means, into which a component may be placed, and preferably, suitably aliquoted. Where there is more than one component in the kit (second agent, etc.), the kit also will generally contain a second, third or other additional container into which the additional components may be separately placed. However, various combinations of components may be comprised in a vial, canister, or inhaler. A container of the invention can include a canister or inhaler that can be worn on a belt or easily carried in a pocket, backpack or other storage container. The kits of the present invention also will typically include a container for the described compositions or their variations, and any other reagent containers in close confinement for commercial sale. Such containers may include injection or blow molded plastic containers into which the desired vials are retained.

When the components of the kit are provided in one and/or more liquid solutions, e.g., the liquid solution is an aqueous solution, with a sterile aqueous solution being particularly preferred, but not required. However, the components of the kit may be provided as dried powder(s). When reagents and/or components are provided as a dry powder, the powder may be reconstituted by the addition of a suitable solvent or administered in a powdered form. It is envisioned that a solvent may also be provided in another container means.

A kit will also include instructions for employing the kit components as well the use of any other reagent not included in the kit. Instructions may include variations that can be implemented.

It is contemplated that such reagents are embodiments of kits of the invention. Such kits, however, are not limited to the particular items identified above and may include any reagent used directly or indirectly in the detection of pathogenic microorganisms or administration of a StIR composition of the invention.

VIII. EXAMPLES

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. The present examples, along with the methods described herein are presently representative of certain embodiments and are not intended as limitations on the scope of the invention. Changes therein and other uses which are encompassed within the spirit of the invention as defined by the scope of the claims will occur to those skilled in the art.

Example 1

P. aeruginosa Challenge

Strain PA103 was obtained from the ATCC and stored as frozen stock ($1 \times 10^8$ CFU/ml) in 20% glycerol in LB-Medium (Bio 101 Systems). One ml of stock was incubated for 16 h in 100 ml LB-Medium at 37° C. in 5% $CO_2$, then diluted in 1 L of fresh broth and grown at 37° C. for 6-7 hr to $OD_{600}$ of 0.3, yielding ~$3 \times 10^{10}$ CFU. The suspension was centrifuged, washed, resuspended and aerosolized challenge, and bacterial concentrations were determined by plating serial dilutions onto tryptic soy agar plates (Becton Dickinson). For aerosolization, 10 ml of the suspension was placed in an AeroMist CA-209 nebulizer (CIS-US) driven by 10 L/min of 5% $CO_2$ in air to promote deep ventilation. After 30 min, another 5 ml was added, with a total of 10 ml of suspension aerosolized during the full 60 min.

TLR Ligand Treatment.

Prior to infectious challenges, mice were treated with aerosols of TLR ligands, alone or in combination, or with PBS (negative control). All treatments were delivered 18 hours prior to the infectious challenge using an AeroMist CA-209 nebulizer driven by 10 L/min supplemented with 5% $CO_2$ to promote ventilation. For each treatment, 10 ml of the TLR ligand suspension or PBS was placed in the nebulizer and was administered over 20 min. For experiments using combinations of TLR ligands, both ligands were suspended in the same 10 ml suspension, and were delivered simultaneously. For each ligand, initial aerosol dosing was determined by the minimum suspension concentration at which neutrophilic infiltration of the lung was induced, as determined by total white blood cell and neutrophil counts in the bronchoalveolar lavage fluid at 24 h after treatment.

TLR 4 Ligands.

Unlike naturally occurring lipid A that contains a mixture of 5, 6, and 7 acyl groups, monophosphoryl lipid A-synthetic (MPLAs, Invivogen) is a pure synthetic containing 6 fatty acyl groups. Suspensions of MPLAs were delivered at 100 µg/ml. Another synthetic lipid A with 6 fatty acyl groups, Phosphorylated HexaAcyl Disaccharide (PHAD, Avanti Polar Lipids), was delivered at 100 µg/ml.

TLR 2/6 Ligands.

Pam2CSK4 and FSL-1 (both from Invivogen) are synthetic diacylayed lipopeptides known to signal though heterodimers of TLR2 and TLR6. Pam2CSK4 was delivered at 6 or 20 µg/ml, as indicated, and FSL-1 was delivered at 20 µg/ml.

TLR 9 Ligand.

ODN 2395 (Invivogen) is a Type C CpG oligonucleotide with high affinity for human and murine TLR9. ODN 2395 was aerosolized at 20 µg/ml.

TLR 7 Ligand.

Imiquimod (R837, Invivogen) is an imidazoquinoline amine guanosine analog that stimulates TLR7, and possibly TLR8. Imiquimod was delivered by aerosol at 1 or 300 µg/ml, as indicated.

TLR 5 Ligand.

A highly conserved 22 amino acid segment of flagellin, a known ligand of TLR5, was identified. This amino acid segment was submitted for synthesis at Cell Essentials, Inc., Boston, Mass. The peptide was confirmed to be >95% pure based on HPLC and Maldi-TOF mass spectrometry, and its solubility in PBS was confirmed. The synthetic fragment of Flg22 was delivered at 100 µg/ml.

Example 2

Materials and Methods

Animals and Reagents.

All general reagents were obtained from Sigma (St Louis, Mo.), except as indicated. All mice were handled in accordance with the policies of the Institutional Animal Care and Use Committee of the University of Texas M. D. Anderson Cancer Center. Wild type five to eight week-old female Swiss-Webster mice (Charles River, Wilmington, Mass.) were used for most protection and cell count experiments. As indicated, five to eight week-old female MyD88$^{-/-}$ mice provided by Shizuo Akira (1998), Trif$^{-/-}$ mice (The Jackson Laboratory, Bar Harbor, Me.) and TLR2$^{-/-}$ mice (Jackson) were used in comparison to wild type mice C57BL/6J (Jackson).

Aerosolized Treatments.

Frozen stock of non-typeable Haemophilus influenzae (NTHi) was grown on chocolate agar (Remel, Lenexa, Kans.), expanded in brain-heart infusion broth (Acumedia, Baltimore, Md.) supplemented with 3.5 µg/ml NAD, and disrupted with an EmulsiFlex C5 (Avestin, Mannheim, Germany), as described (Clement et al., 2008; Evans et al., 2010; Moghaddam et al., 2008). The protein concentration was adjusted to 2.5 mg/ml in saline by bicinchoninic assay (Pierce, Rockford, Ill.), and the lysate was frozen in 10 ml aliquots at −80° C. For treatment, a thawed aliquot was placed in an AeroMist CA-209 nebulizer (CIS-US) driven by 10 l/min air supplemented with 5% $CO_2$ (to promote deep breathing) for 20 min. The nebulizer was connected by polyethylene tubing (30 cm×22 mm) to a 10 liter polyethylene exposure chamber, with an identical efflux tube with a low resistance microbial filter (BB50T, Pall, East Hills, N.Y.) at its end vented to a biosafety hood.

Pam3CSK4, Pam2CSK4, Poly (I:C), MPLA, Imiquimod, and ODS 2395 were purchased from InvivoGen (San Diego, Calif.). A 22-mer Flg22, the most conserved domain of flagellin (QRLSTGSRINSAKDDAAGLQIA) (SEQ ID NO:2), was synthesized by Cell Essentials (Boston, Mass.). To treat the animals, synthetic TLR agonist were reconstituted in endotoxin-free water, suspended in 8 ml sterile PBS at indicated concentrations, and aerosolized to the animals for 20 min using the same technique as used for NTHi lysate treatment.

In Vivo Infectious Challenges.

As previously described (Clement et al., 2008; Clement et al., 2009; Evans et al., 2010), mice were inhalationally challenged with bacterial inocula targeted to $LD_{80}$-$LD_{100}$. *P. aeruginosa* strain PA103 was obtained from the ATCC and stored as frozen stock ($1 \times 10^8$ CFU/ml) in 20% glycerol in LB-Medium (Bio 101 Systems). One ml of stock was incubated for 16 h in 100 ml LB-Medium at 37° C. in 5% $CO_2$, then diluted in 1 l of fresh broth and grown at 37° C. for 6-7 h to $OD_{600}$ of 0.3, yielding $1$-$4 \times 10^{10}$ CFU/ml. *S. pneumoniae* serotype 4 was stored as frozen stock ($1 \times 10^9$ CFU) in 20% glycerol in Todd-Hewett broth (Becton Dickinson). One ml of thawed stock was incubated for 16 h in 150 ml Todd-Hewitt broth at 37° C. in 5% $CO_2$, then diluted in 1.5 l of fresh broth and grown in logarithmic phase for 6-7 h to an $OD_{600}$ of 0.3, yielding $2$-$6 \times 10^{11}$ CFU/ml. The bacterial suspensions were centrifuged, washed, resuspended in 10 ml PBS and aerosolized over a period of 60 min using a system identical to that used for the treatments. Bacterial concentrations were determined by plating serial dilutions onto tryptic soy agar plates (Becton Dickinson).

Quantification of Lung Pathogen Burden.

As previously described (Clement et al., 2008; Clement et al., 2009; Evans et al., 2010), immediately after infection with bacterial pathogens, mice were anesthetized and their lungs were harvested and homogenized in 1 ml of PBS utilizing a 2 ml tissue grinder (Kontes, Vineland, N.J.). Serial dilutions of the homogenates were plated on tryptic soy agar (TSA) plates, incubated at 37° C. for 16 h, and bacterial colonies were counted.

Bronchoalveolar Lavage Fluid Analysis.

As previously described (Clement et al., 2008; Clement et al., 2009; Evans et al., 2010), bronchoalveolar lavage (BAL) fluid was obtained by instilling and collecting two aliquots of 1 ml each of PBS through a luer stub adapter cannula (Becton Dickinson) inserted through rings of the exposed trachea at indicated time points. Total leukocyte count was determined with a hemacytometer (Hauser Scientific, Horsham, Pa.), and differential count by cytocentrifugation of 300 μl of BAL fluid at 2,000 rpm for 5 min, followed by Wright-Giemsa staining.

In Vitro Killing Assay.

As previously described (Clement et al., 2008; Clement et al., 2009; Evans et al., 2010), MLE-15 cells and A549 cells were cultured on 6-well plates in RPMI-1640 supplemented with 10% heat-inactivated FCS and 1% penicillin/streptomycin (Invitrogen). When grown to ~80% confluence, cells were washed with PBS, supplied with fresh antibiotic-free media with 10% heat-inactivated FCS, and treated with 20 μl PBS or a 20 μl volume of ODN 2395 (20 μg/ml), Pam2CSK4 (10 μg/ml), or both in RPMI-1640 containing 10% heat-inactivated FCS. After 4 h, 1000 spores of *Bacillus anthracis* Sterne strain or 2000 CFU *P. aeruginosa* strain PA103 were then added to all wells. Four h after infection, 20 μl of the supernatant from each well was aspirated, serially diluted, plated on a TSA agar plate, incubated for 16 h at 37° C., and CFUs were counted.

Immunofluorescence Microscopy.

A549 cells were cultured on Lab-Tek II chamber slides (Nunc, Rochester, N.Y.) in RPMI-1640 supplemented with 10% heat-inactivated FCS and 1% penicillin/streptomycin (Invitrogen) for 48 h, then treated with a 20 μl volume of Texas Red-labeled ODN 2395 (20 μg/ml, Invivogen), fluorescein isothiocyanate (FITC)-labeled Pam2CSK4 (10 μg/ml, Invivogen), or both in RPMI-1640 containing 10% heat-inactivated FCS. After 2 h, the media was suctioned, the chambers were detached, and the cells were washed three times with iced PBS. The cells were then fixed with 4% paraformaldehyde, quenched with glycine, washed three times with PBS, nuclear counterstained with 4',6-diamidino-2-phenylindole (DAPI; 0.1 μg/ml), and examined with fluorescence microscopy (Olympus BX-60 microscope, Melville, N.Y.) using appropriate optics (Texas Red: excitation=540 nm; emission=620 nm; FITC: excitation=495 nm, emission=520 nm; DAPI: excitation=360 nm; emission=460 nm). Images were collected sequentially with a computer-regulated Spot RT Camera (Diagnostic Instruments, Sterling Heights, Mich.) and assembled in Photoshop CS3 (Adobe, San Jose, Calif.). Overlapping red and green fluorescence appeared yellow.

Statistical Analysis.

Statistical analysis was performed using SAS/STAT software (version 8.2, SAS Institute). Student's t-test was used to compare the lung bacterial or viral titers between groups. Percentage of mice surviving pathogen challenges was compared using Fisher's exact test, and the log-rank test was used to compare the survival distribution estimated by the Kaplan-Meier method. One-way ANOVA with Dunnett's post hoc test was used to compare the BAL fluid differential counts between the treated and untreated animals.

Results

MyD88, but not TRIF, is Required for the Induction of Resistance to Pneumonia by an Aerosolized Bacterial Lysate.

Figure 12:
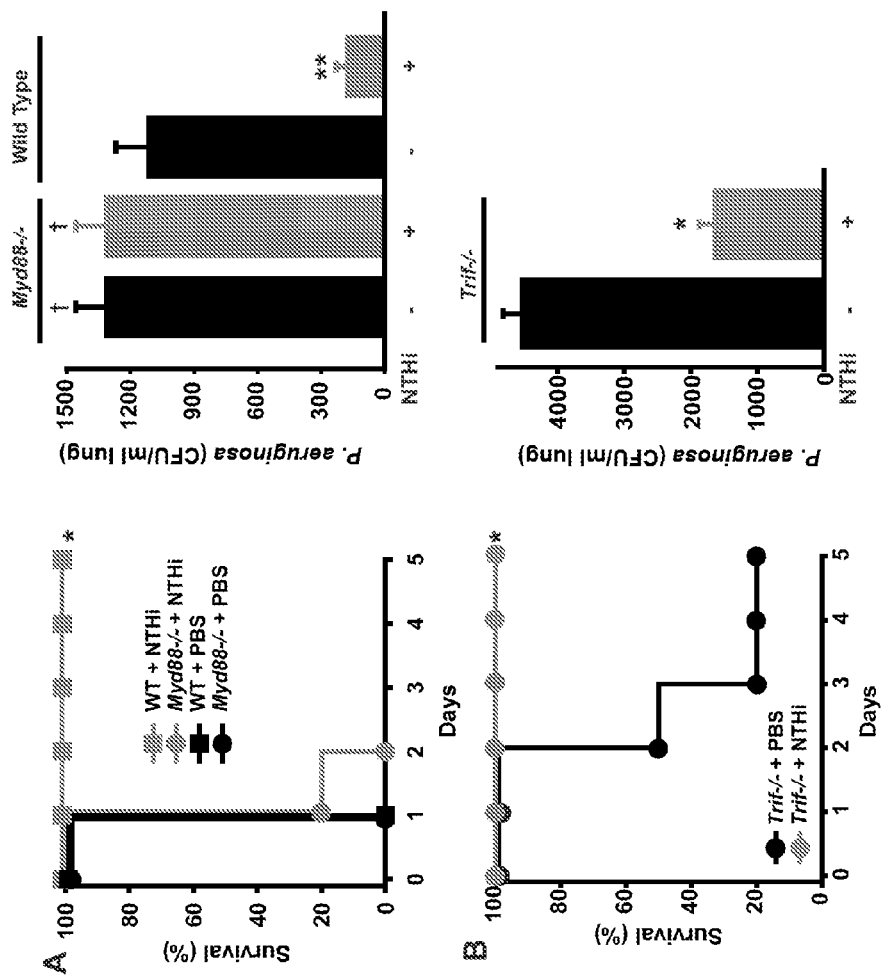
FIGS. 12A and 12B. MyD88, but not TRIF, signaling is required for bacterial lysate-induced resistance to pneumonia.
Figure 13:
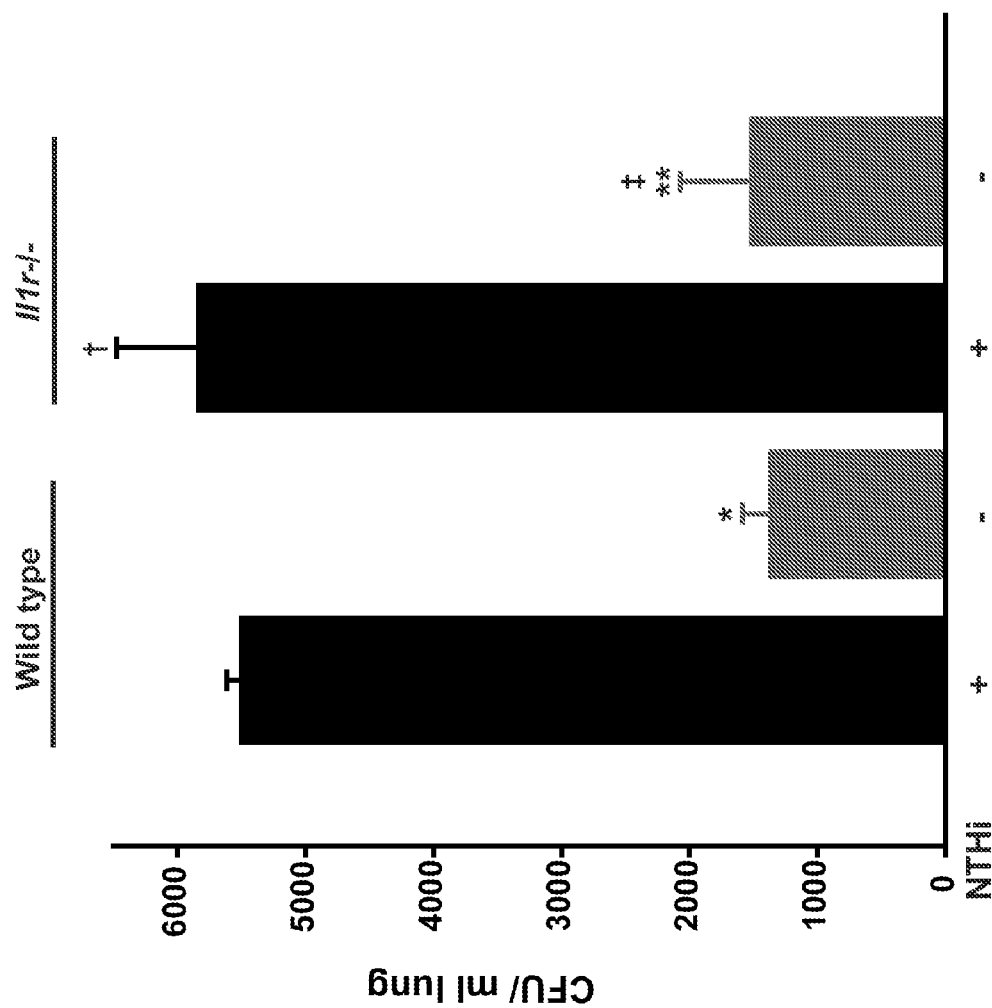
FIG. 13. Induced pathogen killing is not impaired in interleukin-1 receptor deficient mice. Il1r−/− and wild type mice were treated with aerosolized PBS or a lysate of non-typeable *Haemophilus influenzae* (NTHi) 24 h before challenge with *P. aeruginosa*. Shown is the bacterial burden of lung homogenates immediately after infection. (N=3 mice/group, *p=0.001 vs. wild type+PBS, **p=0.01 vs. Il1r−/−, †p=0.66 vs. wild type+PBS, ‡p=0.89 vs. wild type+NTHi)

Stimulation of lung epithelium by an aerosolized lysate of NTHi induces a high level of resistance to a broad array of microbial pathogens 9 (Clement et al., 2008; Clement et al., 2009; Evans et al., 2010; Tuvim et al., 2009). To test whether TLR signaling is required for lysate-induced protection, mice deficient in TLR signaling through TIR adaptors were inhalationally challenged with *P. aeruginosa*. Wild type and TRIF-deficient ($Trif^{-/-}$) mice were fully protected against lethal *P. aeruginosa* challenges by pretreatment with the aerosolized bacterial lysate, whereas resistance could not be induced in mice deficient in MyD88 ($Myd88^{-/-}$; FIGS. 12A and 12B, left panels). Protection closely correlated with the induction of rapid pathogen killing in the lungs (FIGS. 12A and 12B, right panels). The IL-1 receptor also signals through MyD88 (Adachi et al., 1998; Medzhitov et al., 1998), but responds to host cytokine signaling, rather than to microbial products directly. Pathogen killing was fully preserved in IL-1 receptor deficient mice ($Il1r^{-/-}$; FIG. 13) stimulated by the aerosolized bacterial lysate. This finding indicates that not all receptors signaling through MyD88 are required for lysate-induced protection, and suggests that direct microbial signaling through TLRs is more important than indirect signaling through host cytokines for inducible epithelial resistance.

Individual TLR Agonists Induce a Low Level of Resistance to Pneumonia.

In view of the requirement for MyD88 signaling, the inventors tested whether any individual synthetic TLR agonists could induce resistance similar to that afforded by the aerosolized bacterial lysate. As TLR1 and TLR6 are expressed as heterodimers with TLR2, and as TLR7 and TLR8 both recognize imiquimod, mouse TLRs 1 through 9 could all be stimulated with the following seven synthetic ligands: Pam3CSK4 (TLR2/1 agonist), Pam2CSK4 (TLR2/6 agonist), Poly(I:C) (TLR3 agonist), synthetic lipid A (MPLA, TLR4 agonist), Flg22 (synthetic 22-mer of flagellin, TLR5 agonist), imiquimod (TLR7 and TLR8), or ODN2395 (TLR9 agonist).

The appropriate aerosolized dose of these agonists was not known, so a strategy was formulated to identify an adequate dose for delivery to the lungs to avoid a type II ($\beta$) error. Each of the synthetic TLR agonists used has a reported concentration at which maximal cytokine secretion is stimulated from dendritic cells ([DCmax]) (Yamamoto et al., 2003; Aliprantis et al., 1999; Buwitt-Beckmann et al., 2005; Hayashi et al., 2001; Krug et al., 2001; Lee et al., 2003; Martin et al., 2003). Based on calculations of effective airway delivery of aerosolized compounds (Clement et al., 2009; Evans et al., 2004), the inventors determined the nebulizer fluid concentrations required to achieve [DCmax] at the airway epithelial surface. Although aerosolized lysate-induced resistance does not depend upon leukocyte influx, the protective phenomenon is tightly correlated with the timing and magnitude of induced lung neutrophilia (Clement et al., 2008). Therefore, to identify TLR agonist doses sufficient for testing, the inentors began at the reported [DCmax] for each ligand and increased the nebulized concentrations logarithmically until leukocyte infiltration was achieved.

As shown in FIG. 14, in PBS treated mice, the number of neutrophils in BAL fluid is $0.1 \times 10^3 \pm 0.2$ cells/ml. Only Pam2CSK4 demonstrated a significant increase in neutrophils at DCmax, though all but poly(I:C) and Flg22 showed significant increases in neutrophil levels at concentrations one to two logs above DCmax. On the other hand, both poly(I:C) and Flg22 induced significant influx of macrophages on BAL 24 h after treatment. Flg22 and imiquimod each had a ligand concentration above which there was a reduction in neutrophil infiltration. Pam2CSK4 induced a level of neutrophilia nearly 5-fold higher than Pam3CSK4 and 15-fold higher than any other ligand.

The concentration chosen for each ligand was the lowest dose to induce a 10-fold increase in neutrophils/ml or to induce doubling of the macrophages (none did both). While some of the ligands induced robust cellular infiltration, none of the synthetic agonists provided robust protection against lethal P. aeruginosa pneumonia (FIG. 15). There was a trend towards protection with Pam2CSK4, Flg22, and imiquimod though these did not reach statistical significance with individual experiments or in the mean of multiple experiments. MPLA treated mice showed a non-significant trend towards increased mortality after pathogen challenge.

A Combination of TLR2/6 and TLR9 Agonists Induces a High Level of Resistance Against Pneumonia.

Although single synthetic TLR agonists provided only moderate protection, it is possible that simultaneous stimulation of multiple PRRs is required to induce a high level of resistance (Clement et al., 2008; Evans et al., 2010). To determine whether combinations of TLR agonists could induce resistance, the inventors tested the pairwise permutations of the seven synthetic ligands.

Figure 16A:
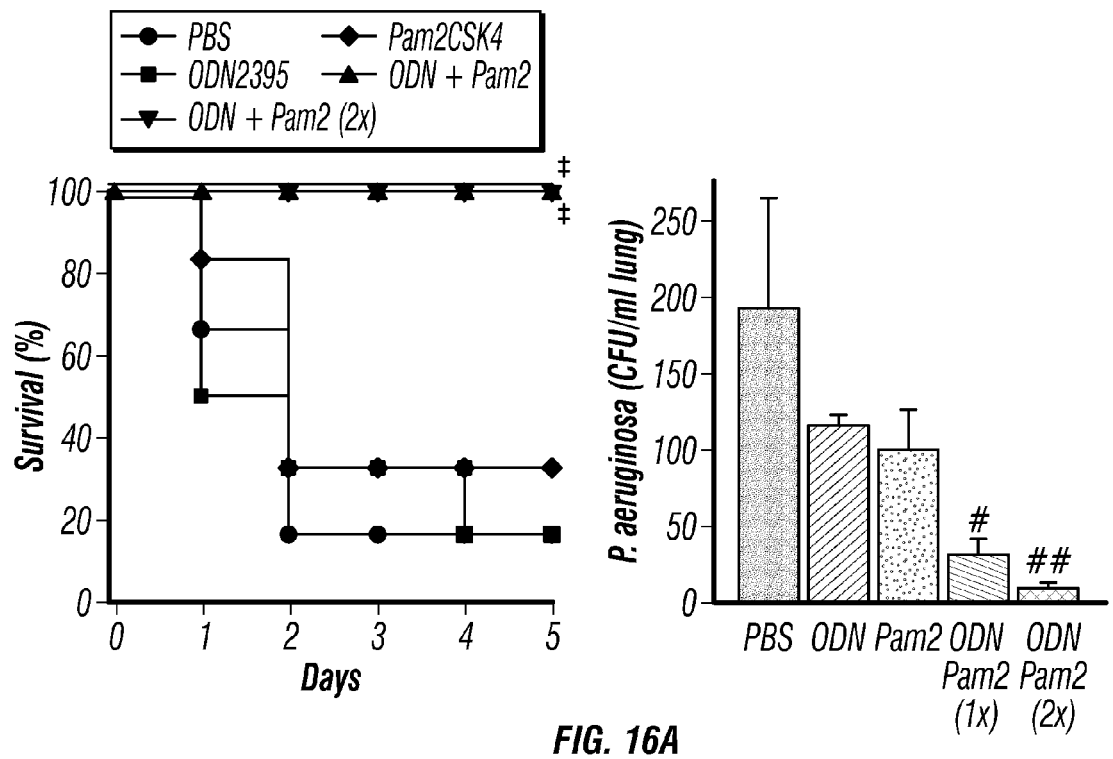
FIGS. 16A-16C. TLR2/6 and TLR9 agonists cooperate to induce resistance against bacterial pneumonia.
Figure 16B:
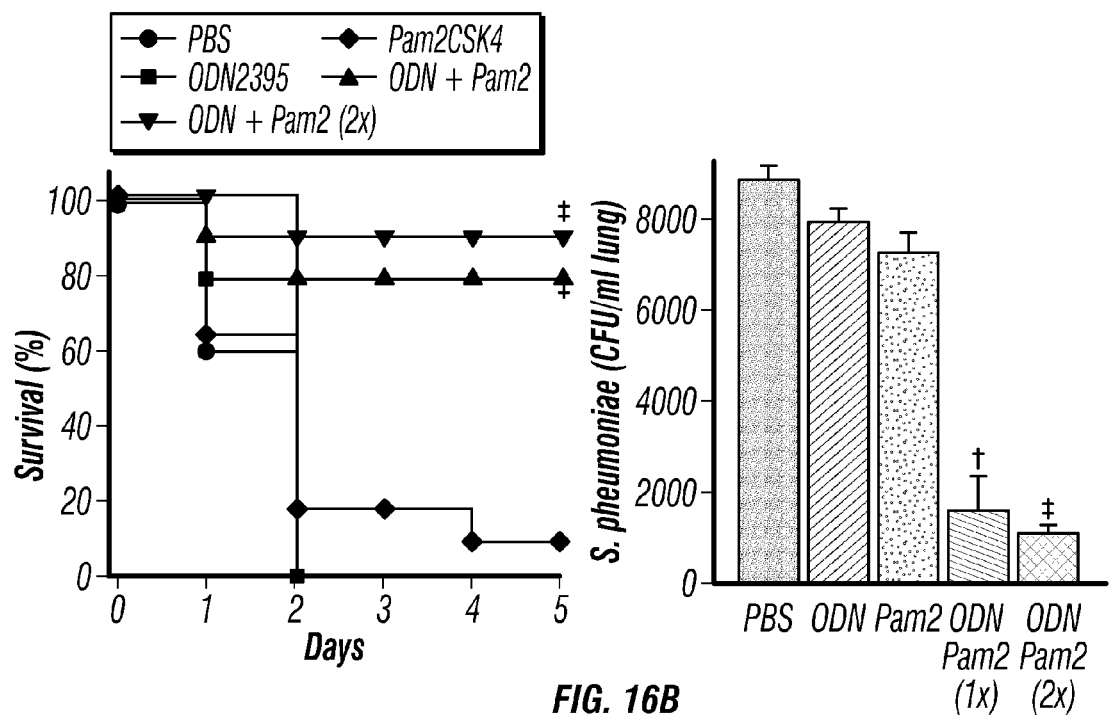
Figure 16C:
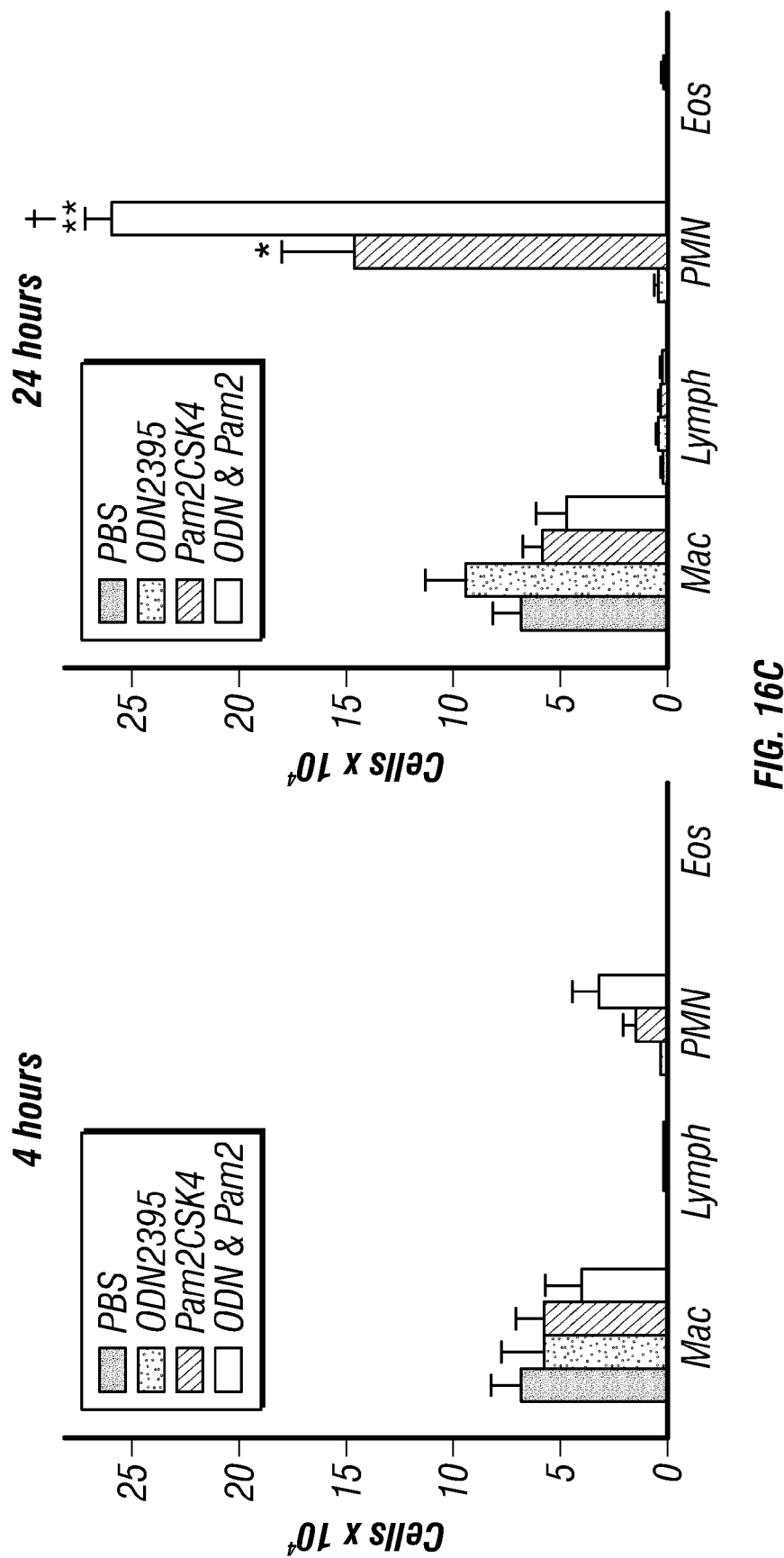

Remarkably, simultaneous treatment with Pam2CSK4 and ODN2395 (ODN+Pam2) resulted in survival of 100% of mice from an otherwise lethal challenge with Gram-negative P. aeruginosa (FIG. 16A, left), and survival of 80% from a lethal challenge with Gram-positive S. pneumoniae (FIG. 16B, left). Doubling the concentration of both ligands in the aerosol treatment resulted in 90% survival from the challenge with S. pneumoniae (FIG. 16B). Protection of mice from lethal infectious challenges was associated with synergistic killing of the pathogens within the lungs (FIGS. 16A and 16B, right), and doubling the concentration of the ligands was associated with a trend towards greater pathogen killing. Synergistic interactions between Pam2CSK4 and ODN2395 were also observed in leukocyte recruitment to the lungs at 4 and 24 h (FIG. 16C). These results indicate that ligands for TLR2/6 and TLR9 induce synergistic activation of antimicrobial effector responses, including those for pathogen killing and leukocyte recruitment, which results in a synergistic level of protection against pneumonia. Similar to the kinetics of NTHi lysate-induced resistance, protection was present by 4 h after treatment.

Not all TLR Agonist Combinations Produce Robust Protection Against Infection.

The inventors tested the following combinations of TLR agonists: Pam2+Poly (I:C), Pam2+Flg22, Pam2+Imiquimod, ODN+Poly (I:C), ODN+Flg 22, and ODN+Pam3. The inventors found that these combinations were less effective at protecting against a P. aeruginosa challenge (FIG. 17A-F), as compared to the Pam2-ODN combination (FIG. 16). These results suggest that not all TLR agonist combinations confer the same immune stimulation as Pam2-ODN.

TLR2 is Sufficient to Promote Protective Pam2CSK4 and ODN2395 Synergy, but not Required for Induced Resistance.

The detection of synergistic effects of TLR ligands Pam2CSK4 and ODN2395, which have well-defined receptor specificities, provides presumptive evidence of the participation of TLR2/6 and TLR9. The inventors sought additional evidence using knockout mice and additional ligands.

The inventors compared the survival of wild type and TLR2-deficient mice pretreated with Pam2-ODN or PBS prior to challenge with P. aeruginosa. While the wild type mice were fully protected by Pam2-ODN, there was no survival in the sham-treated wild type group or either $77r2^{-/-}$ group (FIG. 18A, left panel), confirming the requirement for TLR2 in Pam2-ODN-induced protection. The loss of protection in the Tlr2$^{-/-}$ mice correlated tightly with the loss of Pam2-ODN-induced intrapulmonary pathogen killing (FIG. 18A, right panel).

Since Pam2CSK4 and Pam3CSK4 discriminate between TLR2/6 and TLR2/1, and Pam2CSK4 but not Pam3CSK4 produces a strong synergistic protective effect when combined with ODN2395, TLR2/6 heterodimers may be required to induce lung epithelial resistance. The inventors also challenged Tlr2$^{-/-}$ and wild type mice after treatment with NTHi lysate and found neither loss of protection (FIG. 18B, left panel) nor a defect in lysate-induced bacterial killing (FIG. 18B, right panel). Taken together, these results suggest that TLR2/6 is sufficient to synergistically interact with TLR9, but is not required for all induced lung epithelial resistance.

Class C, but not Class A or B, CpG ODNs Interact Synergistically with Pam2CSK4 to Induce Resistance to Bacterial Pneumonia.

The inventors sought to further assess whether TLR9 is required for the synergistic interaction of Pam2-ODN. Because Tlr9$^{-/-}$ mice were not available, the inventors tested TLR9 involvement using a scrambled ODN known not to bind TLR9. Whereas pretreatment with Pam2-ODN resulted in 90% survival of *P. aeruginosa*-challenged mice, none survived when pretreated with Pam2CSK4 and the control ODN (FIG. 19A), indicating that TLR9 binding by the ODN is required for the synergistic protection.

To further explore the specificity of the Pam2-ODN interaction, the inventors treated wild type mice with Pam2CSK4 and different classes of CpG ODNs prior to challenge with *P. aeruginosa*. The combination of a Class A ODN (ODN 1585 or ODN 2216) or a Class B ODN (ODN 2006-G5) with Pam2SCK4 conferred no protection, whereas the combination of Pam2CSK4 with a Class C ODN (ODN M362 or ODN 2395) promoted significant resistance against otherwise lethal pneumonia (FIG. 19B). These results indicate that, not only do TLR2/6 and TLR9 ligands synergize, but that there are specific ligands that interact more favorably than others.

Pam2CSK4 and ODN2395 Induce Bacterial Killing by Epithelial Cells In Vitro.

Lung epithelial cells are induced to kill bacteria in vitro when stimulated with NTHi lysate (Clement et al., 2009; Evans et al., 2010). Since Pam2-ODN recapitulate the immunostimulatory effect of the bacterial lysate in vivo, the inventors tested whether the combination could induce pathogen killing by isolated lung epithelial cells in vitro as well. Pretreatment of murine MLE-15 respiratory epithelial cells for 4 h with Pam2-ODN significantly reduced bacterial CFUs in cell culture media after inoculation with *B. anthracis* (FIG. 20A). Similarly, treatment of human A549 cells with Pam2-ODN resulted in significant reductions in *P. aeruginosa* CFUs 4 h after infection (FIG. 20C). Demonstrating that pathogen killing occurs through stimulation of epithelial cells rather than through direct antibiotic effects of Pam2-ODN, bacteria grew to equal number in wells containing no epithelial cells, whether they were treated with Pam2-ODN or PBS (FIGS. 20B and 20D).

Thus, the antimicrobial effect is induced in both murine and human epithelial cells and results in killing of both Gram-positive and Gram-negative bacterial pathogens. These data mimic the bacterial killing seen in vivo following Pam2-ODN treatment. Serial increases in Pam2-ODN dosing up to 32-fold higher than indicated here did not significantly increase pathogen killing.

Pam2CSK4 and ODN2395 Co-Localize Intracellularly In Vitro.

The mechanism by which Pam2CSK4 and ODN2395 interact to induce synergy remains unresolved. As TLR2/6 is reported to localize to the plasma membrane and TLR9 is reported to localize to endosomes (Beutler, 2009; Dostert et al., 2008), one would not anticipate physical interaction of the ligands. However, because TLR4 may require internalization in order to signal (Kagan et al., 2008), the inventors investigated whether the two ligands were internalized by epithelial cells. A549 cells were grown in monolayer on cell culture slides, then treated with FITC-labeled Pam2CSK4 (10 μg/ml) and Texas Red-labeled ODN2395 (20 μg/ml) at the same concentrations used in the pathogen killing experiments. After 2 hours, the cells were washed, the nuclei were labeled with DAPI, and the slides were submitted to fluorescence microscopy. Both Pam2CSK4 and ODN2395 were internalized by the epithelial cells. Further, Pam2CSK4 and ODN2395 co-localize in the cytoplasmic compartment, presumably within endosomes. These results suggest that Pam2CSK4 and ODN2395 may co-localize within endosomes.

Pretreatment with the combination of Pam2CSK4, a TLR2/6 agonist, and a Class C ODN (2395, 10101 or M362), TLR9 agonists, induces high levels of resistance to lung infection with *Bacillus anthracis* and influenza virus. Mice were pretreated with aerosolized TLR ligands as indicated one day before intranasal challenge with anthrax spores or aerosol challenge with influenza virus. Survival of mice was monitored.

REFERENCES

The following references, to the extent that they provide exemplary procedural or other details supplementary to those set forth herein, are specifically incorporated herein by reference.

U.S. Pat. No. 4,554,101
U.S. Pat. No. 4,668,218
U.S. Pat. No. 4,689,338
U.S. Pat. No. 4,929,624
U.S. Pat. No. 5,238,944
U.S. Pat. No. 5,266,575
U.S. Pat. No. 5,268,376
U.S. Pat. No. 5,346,905
U.S. Pat. No. 5,352,784
U.S. Pat. No. 5,389,640
U.S. Pat. No. 5,389,640
U.S. Pat. No. 5,389,640
U.S. Pat. No. 5,395,937
U.S. Pat. No. 5,458,135
U.S. Pat. No. 5,482,936
U.S. Pat. No. 5,494,916
U.S. Pat. No. 5,525,612
U.S. Pat. No. 6,039,969
U.S. Pat. No. 6,110,929
U.S. Pat. No. 6,110,929
U.S. Pat. No. 6,194,425
U.S. Pat. No. 6,331,539
U.S. Pat. No. 6,331,539
U.S. Pat. No. 6,451,810
U.S. Pat. No. 6,488,953
U.S. Pat. No. 6,737,045
U.S. Pat. No. 6,794,357
U.S. Pat. No. 6,797,258
U.S. patent application Ser. No. 11/830,622
U.S. Patent Publn. 20030225016
U.S. Patent Publn. 2004/0162309
U.S. Patent Publn. 2004/0171086
U.S. patent Ser. No. 10/844,933
Abuchowski et al., *J. Biol. Chem.,* 252:582, 1977.
Adachi et al., *Immunity,* 9:143-150, 1998.
Akinbi et al., *J. Immunol.,* 165(10):5760-6, 2000.
Akira et al., *Biochem. Soc. Trans.,* 31 (Pt 3):637-42, 2003.
Akira et al., *Cell,* 124:783-801, 2006.
Alexopoulou et al., *Nature,* 413:732-738, 2001.
Aliprantis et al., *Science,* 285:736-739, 1999.
Aliprantis et al., *Science,* 285:736-739, 1999.
Bals and Hiemstra, *Curr. Drug Targets,* 7(6):743-50, 2006.
Bals and Hiemstra, *Eur. Respir. J.,* 23(2):327-33. 20, 2004.
Bals and Hiemstra, *Eur. Respir. J.,* 23:327-333, 2004.
Barker et al., *J. Med. Chem.,* 35:2040-2048, 1992.
Bartlett et al., *Microbiol.,* 15:147-163, 2008.
Beauchamp et al., *Anal. Biochem.,* 131:25, 1983.
Beutler, *Blood,* 113:1399-1407, 2009.
Biological Approaches to the Controlled Delivery of Drugs, R. L. Juliano, New York Academy of Sciences, 1988.
Buwitt-Beckmann et al., *FEBS J.,* 272:6354-6364, 2005.
Chen et al., *Biochim. Biophy. Acta,* 660:293, 1981.
Clement et al., *Am. J. Respir. Crit. Care Med.,* 177:1322-1330, 2008.
Clement et al., *Respir. Res.,* 10:70, 2009.

Current Protocols in Molecular Biology, Ausubel et al. (Eds.), 1987.
Dennis et al., *JAMA*, 285:2763-2773, 2001.
Dostert et al., *Adv. Drug Deliv. Rev.*, 60:830-840, 2008.
Edwards et al., *Cancer Res.*, 62:4671-4677, 2002.
European Appln. EP 0237507
Evans et al., *Am. J. Respir. Cell Mol. Biol.*, 31(4):382-94, 2004.
Evans et al., *Am. J. Respir. Cell Mol. Biol.*, 32(6): 490-7, 2005.
Evans et al., *Am. J. Respir. Cell Molec. Biol.*, 42:40-50, 2010.
Evans et al., *Annu. Rev. Physiol.*, (72)413-35, 2010.
Fanger et al., *J. Leukocyte Biology*, 66:231-236, 1999.
Forteza et al., *Am. J. Respir. Cell Mol. Biol.*, 32(5):462-9, 2005.
Gorden et al., *J. Immunol.*, 174:1259-1268, 2005.
Hayashi et al., *Nature*, 410:1099-1103, 2001.
Hiemstra, *Exp. Lung Res.*, 33:537-542, 2007.
Hippenstiel et al., *Respir. Res.*, 7:97, 2006.
Hruby et al., *Biochem J.*, 268:249-262, 1990.
Hydrolysis in Drug and Prodrug Metabolism: Chemistry, Biochemistry, and Enzymology, Bernard Testa, Vch Verlagsgesellschaft Mbh, 2003.
Ishii et al., *Cell Host Microbe.*, 3:352-363, 2008.
Janeway, Jr. and Medzhibtov, *Annu. Rev. Immunol.*, 20:197-216, 2002.
Kagan et al., *Nat. Immunol.*, 9:361-368, 2008.
Kaisho et al., *Biochim. Biophys. Acta*, 1589(1):1-13, 2002.
Keamey et al., *Immunity*, 1:327, 1994.
Kellner et al., *Biol. Chem.* 373:1:51-5, 1992.
Kita et al., *Drug Des. Delivery*, 6:157, 1990.
Knauf et al., *J. Biol. Chem.*, 263:15064, 1988.
Knowles et al., *J. Clin. Invest.*, 109(5):571-7, 2002.
Krug et al., *Eur. J. Immunol.*, 31:2154-2163, 2001.
Kyte and Doolittle, *J. Mol. Biol.*, 157(1):105-132, 1982.
Lee et al., *J. Lipid Res.*, 44:479-486, 2003.
Lee et al., *Proc. Natl. Acad. Sci. USA*, 100:6646-6651, 2003.
Martin and Frevert, *Proc. Am. Thorac. Soc.*, 2(5):403-11, 2005.
Martin et al., *Infect. Immun.*, 71:2498-2507, 2003.
Medzhitov and Janeway, Jr., *Curr. Opin. Immunol.*, 9(1):4-9, 1997.
Medzhitov and Janeway, Jr., *Trends Microbiol.*, 8(10):452-456, 2000.
Medzhitov et al., *Mol. Cell*, 2(2):253-8, 1998.
Mizgerd, *N. Engl. J. Med.*, 358:716-727, 2008.
Moghaddam et al., *Am. J. Respir. Cell Mol. Biol.*, 38:629-638, 2008.
Mondino et al., *Proc. Natl. Acad. Sci. USA*, 93(6):2245-52, 1996.
Morgan and Gainor, *Ann. Rep. Med. Chem.*, 24:243-252, 1989.
Nagase et al., *J Immunol.*, 171(8):3977-82, 2003.
O'Neill and Bowie, *Nat. Rev. Immunol.*, 7:353-364, 2007.
Or et al., *J. Org. Chem.*, 56:3146-3149, 1991.
PCT Appln. WO 00/76518
PCT Appln. WO 02/46189
PCT Appln. WO 02/46192
PCT Appln. WO 02/46193
PCT Appln. WO 94/06498
PCT Appln. WO 94/08552
PCT Appln. WO 94/16970
PCT Appln. WO 97/25086
PCT Appln. WO 98/16427
PCT Appln. WO 98/35888
PCT Appln. WO 98/55495
Poltorak et al., *Science*, 282(5396):2085-8, 1998.
Prodrugs: Topical and Ocular Drug Delivery, Kenneth Sloan, Marcel Dekker; 1992.
Pulendran et al., *J. Exp. Med.*, 188(11):2075-82, 1998.
Rogan et al., *Respir. Res.*, 7:29, 2006.
Roman et al., *Nat. Med.*, 3(8):849-54, 1997.
Schutte and McCray, *Annu. Rev. Physiol.*, 64:709-748, 2002.
Seifer et al., *Biochem. J.*, 26:795-802, 1990.
Shi et al., *J. Biol. Chem.*, 284:20540-20547, 2009.
Takeda and Akira, *J. Dermatol. Sci.*, 34(2):73-82, 2004.
Takeda and Akira, *Semin. Immunol.*, 16:3-9, 2004.
Takeuchi et al., *Int. Immunopharmacol.*, 1(4):625-35, 2001.
Travis et al., *Curr. Opin. Immunol.*, 13(1):89-95, 2001.
Tsutsumi et al., *J. Controlled Rel.*, 33:447, 1995.
Tuvim et al., *PLoS ONE*, 4:e4176, 2009.
Vroegop et al., *Intl. J. Immunopharmacol.*, 21:647-662, 1999.
Williams et al., *Am. J. Respir. Cell Mol. Biol.*, 34(5):527-36. 10, 2006.
Yamamoto et al., *Science*, 301:640-643, 2003.

The invention claimed is:

1. A pharmaceutically acceptable composition comprising a type C CpG oligodeoxynucleotide (ODN) and a TLR2/6 agonist, wherein the TLR2/6 agonist is PAM2CSK4 and wherein the composition does not further comprise an active ingredient that is an antigen.

2. The composition of claim 1, wherein the composition is formulated for nebulization.

3. The composition of claim 1, wherein the type C CpG ODN is ODN2395, ODN M362, or ODN10101.

4. The composition of claim 1, wherein the type C CpG ODN is ODN M362.

5. The composition of claim 1, wherein the composition is aerosolized.

6. The composition of claim 1, wherein the type C CpG ODN comprises:
   (a) one or more TCG sequences at 5' end of the nucleic acid or
   (b) (TCG)n, where n=1 to 3 and
   where the (TCG)n sequence is flanked by one to 5 nucleotides on the 5' end of the (TCG)n sequence.

7. The composition of claim 1, wherein the type C CpG ODN comprises the sequence TCGTCG.

8. The composition of claim 1, wherein the type C CpG ODN is in a concentration of 20 µg/ml.

9. A unit dose comprising the composition of claim 1, wherein the PAM2CSK4 is in a dosage concentration at which maximal cytokine secretion is stimulated from dendritic cells ([DCmax]).

10. A unit dose comprising the composition of claim 1, wherein the PAM2CSK4 and type C CpG ODN are in a dosage unit concentration at which neutrophilic infiltration of the lung is induced.

11. A unit dose comprising the composition of claim 1, wherein the PAM2CSK4 and type C CpG ODN are each in a dosage unit concentration of about 0.01 µg/kg to about 100 µg/kg of the individual's body weight.

12. The unit dose of claim 11, wherein the PAM2CSK4 and type C CpG ODN are each in a dosage unit concentration of about 0.01 µg/kg to about 1 µg/kg of the individual's body weight.

13. The unit dose of claim 11, wherein the PAM2CSK4 and type C CpG ODN are each in a dosage unit concentration of about 0.01 µg/kg to about 0.1 µg/kg of the individual's body weight.

14. An inhalation device comprising the pharmaceutical composition of claim 1.

15. The inhalation device of claim 14, wherein the device is for the delivery of the pharmaceutical composition by nasal inhalation.

16. The inhalation device of claim 14, wherein the inhalation device is selected from a nebulizer, a metered-dose inhaler, a sprayer, and a dry-powder inhalation device.

17. A nasal spray comprising the pharmaceutical composition of claim 1.

18. Nasal drops comprising the pharmaceutical composition of claim 1.

19. A device for nasal administration comprising a pharmaceutically acceptable composition comprising Pam2CSK4 and ODN M362 and wherein the composition does not further comprise an active ingredient that is an antigen.

20. The composition of claim 1, wherein the composition comprises glycerol.

* * * * *

SEQUENCE LISTING

```
<160> NUMBER OF SEQ ID NOS: 6

<210> SEQ ID NO 1
<211> LENGTH: 1651
<212> TYPE: PRT
<213> ORGANISM: Enterococcus faecalis

<400> SEQUENCE: 1

Met Lys Lys Lys Thr Phe Ser Phe Val Met Leu Ser Ile Leu Leu Ala
1               5                   10                  15

Gln Asn Phe Gly Phe Ala Val Asn Ala Tyr Ala Val Thr Thr Thr Glu
            20                  25                  30

Ala Gln Thr Glu Thr Thr Asp Thr Ala Lys Lys Glu Ala Glu Leu Ser
        35                  40                  45

Asn Ser Thr Pro Ser Leu Pro Leu Ala Thr Thr Thr Thr Ser Glu Met
    50                  55                  60

Asn Gln Pro Thr Ala Thr Thr Glu Ser Gln Thr Thr Glu Ala Ser Thr
65                  70                  75                  80
```

```
Thr Ala Ser Ser Asp Ala Ala Thr Pro Ser Glu Gln Gln Thr Thr Glu
                85                  90                  95

Asp Lys Asp Thr Ser Leu Asn Glu Lys Ala Leu Pro Asp Val Gln Ala
            100                 105                 110

Pro Ile Thr Asp Glu Leu Leu Asp Ser Met Ser Leu Ala Pro Ile Gly
        115                 120                 125

Gly Thr Glu Tyr Ser Gln Thr Glu Val His Arg Glu Leu Asn Thr Thr
    130                 135                 140

Pro Val Thr Ala Thr Phe Gln Phe Ala Val Gly Asn Thr Gly Tyr Ala
145                 150                 155                 160

Pro Gly Ser Val Tyr Thr Val Gln Leu Pro Glu His Leu Gly Tyr Ser
                165                 170                 175

Thr Val Ser Gly Glu Val Thr Gly Ile Gly Ala Thr Trp Ala Val Asp
            180                 185                 190

Ala Ala Thr Lys Thr Leu Ser Ile Thr Phe Asn Gln Arg Val Ser Asp
        195                 200                 205

Thr Ser Phe Lys Val Glu Leu Lys Ser Tyr Leu Thr Thr Glu Ala Glu
    210                 215                 220

Pro Leu Ile Lys Ile Glu Thr Pro Gly Lys Asn Lys Lys Thr Tyr Ser
225                 230                 235                 240

Phe Asp Leu Tyr Glu Gln Val Glu Pro Ile Gln Tyr Asn Glu Arg Thr
                245                 250                 255

Arg Thr Thr Gly Leu Asp Gly Glu Ile Phe Tyr Asn Leu Asp Arg Thr
            260                 265                 270

Leu Thr Gly Asn Gln Thr Leu Glu Leu Leu Thr Thr Glu Thr Pro Gly
        275                 280                 285

Ala Val Phe Gly Lys Gln Asp Asn Leu Glu Pro Gln Val Phe Ser Tyr
    290                 295                 300

Asp Val Asp Ile Asn Gly Gln Ile Leu Pro Glu Thr Gln Thr Leu Leu
305                 310                 315                 320

Thr Pro Gly Lys Asp Tyr Thr Leu Ser Asp Asn Ser Leu Gly Arg Ile
                325                 330                 335

Ala Val Thr Val Pro Asn Met Asn Gln Gln Lys Ala Tyr Ser Leu Ser
            340                 345                 350

Ile Asn Arg Thr Ile Tyr Leu Glu Ser Ala Ser Asp Tyr Asn Tyr Leu
        355                 360                 365

Tyr Ser Gln Gln Tyr Pro Thr Lys Ile Gly Ser Ile Ser Leu Lys
    370                 375                 380

Ser Thr Thr Gly Thr Lys Gln Thr Asp Phe Thr Ala Lys Thr Ser
385                 390                 395                 400

Gln Thr Ser Lys Val Ile Ala Asp Arg Glu Met Arg Ser Met Ser Tyr
                405                 410                 415

Ile Ser Phe Gln Ser Lys Gly Lys Tyr Tyr Val Thr Ile Tyr Gly Thr
            420                 425                 430

Leu Thr Glu Thr Lys Val Gly Gln Gln Ile Val Leu Glu Ser Thr Asn
        435                 440                 445

Gly Gln Glu Ile Lys Asn Pro Lys Phe Thr Ala Tyr Gly Pro Leu Tyr
    450                 455                 460

Glu Asn Val Lys Leu Glu Asp Tyr Phe Asp Ile Lys Thr Glu Gly Gly
465                 470                 475                 480

Lys Leu Thr Leu Thr Ala Thr Lys Asp Ser Tyr Leu Arg Ile Asn Ile
                485                 490                 495
```

```
Ser Asp Leu Thr Met Asp Phe Asp Lys Lys Asp Ile Asn Leu Ser Leu
                500                 505                 510

Ser Thr Pro Val Ile Gly Pro Asn Lys Ala Ile Gln Leu Val Ser Asp
        515                 520                 525

Gln Tyr Ile Glu Pro Ile Ser Val Val Asn Pro Leu Asn Ala Glu Thr
            530                 535                 540

Ala Trp Gly Asn Tyr Asp Gln Asn Gly Ala Tyr Ser Ser Arg Thr Thr
545                 550                 555                 560

Val Ser Val Met Gly Ser Lys Glu Lys Pro Ile Gln Asn Leu Glu Ile
                565                 570                 575

Lys Val Lys His Pro Asn Tyr Leu Ser Leu Arg Ala Thr Lys Glu Ile
            580                 585                 590

Tyr Phe Tyr Tyr Lys Leu Gly Thr Asp Tyr Thr Val Thr Pro Thr Ser
        595                 600                 605

Asp Gly Ser Val Ile Lys Phe Thr Pro Ile Thr Asn Glu Ile Gln
            610                 615                 620

Ile Pro Ile Gly Phe Asn Tyr Val Pro Asp Ser Leu Pro Lys Asp Lys
625                 630                 635                 640

Ser Ile Pro Val Asp Thr Ile Pro Ile Thr Met Ser Ala Glu Gly Leu
                645                 650                 655

Thr Pro Val Asp Thr Thr Val Thr Thr Asn Ser Lys Arg Gly Ser Glu
            660                 665                 670

Arg Thr Leu Gln Ser Ser Lys Asn Gln Phe Leu Val Asn Ala Arg Asn
        675                 680                 685

Asp Ser Phe Asp Ser Leu Ser Val Arg Thr Lys Ile Pro Ala Gly Ala
690                 695                 700

Asp Val Leu Phe Asp Ile Tyr Asp Val Ser Asn Asp Gln Val Asp Ser
705                 710                 715                 720

Ile Tyr Pro Gln Tyr Trp Asp Arg Gly Gln Tyr Phe Asp Lys Pro Met
                725                 730                 735

Thr Pro Asn Ser Pro Gly Tyr Pro Thr Ile Thr Phe Asp Glu Asn Thr
            740                 745                 750

Asn Ser Tyr Thr Phe Asp Phe Gly Lys Thr Asn Lys Arg Tyr Ile Ile
        755                 760                 765

Glu Tyr Lys Asn Ala Asn Gly Trp Ile Asp Val Pro Thr Leu Tyr Ile
    770                 775                 780

Thr Gly Thr Ala Lys Glu Pro Gln Ser Asn Asn Glu Gly Ser Ala
785                 790                 795                 800

Ser Val Ser Val Gln Asn Glu Ala Leu Asp Ile Leu Ser Ala Thr Gln
                805                 810                 815

Ala Ala Asn Pro Thr Leu Lys Asn Val Thr Lys Thr Thr Val Thr Thr
            820                 825                 830

Lys Asn Ile Asp Asn Lys Thr His Arg Val Lys Asn Pro Thr Ile Glu
        835                 840                 845

Leu Thr Pro Lys Gly Thr Thr Asn Ala Gln Ile Asp Leu Asn Ser Ile
    850                 855                 860

Thr Val Lys Gly Val Pro Glu Asp Ala Tyr Ser Leu Glu Lys Thr Thr
865                 870                 875                 880

Asn Gly Ala Lys Val Ile Phe Lys Asp Tyr Thr Leu Thr Glu Asn Ile
                885                 890                 895

Thr Ile Glu Tyr Asn Thr Val Ser Ala Asn Ala Gly Gln Ile Tyr Thr
            900                 905                 910
```

```
Glu Thr Thr Ile Asp Ser Glu Thr Leu Asn Gln Met Ser Ala Ser Lys
            915                 920                 925

Lys Lys Val Thr Thr Ala Pro Ile Thr Leu Lys Phe Ser Glu Gly Asp
    930                 935                 940

Ala Glu Gly Ile Val Tyr Leu Ala Thr Ala Thr Phe Tyr Thr His Asn
945                 950                 955                 960

Val Glu Asp Glu Asn Gln Ala Ile Ala Lys Val Ser Phe Glu Leu Ile
                965                 970                 975

Asp Asn Val Thr His Thr Ala Thr Glu Phe Thr Thr Asp Glu Lys Gly
                980                 985                 990

Gln Tyr Ser Phe Asp Ala Ile Met Thr Gly Asp Tyr Thr Leu Arg Val
            995                 1000                1005

Thr Asn Val Pro Gln Glu Tyr Ser Val Asp Glu Glu Tyr Leu Thr
    1010                1015                1020

Gly Lys Ala Ile Lys Leu Val Lys Gly Asp Asn Gln Leu Lys Ile
    1025                1030                1035

Pro Leu Thr Lys Thr Ile Asp His Ser Arg Leu Gln Val Lys Asp
    1040                1045                1050

Ser Thr Ile Tyr Val Gly Asp Ser Trp Lys Pro Glu Glu Asn Phe
    1055                1060                1065

Val Ser Ala Thr Asp Lys Thr Gly Gln Asp Val Pro Phe Glu Lys
    1070                1075                1080

Ile Thr Val Ser Gly Gln Val Asp Asn Thr Lys Ala Gly Val Tyr
    1085                1090                1095

Pro Ile Ile Tyr Ser Asp Glu Gly Lys Glu Thr Ala Tyr Val
    1100                1105                1110

Thr Val Lys Pro Asp Gln Ser Lys Leu Glu Val Lys Asp Thr Thr
    1115                1120                1125

Ile Tyr Val Gly Asp Ser Trp Lys Pro Glu Asp Asn Phe Val Ser
    1130                1135                1140

Ala Thr Asp Lys Thr Gly Gln Asp Val Pro Phe Glu Lys Ile Asp
    1145                1150                1155

Val Gln Gly Thr Val Asn Val Asp Lys Ile Gly Asp Tyr Glu Ile
    1160                1165                1170

Val Tyr Lys Asn Gly Lys Lys Glu Ala Lys Ala Ile Val His Val
    1175                1180                1185

Arg Asp Asp Ser Gln Leu Glu Val Lys Asp Thr Thr Ile Tyr Val
    1190                1195                1200

Gly Asp Ser Trp Lys Pro Glu Asp Asn Phe Val Ser Ala Thr Asp
    1205                1210                1215

Lys Thr Gly Gln Asp Val Pro Phe Glu Lys Ile Thr Val Ser Gly
    1220                1225                1230

Gln Val Asp Thr Ser Lys Ala Gly Val Tyr Pro Ile Val Tyr Ser
    1235                1240                1245

Tyr Glu Gly Lys Glu Glu Thr Ala Asn Val Thr Val Lys Pro Asp
    1250                1255                1260

Gln Ser Lys Leu Glu Val Lys Asp Thr Thr Ile Tyr Val Gly Asp
    1265                1270                1275

Lys Trp Glu Pro Glu Asp Asn Phe Val Ser Ala Thr Asp Lys Thr
    1280                1285                1290

Gly Gln Asp Val Pro Phe Glu Lys Ile Asp Val Gln Gly Thr Val
    1295                1300                1305
```

```
Asn Val Asp Lys Ile Gly Asp Tyr Glu Ile Val Tyr Lys Asn Gly
1310                1315                1320

Thr Lys Glu Ala Lys Ala Ile Val His Val Arg Asp Asp Ser Gln
    1325                1330                1335

Leu Glu Val Lys Asp Thr Thr Ile Tyr Val Gly Asp Lys Trp Glu
        1340                1345                1350

Ala Glu Asp Asn Phe Val Ser Ala Thr Asp Lys Thr Gly Gln Asp
    1355                1360                1365

Val Pro Phe Glu Lys Ile Asp Val Gln Gly Thr Val Asn Val Asp
    1370                1375                1380

Lys Ile Gly Asp Tyr Glu Ile Val Tyr Lys Asn Gly Thr Lys Glu
    1385                1390                1395

Ala Lys Ala Ile Val His Val Arg Asp Asp Ser Arg Leu Gln Val
    1400                1405                1410

Lys Asp Thr Thr Ile Tyr Val Gly Asp Ser Trp Lys Pro Glu Glu
    1415                1420                1425

Asn Phe Val Ser Ala Thr Asp Lys Thr Gly Gln Asp Val Pro Phe
    1430                1435                1440

Glu Lys Ile Thr Val Ser Gly Gln Val Asp Thr Ser Lys Ala Gly
    1445                1450                1455

Val Tyr Pro Ile Ile Tyr Ser Tyr Glu Gly Lys Glu Glu Thr Ala
    1460                1465                1470

His Val Ala Val Lys Pro Asp Gln Ser Lys Leu Glu Val Lys Asp
    1475                1480                1485

Thr Thr Ile Tyr Val Gly Asp Ser Trp Lys Pro Glu Asp Asn Phe
    1490                1495                1500

Val Ser Ala Thr Asp Arg Asp Gly His Ala Ile Ser Phe Asp Lys
    1505                1510                1515

Val Gln Val Lys Gly Glu Val Asp Thr Lys Lys Thr Gly Glu Tyr
    1520                1525                1530

Gln Ile Ser Tyr Thr Thr Glu Pro Val Asn Glu Thr Lys Pro Ala
    1535                1540                1545

Val Gln Ser Arg Leu Phe Ser Met Phe Ser Asn Glu Thr Pro Arg
    1550                1555                1560

Gln Leu Thr Thr Val Ala Thr Val His Val Ile Asp Arg Asn Pro
    1565                1570                1575

Thr Pro Leu Pro Asp Lys Asn Glu Asn Asn Gln Thr Ser Ser Ser
    1580                1585                1590

Thr Asn Gln Thr Thr Ile Lys Ser Ser Gln Tyr Val Thr His Ile
    1595                1600                1605

Val Lys Pro Asp Lys Gln Gly Arg Tyr Pro Lys Thr Gly Glu Gln
    1610                1615                1620

Thr Asn Gly Leu Tyr Arg Val Leu Gly Leu Val Val Leu Leu Ile
    1625                1630                1635

Val Ile Ile Ser Gly Ile Val Ile Lys Lys Lys Arg Lys
    1640                1645                1650

<210> SEQ ID NO 2
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 2
```

```
Gln Arg Leu Ser Thr Gly Ser Arg Ile Asn Ser Ala Lys Asp Asp Ala
1               5                   10                  15

Ala Gly Leu Gln Ile Ala
            20

<210> SEQ ID NO 3
<211> LENGTH: 13
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (4)..(5)
<223> OTHER INFORMATION: n is a a, c, g, or t
<220> FEATURE:
<221> NAME/KEY: misc_feature
<222> LOCATION: (9)..(10)
<223> OTHER INFORMATION: n is a a, c, g, or t

<400> SEQUENCE: 3
tcgnntcgnn tcg                                                          13

<210> SEQ ID NO 4
<211> LENGTH: 22
<212> TYPE: DNA
<213> ORGANISM: Artificial Sequence
<220> FEATURE:
<223> OTHER INFORMATION: Synthetic Primer

<400> SEQUENCE: 4
tcgtcgtttt cggcgcgcgc cg                                                22

<210> SEQ ID NO 5
<211> LENGTH: 25
<212> TYPE: DNA
<213> ORGANISM: Artificial Sequence
<220> FEATURE:
<223> OTHER INFORMATION: Synthetic Primer

<400> SEQUENCE: 5
tcgtcgtcgt tcgaacgacg ttgat                                             25

<210> SEQ ID NO 6
<211> LENGTH: 22
<212> TYPE: DNA
<213> ORGANISM: Artificial Sequence
<220> FEATURE:
<223> OTHER INFORMATION: Synthetic Primer

<400> SEQUENCE: 6
tcgtcgtttt cggcggccgc cg                                                22
```